US010072036B2

United States Patent
Buchmeiser et al.

(10) Patent No.: US 10,072,036 B2
(45) Date of Patent: Sep. 11, 2018

(54) N-HETEROCYCLIC CARBENE COMPLEXES OF METAL IMIDO ALKYLIDENES AND METAL OXO ALKYLIDENES, AND THE USE OF SAME

(71) Applicant: UNIVERSITÄT STUTTGART, Stuttgart (DE)

(72) Inventors: Michael R. Buchmeiser, Remshalden (DE); Suman Sen, Tamluk (IN); Roman Schowner, Trossingen (DE)

(73) Assignee: UNIVERSITÄT STUTTGART, Stuttgart (DE)

( * ) Notice: Subject to any disclaimer, the term of this patent is extended or adjusted under 35 U.S.C. 154(b) by 0 days.

(21) Appl. No.: 15/306,521

(22) PCT Filed: Apr. 24, 2015

(86) PCT No.: PCT/EP2015/058888
§ 371 (c)(1),
(2) Date: Oct. 25, 2016

(87) PCT Pub. No.: WO2015/162245
PCT Pub. Date: Oct. 29, 2015

(65) Prior Publication Data
US 2017/0050994 A1     Feb. 23, 2017

(30) Foreign Application Priority Data
Apr. 25, 2014  (DE) .................. 10 2014 105 885

(51) Int. Cl.
| | |
|---|---|
| C07F 11/00 | (2006.01) |
| C07C 6/04 | (2006.01) |
| C08G 61/08 | (2006.01) |
| C08G 61/12 | (2006.01) |
| C07C 319/20 | (2006.01) |
| C07C 253/30 | (2006.01) |
| C07C 67/333 | (2006.01) |
| B01J 31/18 | (2006.01) |
| B01J 31/22 | (2006.01) |

(52) U.S. Cl.
CPC ........... *C07F 11/00* (2013.01); *B01J 31/1805* (2013.01); *B01J 31/2273* (2013.01); *B01J 31/2278* (2013.01); *C07C 6/04* (2013.01); *C07C 67/333* (2013.01); *C07C 253/30* (2013.01); *C07C 319/20* (2013.01); *C08G 61/08* (2013.01); *C08G 61/12* (2013.01); *B01J 2231/543* (2013.01); *B01J 2531/64* (2013.01); *B01J 2531/66* (2013.01); *C07C 2531/22* (2013.01); *C07C 2601/10* (2017.05); *C07C 2601/16* (2017.05); *C08G 2261/418* (2013.01); *C08G 2261/419* (2013.01)

(58) Field of Classification Search
CPC ............... B01J 31/2265; B01J 31/2269; B01J 31/2273; B01J 31/2278; C07F 11/00
See application file for complete search history.

(56) References Cited

U.S. PATENT DOCUMENTS

| | | | | |
|---|---|---|---|---|
| 7,094,898 B2* | 8/2006 | Fogg | .................... | B01J 31/1616 502/152 |
| 8,536,277 B2* | 9/2013 | Mueller | ............... | B01J 31/2265 502/203 |
| 8,546,300 B2* | 10/2013 | Uchimura | ................ | B41M 5/42 503/207 |
| 8,809,563 B2* | 8/2014 | Holtcamp | ............ | C07D 207/06 556/22 |
| 9,024,034 B2* | 5/2015 | Holtcamp | ........... | C07F 15/0046 548/103 |
| 9,206,211 B2* | 12/2015 | Schrock | ................... | C07F 11/00 |
| 9,233,362 B2* | 1/2016 | Furstner | .................. | C07F 11/00 |
| 9,512,157 B2* | 12/2016 | Kunz | .................. | C07F 15/0046 |
| 2003/0181776 A1* | 9/2003 | Basset | ................. | B01J 31/1625 585/531 |
| 2006/0128912 A1* | 6/2006 | Piers | .................... | B01J 31/2265 526/171 |

OTHER PUBLICATIONS

Buchmeiser, M.R.; Sen, S.; Unold, J.; Frey W. Angew. Chem. Int. Ed. Eng. 2014, 53, 9384-9388.*
Michael R. Buchmeiser et al: "N-Heterocyclic Carbene, High Oxidation State Molybdenum Alkylidene Complexes: Functional-Group-Tolerant Cationic Metathesis Cationic Metathesis Catalysts", Angewandte Chemie International Edition, vol. 53, No. 35, Aug. 25, 2014 (Aug. 25, 2014), pp. 9384-9388, XP055203685, ISSN: 1433-7851, DOI: 10.102/anie.201404655.
Cezary Samojlowicz et al: "Ruthenium-Based Olefin Metathesis Catalysts Bearing N-Heterocyclic Carbene Ligands", Chemical Reviews, vol. 109, No. 8, Aug. 12, 2009 (Aug. 12, 2009), pp. 3708-3742, XP055071094, ISSN; 0009-2655, DOI: 10.1021/cr800524f the whole document.

* cited by examiner

*Primary Examiner* — Rip A Lee
(74) *Attorney, Agent, or Firm* — Harness, Dickey & Pierce, P.L.C.

(57) ABSTRACT

The invention relates to an N-heterocyclic carbene complex of general formulas I to IV (I) (II) (III) (IV), according to which A1 stands for NR2 or PR2, A2 stands for CR2 R2', NR2, PR2, 0 or S, A3 stands for N or P, and C stands for a carbene carbon atom, ring B is an unsubstituted or a mono or poly-substituted 5 to 7-membered ring, substituents R2 and R2' stand, inter alia, for a linear or branched C1-Cw-alkyl group and, if N and N each stand for NR2 or PR2, are the same or different, M in formulas I, II, III or IV stands for Cr, Mo or W, X 1 or X2 in formulas I to IV are the same or different and represent, inter alia, C1-C1s carboxylates and C1-C1s-alkoxides, Y is inter alia oxygen or sulphur, Z is inter alia a linear or branched C1-Cw-alkylenoxy group, and R 1 and R1' in formulas I to IV are, inter alia, an aliphatic or aromatic group. These compounds are particularly suitable for use as catalysts for olefin metathesis reactions and have the advantage, compared to known Schrock carbene complexes, of displaying clearly increased tolerance to functional groups such as, in particular, aldehydes, secondary amines, nitriles, carboxylic acids and alcohols.

19 Claims, No Drawings

N-HETEROCYCLIC CARBENE COMPLEXES OF METAL IMIDO ALKYLIDENES AND METAL OXO ALKYLIDENES, AND THE USE OF SAME

CROSS-REFERENCE TO RELATED APPLICATIONS

This application is a National Stage of International Application No. PCT/EP2015/058888, filed Apr. 24, 2015. This application claims the benefit of and priority to European Patent Application 1020141058852, filed Apr. 25, 2014, The entire disclosures of the above applications are incorporated herein by reference.

The invention relates to N-heterocyclic carbene complexes of metal imido alkylidenes and metal oxo alkylidenes, and to the use thereof as catalysts in olefin metathesis reactions.

Alkylidene complexes of metals of group VI (Cr, Mo, W) in their highest oxidation state ("high oxidation state metal alkylidenes") have been known for many years (Chem. Rev. 2002, 102, 145; Chem. Commun. 2005, 2773; Chem. Rev. 2009, 109, 3211). Compounds of the general formulae M(NR)(CHR')$X^1X^2$ and M(O)(CHR')$X^1X^2$ in which R is alkoxy, an aryl or adamantyl radical, R' is t-butyl or CMe$_2$Ph and $X^1$ and $X^2$ are alkoxy, aryloxy, pyrrolide radicals and the like, while M is a metal in the form of molybdenum or tungsten, are also referred to as "Schrock carbenes" or "Schrock catalysts". Compounds of this kind have high activity in various (asymmetric and desymmetrizing) olefin metathesis reactions, and have been used successfully in ring-closing metatheses, cross-metatheses, ring-opening cross-metatheses, (cross-)ene-yne metatheses, ring-closing ene-yne metatheses, cross-ene-diyne metatheses, tandem ring-opening-ring-closing metatheses, ring-opening metathesis polymerizations (ROMP), 1-alkyne polymerizations, acyclic metathesis polymerizations (ADMET) or in cyclopolymerizations of α,ω-diynes. In the case of the known Schrock catalysts, however, the low tolerance thereof with respect to functional groups, such as, more particularly, ketones, aldehydes and isocyanates, and protic compounds such as alcohols, thiols, carboxylic acids, and primary or secondary amines, has been found to be disadvantageous. In the case of substrates that contain such functional groups, relatively rapid deactivation or breakdown of the catalyst has therefore been observed.

For this reason, there is a need for catalysts of the "Schrock type" having maximum tolerance with respect to various functional groups and simultaneously having maximum activity. It is accordingly an object of the invention to propose an advantageous catalyst system that remedies these shortcomings.

This object is achieved in accordance with the invention by an N-heterocyclic carbene complex of the general formula I, II, III or IV

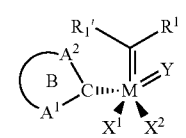

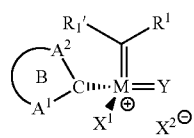

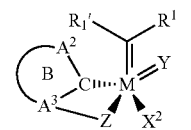

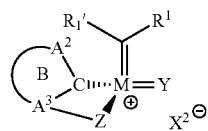

which is characterized in that $A^1$ is $NR^2$ or $PR^2$, $A^2$ is $CR^2R^{2'}$, $NR^2$, $PR^2$, O or S, $A^3$ is N or P, C is a carbene carbon atom, the ring B is an unsubstituted or a mono- or polysubstituted 5- to 7-membered ring which, as well as $A^1$, $A^2$ and/or $A^3$, may contain further heteroatoms in the form of nitrogen, phosphorus, oxygen or sulfur and wherein the substituents may have the definition described for $R^2$, the substituents $R^2$ and $R^{2'}$ are independently H, a linear, partly cyclic or branched $C_1$-$C_{18}$-alkyl, especially a $C_1$-$C_7$-alkyl, a linear, partly cyclic or branched $C_2$-$C_{18}$-alkenyl, especially a $C_2$-$C_7$-alkenyl, a $C_3$-$C_{12}$-cycloalkyl, especially a $C_3$-$C_6$-cycloalkyl, a linear, partly cyclic or branched $C_6$-$C_{100}$-polyoxaalkyl, especially $C_6$-$C_{30}$-polyoxaalkyl, a $C_5$-$C_{14}$-aryl or -heteroaryl radical, a $C_5$-$C_{14}$-aryloxy, a linear, partly cyclic or branched $C_1$-$C_{18}$-perfluoroalkyl, especially $C_1$-$C_7$-perfluoroalkyl, a linear, partly cyclic or branched $C_1$-$C_{18}$-perchloroalkyl, especially a $C_1$-$C_7$-perchloroalkyl, a linear, partly cyclic or branched part-fluorinated $C_1$-$C_{18}$-alkyl, especially a part-fluorinated $C_1$-$C_7$-alkyl, a linear, partly cyclic or branched part-chlorinated $C_1$-$C_{18}$-alkyl, especially a part-chlorinated $C_1$-$C_7$-alkyl, a per- or part-fluorinated $C_6$-$C_{14}$-aryl, a per- or part-chlorinated $C_5$-$C_{14}$-aryl radical, and, when $A^1$ and $A^2$ are each $NR^2$ or $PR^2$, $R^2$ may be the same or different, or $R^2$ and $R^{2'}$ together are a linear or branched $C_1$-$C_{18}$-alkylene, especially a $C_1$-$C_7$-alkylene radical, M in the formulae I, II, III and IV is Cr, Mo or W, $X^1$ and $X^2$ in formulae I to IV are the same or different and are selected from the group comprising $C_1$-$C_{18}$ carboxylates, $C_1$-$C_{18}$-alkoxides, fluorinated $C_1$-$C_{18}$ alkoxides, $C_1$-$C_{18}$ mono- or polyhalogenated carboxylates, unsubstituted or mono- or polysubstituted $C_6$-$C_{18}$ mono-, bi- or terphenoxides, trifluoromethanesulfonate, non-coordinating anions, especially tetrakis(3,5-bis-(trifluoromethyl)phenyl)borate, tetrakis(penta-fluorophenyl)borate, tetrakis(nonafluoro-t-butoxy)-aluminate, tetrafluoroborate, hexafluorophosphate and hexafluoroantimonate, where the substituents on the mono-, bi- or terphenoxides, in addition to halogen, may have the same definition as $R^2$, Y is oxygen, sulfur, an N-adamantyl, an N-tert-butyl, a $C_6$-$C_{14}$—N-aryl radical, especially a $C_6$-$C_{10}$—N-aryl radical, where the aryl radical may be mono- or polysubstituted by halogen, a linear or branched $C_1$-$C_{18}$ alkyl, a linear or branched $C_1$-$C_{18}$ alkyloxy or an unsubstituted or substituted phenyl radical wherein the substituents have the same definition as $R^2$, Z is a linear, partly cyclic or branched $C_1$-$C_{10}$-alkyleneoxy, especially a $C_1$-$C_5$-alkyleneoxy, a linear, partly cyclic or branched $C_1$-$C_{10}$-alkylenethio, especially a $C_1$-$C_5$-alkylenethio, a linear, partly cyclic or branched $C_1$-$C_{10}$-alkylene-$NR^2$, especially a $C_1$-$C_5$-alkylene-$NR^2$, a $C_6$-$C_{10}$-aryleneoxy, a per- or part-fluorinated $C_6$-$C_{14}$-aryleneoxy, a per- or part-chlorinated $C_6$-$C_{14}$-aryleneoxy, a per- or part-brominated $C_6$-$C_{14}$-aryleneoxy, a $C_6$-$C_{14}$-arylenethio, a per- or part-fluorinated $C_6$-$C_{14}$-arylenethio, a per- or part-chlorinated $C_6$-$C_{14}$-arylenethio radical, a per- or part-brominated $C_6$-$C_{14}$-arylenethio or a $C_6$-$C_{14}$-arylene-$NR^2$, a per- or part-fluorinated $C_6$-$C_{14}$-arylene-$NR^2$, a per- or part-chlorinated $C_6$-$C_{14}$-arylene-$NR^2$, a per- or part-brominated $C_6$-$C_{14}$-arylene-$NR^2$, a $C_6$-$C_{14}$-arylene-$PR^2$, a per- or part-fluorinated $C_6$-$C_{14}$-arylene-$PR^2$, a per- or part-chlorinated $C_6$-$C_{14}$-arylene-$PR^2$, a per- or part-brominated $C_6$-$C_{14}$-arylene-$PR^2$, a carboxyl, a thiocarboxyl or a dithiocarboxyl group, and $R^1$ and $R^{1'}$ in the formulae I to IV are independently H or an aliphatic or aromatic radical, especially a linear or branched $C_1$-$C_{18}$ alkyl group, preferably in the form of a tert-butyl or $CMe_2Ph$ group, or an unsubstituted or mono- or polysubstituted $C_6$-$C_{14}$-aryl group, where the substituents have the definitions given for $R^2$, preferably in the form of 2-(2-propoxy)phen-1-yl, 2-methoxyphen-1-yl, 2,4,5-trimethoxyphenyl or ferrocenyl.

The invention further relates to the use of these compounds as catalyst in olefin metathesis reactions.

Preferred configurations of the carbene complexes of the invention are apparent from claims 2 to 6, while claims 7 to 13 describe preferred configurations of the use teaching of the invention.

For the inventive carbene complexes of the general formulae I to IV, it is preferable when the linear, partly cyclic or branched $C_1$-$C_{18}$-alkyl group mentioned for the substituents $R^2$ and $R^{2'}$ takes the form of a $C_1$-$C_{10}$-alkyl group, preferably of a $C_1$-$C_7$-alkyl group and especially of a $C_1$-$C_4$-alkyl group. Methyl, ethyl and propyl groups are particularly suitable.

The linear, partly cyclic or branched $C_2$-$C_{18}$-alkenyl group is appropriately in the form of a $C_2$-$C_{10}$-alkenyl group, especially in the form of a $C_2$-$C_7$-alkenyl group and preferably in the form of butenyl or hexenyl. For the $C_3$-$C_{12}$-cycloalkyl group, it is preferable when this is in the form of a $C_3$-$C_6$-cycloalkyl group. Suitable groups that should be mentioned in this context are cyclopentyl and cyclohexyl. If the substituent $R^2$ or $R^{2'}$ is a linear, partly cyclic or branched $C_6$-$C_{100}$-polyoxaalkyl radical, it is advantageous when this is in the form of a $C_6$-$C_{30}$-polyoxaalkyl radical and especially in the form of a $C_6$-$C_{15}$-polyoxaalkyl radical. Suitable radicals are, for example, methyloxyethyl or methyloxyethyloxy.

The substituted or unsubstituted $C_5$-$C_{14}$-aryl or -heteroaryl radical is preferably in the form of a $C_6$-$C_{14}$-aryl or -heteroaryl radical, especially a $C_6$-$C_{10}$-aryl or -heteroaryl radical. In this context, phenyl, naphthyl or ferrocenyl radicals have been found to be particularly suitable.

Preferred substituted or unsubstituted $C_5$-$C_{14}$-aryloxy radicals are $C_6$-$C_{14}$-aryloxy radicals and especially $C_6$-$C_{10}$-aryloxy radicals. Particularly suitable unsubstituted aryloxy radicals are phenyloxy or naphthyloxy.

The linear, partly cyclic or branched $C_1$-$C_{18}$ perfluorinated alkyl radical is especially in the form of a $C_1$-$C_{10}$ perfluorinated alkyl radical, preferably in the form of a $C_1$-$C_7$ perfluorinated alkyl radical, and more preferably in the form of a $C_1$-$C_4$-perfluoroalkyl radical, trifluoromethyl being the most preferred radical.

The linear, partly cyclic or branched $C_1$-$C_{18}$ perchlorinated alkyl radical is likewise especially in the form of a $C_1$-$C_{10}$ perchlorinated alkyl radical, preferably in the form of a $C_1$-$C_7$ perchlorinated alkyl radical, and more preferably in the form of a $C_1$-$C_4$-perchloroalkyl radical, trichloromethyl being the most preferred radical.

The linear, partly cyclic or branched part-fluorinated $C_1$-$C_{18}$-alkyl radical is preferably in the form of a part-fluorinated $C_1$-$C_{10}$-alkyl radical, and especially in the form of a part-fluorinated $C_1$-$C_7$-alkyl radical. One example of such a radical is trifluoroethyl.

The linear, partly cyclic or branched part-chlorinated $C_1$-$C_{18}$-alkyl radical is preferably in the form of a part-chlorinated $C_1$-$C_{10}$-alkyl radical, and especially in the form of a part-chlorinated $C_1$-$C_7$-alkyl radical. One example of such a radical is trichloroethyl.

The perfluorinated $C_5$-$C_{14}$-aryl radical is especially in the form of a perfluorinated $C_6$-$C_{14}$-aryl radical, preferably in the form of a perfluorinated $C_6$-$C_{10}$-aryl radical and more preferably in the form of a pentafluorophenyl radical.

The part-fluorinated $C_5$-$C_{14}$-aryl radical is likewise especially in the form of a part-fluorinated $C_6$-$C_{14}$-aryl radical, preferably in the form of a part-fluorinated $C_6$-$C_{10}$-aryl radical and particularly and preferably in the form of fluorophenyl.

The perchlorinated $C_5$-$C_{14}$-aryl radical is especially in the form of a perchlorinated $C_6$-$C_{14}$-aryl radical, preferably in the form of a perchlorinated $C_6$-$C_{10}$-aryl radical and particularly and preferably in the form of a pentachlorophenyl radical.

The part-chlorinated $C_5$-$C_{14}$-aryl radical is likewise especially in the form of a part-chlorinated $C_6$-$C_{14}$-aryl radical, preferably in the form of a part-chlorinated $C_6$-$C_{10}$-aryl radical and particularly and preferably in the form of chlorophenyl.

When $A^1$ and $A^2$ are each $NR^2$ or $PR^2$, the $R^2$ and $R^{2'}$ radicals may be the same or different.

In general, it is preferably the case for the $R^2$ substituent, if it is bonded directly to one of the $A^1$ or $A^2$ substituents, that it is a substituent other than hydrogen.

If $R^2$ and $R^{2'}$ together form a linear or branched $C_1$-$C_{18}$-alkylene group, it is preferably in the form of a $C_1$-$C_7$-alkylene group and more preferably in the form of a butylene or pentylene group.

In the context of the present invention, $A^1$ is preferably $NR^2$. Independently thereof, $A^2$ is preferably $NR^2$ or S and more preferably $NR^2$.

The ring B is a heterocyclic 5- to 7-membered ring having, directly adjacent to the carbenoid carbon (i.e. the carbon atom present in the form of a carbene), at least one nitrogen atom and additionally either a further nitrogen atom, sulfur atom, oxygen atom, phosphorus atom or quaternary carbon atom. Preferably, the heterocyclic 5- to 7-membered ring has, directly adjacent to the carbenoid carbon, at least one nitrogen atom and additionally either a further nitrogen atom or sulfur atom. The nitrogen atoms and phosphorus atoms in this case have a substituent $R^2$ which is not in the form of hydrogen, such that the nitrogen atoms in the ring B are tertiary amines or phosphines. In addition, the heterocyclic ring B may be substituted, for example by phenyl, or may form a bicyclic or polycyclic system with a further, preferably aromatic ring. For example, the ring B may be a benzofused, naphthofused, phenanthrene- or anthraquinone-fused 5- to 7-membered ring. In addition, the ring B may have further substituents in the form of halogens, $C_1$-$C_{18}$ carboxylic esters, carboxamides, sulfonamides, sulfonic esters, alkyl nitriles, ethers, thioethers, amines. For the substituents, it is preferable when they contain 1 to 8 carbon atoms. Particularly preferred substituents are fluorine, chlorine and bromine, and also methoxycarbonyl and ethoxycarbonyl.

In the context of the present invention, it has been found to be particularly appropriate when the ring B is a heterocycle selected from the group comprising 1,3-disubstituted imidazol-2-ylidenes, 1,3-disubstituted imidazolin-2-ylidenes, 1,3-disubstituted tetrahydropyrimidin-2-ylidenes, 1,3-disubstituted diazepin-2-ylidenes, 1,3-disubstituted dihydrodiazepin-2-ylidenes, 1,3-disubstituted tetrahydrodiazepin-2-ylidenes, N-substituted thiazol-2-ylidenes, N-substituted thiazolin-2-ylidenes, N-substituted triazol-2-ylidenes, N-substituted dihydrotriazol-2-ylidenes, mono- or polysubstituted triazolin-2-ylidenes, N-substituted thiadiazol-2-ylidenes, mono- or polysubstituted thiadiazolin-2-ylidenes and mono- or polysubstituted tetrahydrotriazol-2-ylidenes.

More preferably, the ring B is derived from a 1,3-disubstituted imidazol-2-ylidene or a 1,3-disubstituted imidazolin-2-ylidene. The substituent $R^2$ in this case appropriately consists of a branched $C_3$-$C_6$-alkyl radical, especially in the form of a t-butyl, or a substituted aryl radical, especially in the form of a 2,4,6-trimethylphenyl radical (also referred to as mesityl group).

The metal in the carbene complex of the general formulae I to IV is preferably Mo or W, especially Mo.

If at least one of the two substituents $X^1$ and $X^2$ is in the form of a $C_1$-$C_{18}$-carboxylate, it is preferable when this is a $C_1$-$C_5$-carboxylate. Particularly suitable carboxylates include the acetate, propionate and benzoate.

If at least one of the two substituents $X^1$ and $X^2$ is in the form of a $C_1$-$C_{18}$-alkoxide, it is preferable when this is a $C_1$-$C_8$-alkoxide. Particularly suitable alkoxides include the 2-propoxide and the tert-butoxide.

If at least one of the two substituents $X^1$ and $X^2$ is in the form of a fluorinated $C_1$-$C_{18}$-alkoxide, it is preferable when this is a fluorinated $C_1$-$C_8$-alkoxide. Particularly suitable fluorinated alkoxides include the hexafluoro-2-propoxide and a hexafluoro-tert-butoxide.

If at least one of the two substituents $X^1$ and $X^2$ is in the form of a mono- or polyhalogenated $C_1$-$C_{18}$-carboxylate, it is preferable when this is a mono- or polyhalogenated $C_1$-$C_8$-carboxylate. Particularly suitable mono- or polyhalogenated $C_1$-$C_8$-carboxylates include trichloroacetate, trifluoroacetate, pentafluoro-propionate, heptafluorobutyrate and pentafluoro-benzoate.

Preferred unsubstituted or mono- or polysubstituted mono-, bi- or terphenoxides are 2,6-diphenylphenoxide, 2',2'',6',6''-tetrakis(2-propyl)-2,6-diphenylphenoxide and 2',2',6',6''-tetramethyl-2,6-diphenylphenoxide.

In general, the substituents $X^1$ and $X^2$ should be weakly coordinating or non-coordinating anions and especially anionic P-, B-, Al- or Sb-based anions.

For the substituents $X^1$ and $X^2$, weakly coordinating substituents in particular, for example trifluoromethanesulfonate, tetrakis(3,5-bis(trifluoromethyl)-phenyl)borate, hexafluorophosphate and hexafluoroantimonate substituents have been found to be particularly appropriate. In addition, it is possible to use substituents such as fluorinated and non-fluorinated $C_1$-$C_{18}$-alkoxides, especially in the form of $C_1$-$C_4$-alkoxides. Particularly suitable alkoxides are ethoxide, 2-propoxide, tert-butoxide, hexafluoro-2-propoxide or hexafluoro-tert-butoxide.

Useful substituents Y include the substituents referred to above. The following applies in respect of preferred embodiments of these substituents: the $C_6$-$C_{14}$—N-aryl radical is preferably in the form of a $C_6$-$C_{10}$—N-aryl radical, where the aryl radical may be mono- or polysubstituted by halogen, $C_1$-$C_{18}$-alkyl radicals, especially $C_1$-$C_8$-alkyl radicals, $C_1$-$C_{18}$-alkyloxy radicals, especially $C_1$-$C_8$-alkyloxy radicals, particular preference being given to methoxy or 2-propoxy groups, or an unsubstituted or substituted phenyl radical wherein the substituents may have the same definition as for $R^2$.

Particularly preferred substituents Y especially include 2,6-disubstituted N-aryl radicals, preferably in the form of N-phenyl radicals, in which the substituents are preferably in the form of alkyl radicals, such as tert-butyl, iso-propyl or methyl, or in the form of halogens, such as chlorine, fluorine or bromine or mixtures thereof. Further-preferred substituents Y are N-alkyl radicals in which the carbon atom directly adjacent to the nitrogen is a quaternary carbon atom. Examples of such N-alkyl radicals are the N-tert-butyl or the N-adamantyl radical. Particularly preferred substituents Y in the context of the present invention are the N-2,6-dimethylphenyl radical, the 2,6-bis(2-propyl)phenyl radical, the pentafluorophenyl radical, the N-2,6-dichlorophenyl radical, the 2-tert-butylphenyl radical, the N-tert-butyl radical and the N-adamantyl radical.

The following applies in respect of preferred configurations of the substituent Z:
the linear, partly cyclic or branched $C_1$-$C_{10}$-alkyleneoxy group is preferably a $C_1$-$C_3$-alkyleneoxy group, and especially an ethyleneoxy group;
the linear, partly cyclic or branched $C_1$-$C_{10}$-alkylenethio group is preferably a $C_1$-$C_3$-alkylenethio group, and especially an ethylenethio group;
the linear, partly cyclic or branched $C_1$-$C_{10}$-alkylene-$NR^2$ group is preferably a $C_1$-$C_3$-alkylene-$NR^2$ group, and especially an ethylene-$NR^2$ group;
the $C_6$-$C_{14}$-aryleneoxy group is preferably a $C_6$-$C_{10}$-aryleneoxy group, and especially a 2-phenyleneoxy group;
the perfluorinated $C_6$-$C_{14}$-aryleneoxy group is preferably a perfluorinated $C_6$-$C_{10}$-aryleneoxy group, and especially a tetrafluorophenyl-2-eneoxy group;
the part-fluorinated $C_6$-$C_{14}$-aryleneoxy group is preferably a part-fluorinated $C_6$-$C_{10}$-aryleneoxy group, and especially a fluorophenyl-2-eneoxy group;
the perchlorinated $C_6$-$C_{14}$-aryleneoxy group is preferably a perchlorinated $C_6$-$C_{10}$-aryleneoxy group, and especially a tetrachlorophenyl-2-eneoxy group;
the part-chlorinated $C_6$-$C_{14}$-aryleneoxy group is preferably a part-chlorinated $C_6$-$C_{10}$-aryleneoxy group, and especially a chlorophenyl-2-eneoxy group;
the perbrominated $C_6$-$C_{14}$-aryleneoxy group is preferably a perbrominated $C_6$-$C_{10}$-aryleneoxy group, and especially a tetrabromophenyl-2-eneoxy group;
the part-brominated $C_6$-$C_{14}$-aryleneoxy group is preferably a part-brominated $C_6$-$C_{10}$-aryleneoxy group, and especially a bromophenyl-2-eneoxy group;
the $C_6$-$C_{14}$-arylenethio group is preferably a $C_6$-$C_{10}$-arylenethio group, and especially a 2-phenylenethio group;
the perfluorinated $C_6$-$C_{14}$-arylenethio group is preferably a perfluorinated $C_6$-$C_{10}$-arylenethio group, and especially a tetrafluorophenyl-2-enethio group;
the part-fluorinated $C_6$-$C_{14}$-arylenethio group is preferably a part-fluorinated $C_6$-$C_{10}$-arylenethio group, and especially a fluorophenyl-2-enethio group;
the perbrominated $C_6$-$C_{14}$-arylenethio group is preferably a perbrominated $C_6$-$C_{10}$-arylenethio group, and especially a tetrabromophenyl-2-enethio group;
the part-brominated $C_6$-$C_{14}$-arylenethio group is preferably a part-brominated $C_6$-$C_{10}$-arylenethio group, and especially a bromophenyl-2-enethio group;

the perchlorinated $C_6$-$C_{14}$-arylenethio group is preferably a perchlorinated $C_6$-$C_{10}$-arylenethio group, and especially a tetrachlorophenyl-2-enethio group;

the part-chlorinated $C_6$-$C_{14}$-arylenethio group is preferably a part-chlorinated $C_6$-$C_{10}$-arylenethio group, and especially a chlorophenyl-2-enethio group;

the $C_6$-$C_{14}$-arylene-$NR^2$ group is preferably a $C_6$-$C_{10}$-arylene-$NR^2$ group, and especially an N-methylphenyl-2-ene or N-ethylphenyl-2-ene group;

the perfluorinated $C_6$-$C_{14}$-arylene-$NR^2$ group is preferably a perfluorinated $C_6$-$C_{10}$-arylene-$NR^2$ group, and especially an N-methyltetrafluorophenyl-2-ene or N-ethyltetrafluorophenyl-2-ene group;

the part-fluorinated $C_6$-$C_{14}$-arylene-$NR^2$ group is preferably a part-fluorinated $C_6$-$C_{10}$-arylene-$NR^2$ group, and especially an N-methylfluorophenyl-2-ene or N-ethylfluorophenyl-2-ene group;

the perchlorinated $C_6$-$C_{14}$-arylene-$NR^2$ group is preferably a perchlorinated $C_6$-$C_{10}$-arylene-$NR^2$ group, and especially an N-methyltetrachlorophenyl-2-ene or N-ethyltetrachlorophenyl-2-ene group;

the part-chlorinated $C_6$-$C_{14}$-arylene-$NR^2$ group is preferably a part-chlorinated $C_6$-$C_{10}$-arylene-$NR^2$ group, and especially an N-methylchlorophenyl-2-ene or N-ethylchlorophenyl-2-ene group;

the perbrominated $C_6$-$C_{14}$-arylene-$NR^2$ group is preferably a perbrominated $C_6$-$C_{10}$-arylene-$NR^2$ group, and especially an N-methyltetrabromophenyl-2-ene or N-ethyltetrabromophenyl-2-ene group;

the part-brominated $C_6$-$C_{14}$-arylene-$NR^2$ group is preferably a part-brominated $C_6$-$C_{10}$-arylene-$NR^2$ group, and especially an N-methylbromophenyl-2-ene or N-ethylbromophenyl-2-ene group;

the $C_6$-$C_{14}$-arylene-$PR^2$ group is preferably a $C_6$-$C_{10}$-arylene-$PR^2$ group, and especially a P-methylphenyl-2-ene, P-phenylphenyl-2-ene or P-ethylphenyl-2-ene group;

the perfluorinated $C_6$-$C_{14}$-arylene-$PR^2$ group is preferably a perfluorinated $C_6$-$C_{10}$-arylene-$PR^2$ group, and especially a P-methyltetrafluorophenyl-2-ene, perfluoro-P-phenylphenyl-2-ene or P-ethyltetrafluorophenyl-2-ene group;

the part-fluorinated $C_6$-$C_{14}$-arylene-$PR^2$ group is preferably a part-fluorinated $C_6$-$C_{10}$-arylene-$PR^2$ group, and especially a P-methylfluorophenyl-2-ene or P-ethylfluorophenyl-2-ene group;

the perchlorinated $C_6$-$C_{14}$-arylene-$PR^2$ group is preferably a perchlorinated $C_6$-$C_{10}$-arylene-$PR^2$ group, and especially a P-methyltetrachlorophenyl-2-ene or P-ethyltetrachlorophenyl-2-ene group;

the part-chlorinated $C_6$-$C_{14}$-arylene-$PR^2$ group is preferably a part-chlorinated $C_6$-$C_{10}$-arylene-$PR^2$ group, and especially a P-methylchlorophenyl-2-ene or P-ethylchlorophenyl-2-ene group;

the perbrominated $C_6$-$C_{14}$-arylene-$PR^2$ group is preferably a perbrominated $C_6$-$C_{10}$-arylene-$PR^2$ group, and especially a P-methyltetrabromophenyl-2-ene or P-ethyltetrabromophenyl-2-ene group;

the part-brominated $C_6$-$C_{14}$-arylene-$PR^2$ group is preferably a part-brominated $C_6$-$C_{10}$-arylene-$PR^2$ group, and especially a P-methylbromophenyl-2-ene or P-ethylbromophenyl-2-ene group.

The task of the substituents $R^1$, $R^{1'}$ in the context of the carbene complexes described here is to provide a metal alkylidene which on the one hand is stable but on the other hand still has adequate metathesis activity. Particularly suitable substituents $R^1$, $R^{1'}$ are therefore, as well as $R^{1'}$=H, large alkyl or aryl radicals that assure good steric shielding of the metal alkylidene. Accordingly, it is preferable when $R^1$ is not a hydrogen atom. Particularly appropriately, the carbon atom in $R^1$ directly adjacent to the metal alkylidene is a quaternary carbon atom having no hydrogen substituents. Possible substituents for this quaternary carbon atom include the radicals detailed for the substituents $R^2$. On the basis of these provisions, a suitable substituent $R^1$ can be selected by the person skilled in the art. It has especially been found to be advantageous when $R^1$ in the formulae I to IV is t-butyl, an unsubstituted or substituted phenyl, such as 2-(2-propoxy)phen-1-yl, 2-methoxyphen-1-yl, 2,4,5-trimethoxyphenyl, or ferrocenyl or $CMe_2Ph$, where the substituents on the phenyl may have the same definition as $R^2$, but may especially be 2-(2-propoxy) or 2-methoxy. In addition, it has been found to be advantageous when the $C_1$-$C_{18}$-alkyl group used is a $C_1$-$C_{10}$-alkyl group, and the $C_6$-$C_{14}$-aryl group used is a $C_6$-$C_{10}$-aryl group.

In a preferred embodiment, the N-heterocyclic carbene complex is an N-heterocyclic carbene complex of the general formula V or VI

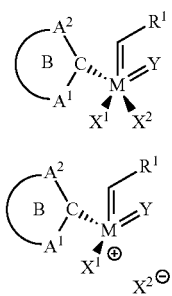

which is characterized in that $A^1$ is $NR^2$ and $A^2$ is $NR^2$ or S, C is a carbenoid carbon atom, the ring B is a 5- to 7-membered ring which, as well as A and $A^2$, may contain further heteroatoms in the form of nitrogen or sulfur, the substituent $R^2$ is a linear or branched $C_1$-$C_{10}$-alkyl, a linear or branched $C_2$-$C_{10}$-alkenyl, especially a $C_3$-$C_6$-cycloalkyl, a linear or branched $C_6$-$C_{10}$-polyoxaalkyl, a $C_5$-$C_{10}$-aryl or a $C_5$-$C_{10}$-heteroaryl radical, a $C_5$-$C_{10}$-aryloxy, a linear or branched $C_1$-$C_{10}$-perfluoroalkyl, a linear or branched $C_1$-$C_{10}$-perchloroalkyl, a linear or branched, part-fluorinated $C_1$-$C_{10}$-alkyl, a linear or branched, part-chlorinated $C_1$-$C_{10}$-alkyl, a perfluorinated $C_5$-$C_{10}$-aryl, a part-fluorinated $C_5$-$C_{10}$-aryl, a perchlorinated $C_5$-$C_{10}$-aryl or part-chlorinated $C_5$-$C_{10}$-aryl radical, and, when $A^1$ and $A^2$ are each $NR^2$, they are the same or different, M in the formulae V and VI is Cr, Mo or W, $X^1$ and $X^2$ in formulae V and VI are the same or different and are selected from the group comprising $C_1$-$C_{18}$ carboxylates, $C_1$-$C_{18}$-alkoxides, $C_1$-$C_{18}$ mono- or polyhalogenated carboxylates, mono- or polysubstituted $C_6$-$C_8$ mono-, bi- or terphenoxides, trifluoromethanesulfonate, tetrafluoroborate, hexafluorophosphate and hexafluoroantimonate, where the substituents on the mono-, bi- or terphenoxides, in addition to halogen, may have the same definition as $R^2$, Y in the formulae V and VI is an oxo group, an N-adamantyl or an N-aryl radical, where the aryl radical may be mono- or polysubstituted by halogen, a $C_1$-$C_{10}$-alkyl, $C_1$-$C_{10}$-alkyloxy or phenyl radical, and $R^1$ in the formulae I and II is an aliphatic or aromatic radical preferably having 4 to about 20 carbon atoms.

For preferred embodiments of the substituents $R^1$, $R^2$, $A^1$, $A^2$, $X^1$, $X^2$ and Y in the formulae V and VI, the above remarks apply analogously.

The carbene complexes of the invention may, in addition to the substituents shown in the formulae I to IV, or V or VI, have one or more uncharged ligands coordinated to the metal center. The function of these uncharged ligands is to increase the coordinative satisfaction of the metal center and to stabilize the metal complex. These ligands are electron donors and are labile, meaning that they can be dissociated from the metal center and replaced by substrate. Suitable ligands are, for example, 1,2-dimethoxyethane, tetrahydrofuran, acetonitrile, phosphines such as triphenylphosphine, tri-n-butylphosphine or trimethylphosphine, and phosphites, for example trimethyl or triethyl or triphenyl phosphite.

The above-described carbene complexes of the invention can be used in solution as catalyst, but it is also possible to immobilize the complexes on a solid support, for example with the aid of a spacer group. The spacer group between the support material and the ring B serves to fix the metal complexes on the solid support. The spacer group advantageously has to be such that the metal complex has a sufficient distance from the support, so as to ensure good accessibility for substrates. The spacer group contains two functional groups by which attachment firstly to the catalyst and secondly to the support is possible. The distance between support and catalyst, by contrast, should not be so great that bimetallic reactions between two immobilized metal complexes can take place. Moreover, the spacer group should be such that it can be joined by means of simple chemical reactions either to the support or to the ring B, or to the metal center. In principle, all aliphatic or aromatic α,ω-difunctional compounds are useful here.

Suitable solid supports in this context especially include polymeric supports, such as those based on polystyrene/poly (divinylbenzene) (PS-DVB), crosslinked poly(methacrylate)s, crosslinked poly(acrylamide)s, but also crosslinked poly(norbornene)s. The support has the task of enabling the binding of the catalyst, and hence a heterogeneous reaction regime. For this purpose, the support appropriately has a mean particle size in the range of 2-1000 micrometers, preferably in the range of 20-200 micrometers, more preferably in the range of 40-60 micrometers, and may be porous or nonporous.

The spacer group used in this case may appropriately be a $C_1$-$C_{20}$-alkyleneoxy group, $C_1$-$C_{20}$-α,ω-dioxoalkylene group, a $C_1$-$C_{20}$-α,ω-diaminoalkylene group, a $C_1$-$C_{20}$-α,ω-dicarboxylalkylene group, a $C_6$-$C_{18}$-dioxoarylene group, a $C_6$-$C_{18}$-diaminoarylene group or a dicarboxy-$C_6$-$C_{18}$-arylene group.

When the spacer group binds directly to the metal center, it may replace an X substituent on the metal in the formulae I-III. Alternatively, the spacer group in the formulae III-IV may also be joined to a P- or N-containing Z group. Examples of suitable spacer groups in this context are:
 a linear, partly cyclic or branched aliphatic α,ω-difunctional $C_1$-$C_{20}$-alkylene group, especially a linear, partly cyclic or branched aliphatic α,ω-difunctional $C_1$-$C_{10}$-alkylene group, where the two functional groups may be the same or different and are in the form of OH, NR'H, COOH, SH, $SO_3H$, $SO_2H$, $PO_3H$, $PO_2H$, Si(OR')OO, Si(OR')$_2$O. R' in this case may have any of the meanings given above for $R^2$, and may especially take the form of N-methylpropargyl acid, where the respective functional groups are formally in the deprotonated (anionic) form.
 a difunctional halogenated or nonhalogenated $C_6$-$C_{14}$ aromatic group, preferably a difunctional halogenated or nonhalogenated $C_6$-$C_{10}$ aromatic group, where the two functional groups may be the same or different and are in the form of OH, NR'H, COOH, SH, $SO_3H$, $SO_2H$, $PO_3H$, $PO_2H$, Si(OR')OO, Si(OR')$_2$O. R' in this case may have any of the meanings given above for $R^2$, and may especially take the form of p-aminophenol, p-aminosulfonic acid, perfluoroaminosulfonic acid, where the respective functional groups are formally in the deprotonated (anionic) form.

In an alternative embodiment, the solid support may also be an inorganic support, for example a support based on glass, silicon dioxide, zirconium oxide or titanium dioxide. Inorganic supports have the advantage of not swelling in the presence of solvents and are thus pressure-stable support materials which in turn can be used advantageously for continuous heterogeneous reaction regimes. In this case, the spacer group used may appropriately be an amino-, hydroxy-, carboxy- or thionyl-alkylene-Si(O)$_3$, an amino-, hydroxy-, carboxy- or thionyl-alkylene-SiR(O)$_2$ group or an amino-, hydroxy-, carboxy- or thionyl-alkylene-SiRR'O group, in which useful substituents for the R and R' radicals are the same as those mentioned above for the substituent $R^2$.

The covalent attachment of the ring B to the support can be effected using an appropriate precursor, for example the protonated form of the ring B (the ring is protonated on the carbene carbon atom) or the alkoxy- or $CO_2$-protected ring B which can be prepared with the aid of one of the methods described in the literature (e.g. *Adv. Synth. Catal.* 2006, 348, 2101; *Adv. Synth. Catal.* 2010, 352, 917; *Chem. Eur. J.* 2013, 19, 11661; *Adv. Synth. Catal.* 2002, 344, 712; *Macromol. Rapid. Commun.* 2004, 25, 231). The carbene in the ring B is then generated by, for example, the addition of a base composed of the protonated form of the ring B, or thermally by detachment of $CO_2$, for example, from the $CO_2$-protected ring B, and reacted with compounds of the general formula M(Y)(CR$^1$R$^1$')X$^1$X$^2$.L$_x$ in which $R^1$, $R^2$, $X^1$ and $X^2$ have the definitions given above, L=a neutral ligand and x may assume a value of 0 to 2. The N-heterocyclic carbene complexes of the formulae I to IV may, depending on the solvent and its composition, be in the uncharged form identified by the formula I or III or in the ionic form identified by the formula II or IV.

A further aspect of the present invention is concerned, as already indicated above, with the use of the inventive carbene complexes of the formulae I to IV as catalyst in olefin metathesis reactions and the polymerization of alkynes or cyclopolymerization of diynes. These olefin metathesis reactions may all be (asymmetric and desymmetrizing) olefin metathesis reactions catalyzable by means of Schrock carbene complexes, especially ring-closing metatheses, cross-metatheses, olefinolyses of unsaturated compounds, such as, more particularly, the ethenolysis of naturally occurring vegetable oils and fats, ring-opening cross-metatheses, (cross-)ene-yne metatheses, ring-closing ene-yne metatheses, cross-ene-diyne metatheses and tandem ring-opening-ring-closing metatheses. It is thus possible to obtain compounds that are of great significance, for example, for the pharmaceutical, agrochemical, polymer, fragrance or flavoring industry. In addition, they can be used for ring-opening metathesis polymerizations (ROMP), 1-alkyne polymerizations, acyclic metathesis polymerizations (ADMET) or cyclopolymerizations of α,ω-diynes. The polymers prepared in this way can be used, for example, as matrix polymers for fiber-matrix composites, as compatibilizers or as base polymer for fibers.

Useful substrates for these olefin metathesis reactions in principle include all substrates amenable to these types of metathesis reactions. For example, it is possible to employ cyclic olefins such as norborn-2-enes, norbornadienes, cyclooctenes, cyclooctadienes, cyclooctatetraenes and/or cyclopentenes, but also alkynes such as acetylene or 2-butyne. This list is not intended to be limiting. For instance, the following cyclic olefins are also possible substrates: cyclopropenes, cyclobutenes, dicyclopentadienes and cyclohexenes. These cyclic olefins may be mono- or polysubstituted. In addition, it is possible to convert olefins, for example ethylene, propylene and substituted butenes, pentenes, hexenes, heptenes, octenes and/or styrenes, and dienes such as 1,3-butadiene, pentadienes, hexadienes, heptadienes and octadienes, within the scope of the olefin metathesis reactions described. Substrates for the olefinolysis, and especially for the ethenolysis, of naturally occurring vegetable oils and fats are generally fatty acid esters and especially castor oil, palm oil or coconut oil in combination with, for example, ethylene or butene.

A particular advantage of the inventive carbene complexes of the formulae I to IV is that they have been found to be particularly tolerant with respect to functional groups. Particular emphasis should be given here to tolerance with respect to alcohols, carboxylic acids, thioethers, amines and aldehydes. Thus, olefin metathesis reactions of functionalized olefins are directly possible, especially in the form of, for example, 5,6-bis((pentyloxy)methyl)bicyclo[2.2.1]hept-2-ene, 7-oxabicyclo[2.2.1]hept-5-ene-2,3-diyl bis-(methylene)diacetate, 4,4,5,5-tetrakis(ethoxycarbonyl)-1,7-octadiyne, 2,2-di(prop-2-yn-1-yl)propane-1,3-diol, diallyldiphenylsilane, 2-(N-cyclohexyl-methyl)norborn-5-ene, 2-(N,N-dimethylaminomethyl)-norborn-5-ene), 1,7-octadiyne-4,5-dicarboxylic acid, 1,6-heptadiyne-4-carboxylic acid, norborn-5-ene-2-carbaldehyde, 4,4-dicyano-1,6-heptadiyne.

A further advantage of the inventive carbene complexes of the formulae I to IV is that they allow very high turnover numbers in some metathesis reactions. Furthermore, in the cyclopolymerization of diynes with carbene complexes of the formulae I to IV, very high stereo- and regioselectivities are observed. Moreover, for example, in the case of homometatheses with carbene complexes of the formulae I to IV having small N-heterocyclic carbenes and large phenoxides, high Z selectivities are achieved.

A particular advantage in the context of the present invention has been found to be that the inventive carbene complexes of the formula II or IV, by virtue of suitable choice of solvent and their composition, are in ionic form. This allows performance of the olefin metathesis reactions under biphasic conditions, which is advantageous in terms of a low metal content of the products prepared.

The performance of olefin metathesis reactions under biphasic conditions is appropriately effected by dissolving the ionic carbene complexes of the formula II or IV in an organic solvent I or in an ionic liquid. In addition to use in conventional biphasic (liquid-liquid) reactions, this solution can be applied to a support material in the form of a film, which can be very thin and preferably has a thickness of 0.05 to 200 μm, especially 0.5 to 10 μm, and can be introduced together with the support into a reaction vessel such as a reaction column. Subsequently, the support coated with the catalyst solution can be contacted with one or more substrates which have optionally themselves been dissolved in a solvent II which is immiscible with the solvent I or the ionic liquid for the compound of the formula II or IV. If no solvent II is employed, the substrates and the products formed within the particular reaction must only have low miscibility with the solvent I or the ionic liquid. Thus, the maximum solubility of the solvent II or of the substrates, but also of the products in the solvent I or in the ionic liquid, should be <10% by volume. The solvent II for the substrates or the substrates themselves in this case have dissolution properties of maximum unfavorability for the catalyst compound, in order that it cannot dissolve in a substantial amount in the substrate solvent.

The reaction vessel is usefully, but not necessarily, a reaction column having an inlet for the substrate solution and an outlet at the opposite end of the reaction column. The above reaction regime is also referred to in the art as "supported ionic liquid phase" (SILP) methodology (see *Topics in Catalysis,* 2006, 40, 91).

Organic solvents I used for the carbene complexes of the formula II or IV may especially be polar aprotic solvents, for example dimethylformamide, dimethylacetamide or dimethyl sulfoxide.

Suitable ionic liquids in connection with the present invention are especially compounds of the general formula $[Q^+]_n [Z]^{n-}$ where the cation $[Q^+]_n$ is a quaternary ammonium $[R^1R^2R^3R^4N^+]$, phosphonium $[R^1R^2R^3R^4P^+]$ or sulfonium $[R^1R^2R^3S^+]$ cation or an analogous quaternized nitrogen, phosphorus or sulfur heteroaromatic of the following formulae:

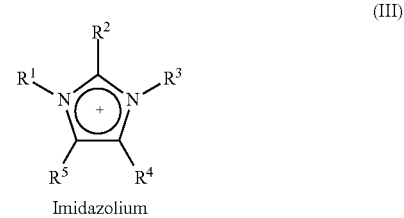

(III)

Imidazolium

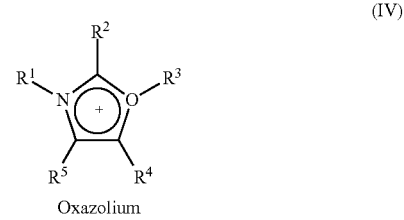

(IV)

Oxazolium

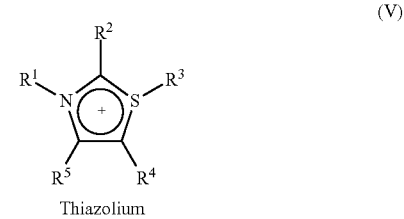

(V)

Thiazolium

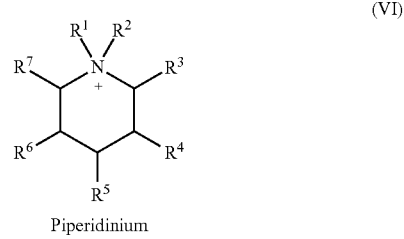

(VI)

Piperidinium

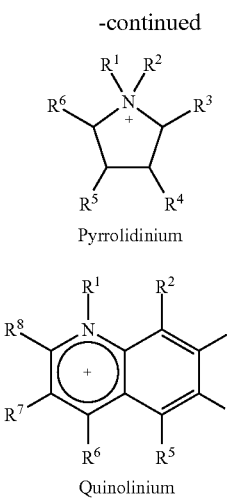

(VII) Pyrrolidinium (VIII) Quinolinium and the $R^1$, $R^2$, $R^3$, $R^4$ radicals and the $R^1$ to $R^8$ radicals in the formulae (III) to (VIII) are independently linear, cyclic, branched, saturated or unsaturated alkyl radicals, mono- or polycyclic, aromatic or heteroaromatic radicals, or derivatives of these radicals substituted by further functional groups. These $R^1$, $R^2$, $R^3$ and $R^4$ radicals may be joined to one another. The anion $[Z]^{n-}$ is preferably in the form of a carboxylate, halide, pseudohalide or amide, or in the form of boron, phosphorus or nitro compounds.

Particularly suitable ionic liquids are especially imidazolium salts, more preferably selected from the group comprising 1-ethyl-3-methylimidazolium salts, 1,3-dimethylimidazolium salts, 1,2,3-trimethylimidazolium salts, 1-butyl-3-methylimidazolium salts and 1-butyl-2,3-dimethylimidazolium salts.

The solvent II which is immiscible with the solvent I or the ionic liquid for the compound of the formula II or IV is preferably an aliphatic or aromatic hydrocarbon, especially toluene, xylene, pentane, hexane, heptane, octane, trichlorobenzene or chlorobenzene or mixtures thereof. In combination with the ionic complexes of formulae II and IV, it is thus assured that these complexes will not dissolve in the solvent II, and hence leaching of the catalyst in a continuous reaction regime is prevented.

Suitable support materials for the solution films of the carbene complexes of the formula II or IV in the context of SILP methodology are particularly inorganic support materials, especially based on glass, zirconium oxide, titanium dioxide, silicon dioxide, or polymer-organic support materials, especially in the form of polymer-organic monolithic support materials, for example based on poly(styrene)/poly(divinylbenzene), poly(methacrylate)s, poly(acrylamide)s or crosslinked poly(norbornene)s or poly(cyclooctene)s. These support materials have the advantage of swelling only slightly, if at all, and hence not causing high backpressures in a continuous reaction regime. A continuous conversion of the substrates is advantageous because one or more substrates are passed continuously into the reaction vessel and the resulting reaction products are removed continuously therefrom, which can lead in turn to higher turnover numbers. In this way, it is possible to conduct olefin metathesis reactions under continuous biphasic conditions (see *Chem. Eur. J.* 2012, 18, 14069).

The aforementioned specifications relating to the conversion of substrates with carbene complexes of the formula II or IV which are dissolved in an organic solvent or in an ionic liquid and applied to a suitable support material in the form of a film likewise relate to corresponding uses of these compounds and methods which are conducted according to these specifications.

The carbene complexes of the formulae I to IV have a desirably high reactivity in olefin metathesis reactions, 1-alkyne polymerization and the cyclopolymerization of diynes, and have a significantly improved tolerance with respect to functional groups over existing group VI metal alkylidene complexes. For example, representatives of the inventive N-heterocyclic carbene complexes of one of the formulae I to IV are stable in the presence of aldehydes, secondary amines, carboxylic acids, nitriles and alcohols. Because of this distinct increase in functional tolerance compared to known Schrock carbene complexes of group VI metals, the spectrum of use in olefin metathesis reactions is distinctly broadened.

The invention is to be elucidated in detail hereinafter with reference to examples. Some general observations are given at the outset:

Unless stated otherwise, all reaction steps were conducted in the absence of oxygen and moisture under $N_2$ or Ar, either by means of Schlenk methodology or in protective gas boxes (MBraun LabMaster 130) in dry glass apparatus. The deuterated solvent $CD_2Cl_2$ was dried over $P_2O_5$ and transferred under vacuum; benzene was dried and distilled over Na. Toluene, diethyl ether, THF and $CH_2Cl_2$ were purified by means of a solvent purification system (SPS, MBraun). Commercially available reagents and the $d_6$-DMSO and $CDCl_3$ used were used without further purification.

The NMR spectra were recorded at 20° C. with the aid of a Bruker 400 spectrometer (400 MHz for proton, 101 MHz for carbon and 376 MHz for fluorine), residual signals calibrated to the internal solvents. The shifts of the signals are reported in ppm. The IR spectra were recorded on a Bruker Vector 22 by means of ATR methodology. The molar masses and molar mass distributions were recorded by means of high-temperature gel permeation chromatography (HT-GPC) on three consecutive Waters Styragel HR4 4.6× 300 mm columns in trichlorobenzene at 145° C. on a PSS HAT-GPC system. The flow rate was 1 mL/min. Narrow-distribution polystyrene standards in the range of $162 < M_n < 6$ 035 000 g·mol$^{-1}$ (EasiVial red, yellow and green) from Polymer Laboratories were employed.

Examples 1 to 16, 34 to 36 and 38 to 53 described hereinafter relate to the preparation of carbene complexes of the formulae I to IV, while the further examples 17 to 33, 37 and 55 to 57 are concerned with olefin metathesis reactions with the aid of the carbene complexes of the invention.

EXAMPLES

1

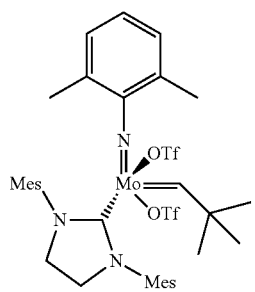

-continued
2
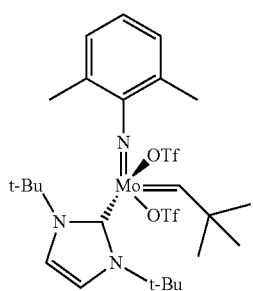
3
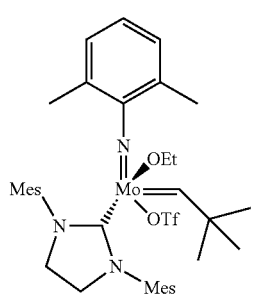
4
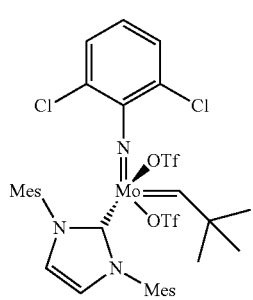
5
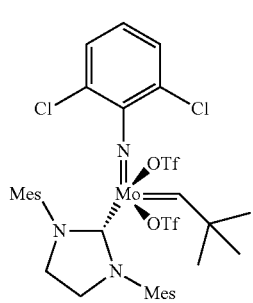
6
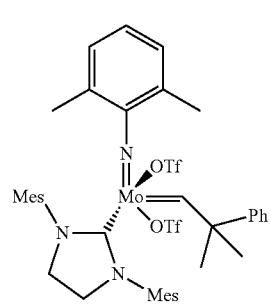
-continued
7
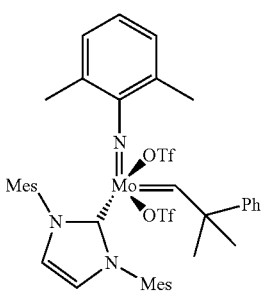
8
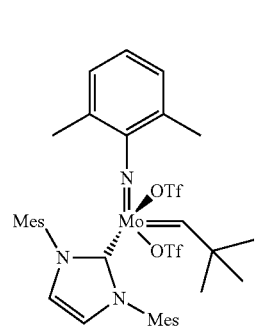
9
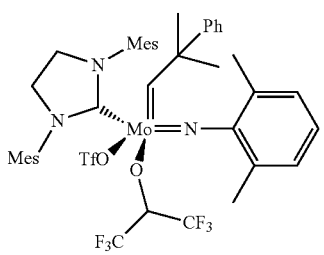
10
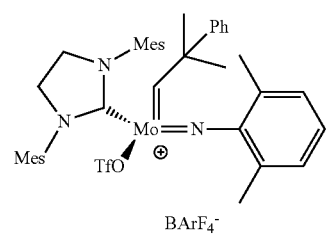
11
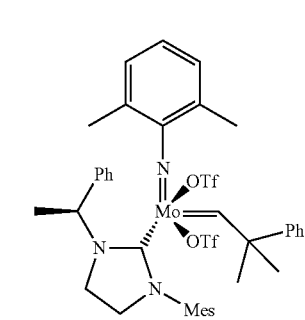

-continued

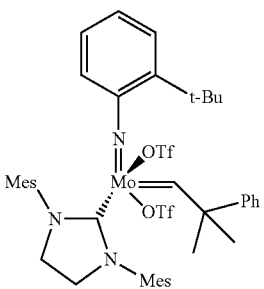

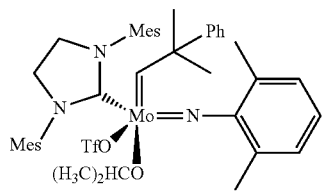

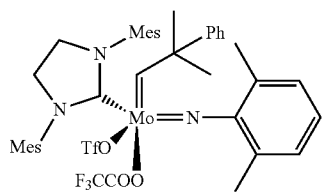

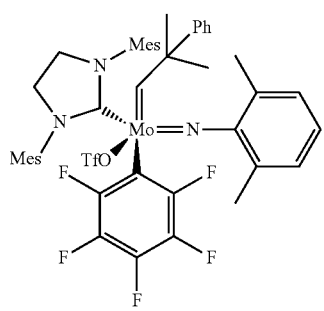

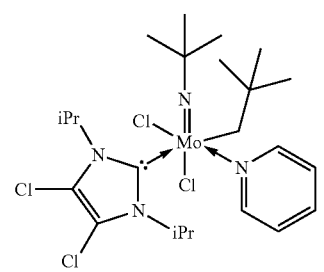

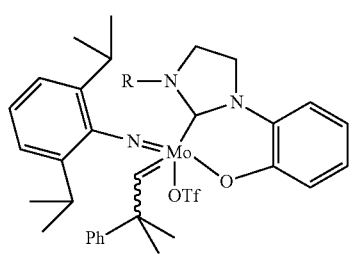

R = DIPP

-continued

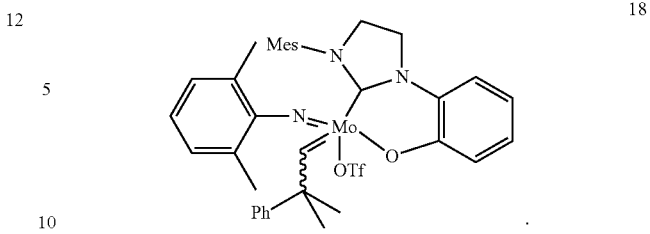

Structure of selected Mo catalysts. DIPP=2,6-di(2-propyl)phen-1-yl.

Example 1 (Preparation of Mo(N-2,6-Me$_2$-C$_6$H$_3$)(IMesH$_2$)(CH-tBu)(OTf)$_2$) (1)

Mo(N-2,6-Me$_2$-C$_6$H$_3$)(CH-tBu)(OTf)$_2$ (DME) (0.300 g, 0.445 mmol) were dissolved in 8 mL of benzene, and a solution of 1,3-bis(2,4,6-trimethylphenyl)-2-imidazolinylidene (0.136 g, 0.445 mmol) in 5 mL of benzene was added. The reaction solution was stirred for three hours, the benzene was decanted off, and the residue was washed with benzene. Yield: 0.32 g (81%, yellow powder). It was possible to obtain crystalline material by recrystallization from CH$_2$Cl$_2$. $^1$H NMR (CD$_2$Cl$_2$): δ (syn isomer, 99.9%) 12.76 (s, 1, CHCMe$_3$, J$_{CH}$=118 Hz), 7.06-6.61 (7H, ArH), 3.98 (4H, CH$_2$NC), 2.69-1.71 (24H, Me), 0.93 (s, 9H, CH$_2$CMe$_3$); $^{19}$F NMR (CD$_2$Cl$_2$): δ −74.65 (SO$_3$CF$_3$), −76.7 (SO$_3$CF$_3$). $^{13}$C NMR (CD$_2$Cl$_2$): δ 320.9 (CH-tBu), 208.7 (CN$_{carbene}$), 154.6 (C$_{ipso}$), 140.4 (C$_{ortho}$), 137.1 (C$_{aryl}$), 136.8 (C$_{aryl}$), 135.7 (C$_{aryl}$), 131.1 (CH$_{aryl}$), 130.5 (CH$_{aryl}$), 130.1 (CH$_{aryl}$), 128.2 (C$_{aryl}$), 120.2 (q, CF$_3$, J=319 Hz), 119.8 (q, CF$_3$, J=320 Hz), 53.1 (CMe$_3$), 50.7 (CH$_{2\text{-}imidazolylene}$), 30.5 (CMe$_3$), 21.3 (CH$_3$), 19.0 (CH$_3$), 18.9 (CH$_3$); anal. calc. for C$_{36}$H$_{45}$F$_6$MoN$_3$O$_6$S$_2$.CH$_2$Cl$_2$: C, 45.54; H, 4.96; N, 4.31. Found: C, 45.52; H, 4.75; N, 4.37.

Example 2 (Preparation of Mo(N-2,6-Me$_2$-C$_6$H$_3$)(I-tBu)(CH-tBu)(OTf)$_2$) (2)

Mo(N-2,6-Me$_2$-C$_6$H$_3$)(CH-tBu)(OTf)$_2$ (DME) (0.100 g, 0.148 mmol) were dissolved in 3 mL of benzene. 1,3-Di-t-butylimidazol-2-ylidene (0.027 g, 0.15 mmol), likewise dissolved in benzene, was added while stirring. After stirring for three hours, the liquid was decanted from the precipitate and the residue was washed with benzene. Yield: 0.060 g (65%, yellow powder). It was possible to obtain crystalline material by recrystallization from CH$_2$Cl$_2$. $^1$H NMR (CD$_2$Cl$_2$): δ 14.60 (s, 1H, CHCMe$_3$, J$_{CH}$=121 Hz, syn isomer), 7.12-6.95 (3H, ArH), 2.60 (2H, CHNC), 1.80-1.67 (24H, Me), 1.32 (s, 9H, CH$_2$CMe$_3$); $^{19}$F NMR (CD$_2$Cl$_2$): δ −77.68, −77.69, −77.70, −77.71 (CF$_3$SO$_3$), −78.06, −78.07, −78.08, −78.09 (CF$_3$SO$_3$); $^{13}$C NMR (CD$_2$Cl$_2$): δ 329.6 (CH-tBu), 175.4 (CN$_{carbene}$), 154.3 (C$_{ipso}$), 142.2 (C$_{aryl}$), 136.9 (C$_{aryl}$), 129.7 (CH$_{aryl}$), 129.6 (CH$_{aryl}$), 128.9 (CH$_{aryl}$), 121.7 (C$_{C=C}$), 120.6 (C$_{C=C}$), 119.8 (q, CF$_3$, J=318 Hz), 119.7 (q, CF$_3$, J=319 Hz), 61.7 (NCMe$_3$), 61.3 (CMe$_3$), 32.8 (CMe$_3$), 30.5 (CMe$_3$), 30.1 (CMe$_3$), 21.1 (CH$_3$), 18.4 (CH$_3$). Anal. calc. for C$_{26}$H$_{39}$F$_6$MoN$_3$O$_6$S$_2$: C, 40.84; H, 5.27; N, 5.50. Found: C, 40.88; H, 5.20; N, 5.56.

Example 3 (Preparation of N-2,6-Me$_2$-C$_6$H$_3$)(IMesH$_2$)—(CHCMe$_3$)(OTf)(OEt)) (3)

Sodium ethoxide (0.0120 g, 0.1842 mmol) was dissolved in 5 mL of diethyl ether:THF, 1:1. Then Mo(N-2,6-Me$_2$-

$C_6H_3$)(IMesH$_2$)(CH-tBu)(OTf)$_2$ (0.080 g, 0.090 mmol) was added. After stirring for two hours, the solvent was removed, and the residue was dissolved in 5 mL of dichloromethane and filtered through Celite. Recrystallization from dichloromethane gave yellow crystalline material in 40% yield. $^1$H NMR (CD$_2$Cl$_2$): δ 12.30 (s, 1H, CHCMe$_3$), 6.94-6.65 (7H, ArH), 4.15 (4H, CH$_2$NC), 3.69 (2H, OCH$_2$CH$_3$), 2.53-2.24 (24H, Me), 1.82 (3H, OCH$_2$CH$_3$), 1.14 (s, 9H, CH$_2$CMe$_3$); 19F NMR (CD$_2$Cl$_2$): δ −79.05 (CF$_3$SO$_3$).

Example 4 (Preparation of Mo(N-2,6-Cl$_2$—C$_6$H$_3$) (CHCMe$_3$)-(OTf)$_2$(IMes)) (4)

In a glovebox, Mo(N-2,6-Cl—C$_6$H$_3$)(CHCMe$_3$)(OTf)$_2$ (DME) (0.432 g, 0.605 mmol) was initially charged in a 25 mL Schlenk flask. The complex was dissolved in 15 mL of toluene and cooled at −40° C. for 30 min. 1,3-Dimesityl-imidazol-2-ylidene (0.184 g, 0.605 mmol, 1 equiv.) was dissolved in 3 mL of toluene and likewise cooled. While stirring, the cold NHC solution was added dropwise to the metal complex. The color changed gradually to dark orange. The reaction mixture was stirred at room temperature for 2 h. After a few minutes, cloudiness set in and a precipitate formed. Subsequently, the solvent was concentrated to about ⅓ and the suspension was frozen for 30 min. The precipitated solids were filtered off and washed with a little cold toluene. The crude product is obtained as a yellow solid and can be recrystallized from dichloromethane (0.450 g, 80%). $^1$H NMR (400 MHz, CD$_2$Cl$_2$): δ=1.12 (s, 9H, tBu), 2.10 (s, 6H, o-Mes-Me), 2.11 (s, 6H, o-Mes-Me), 2.24 (s, 6H, p-Mes-Me), 6.68 (s, br, 2H, Mes-Ar), 6.98 (s, br, 2H, Mes-Ar), 7.14 (m, 3H, Ar), 7.22 (s, 2H, N—CH—CH—N), 12.94 (s, 1H, Mo=CH); $^{13}$C NMR (100 MHz, CD$_2$Cl$_2$): δ=18.9 (o-Mes-$\underline{Me}$), 19.0 (o-Mes-$\underline{Me}$), 21.3 (p-Mes-$\underline{Me}$), 31.4 (C$\underline{Me}_3$), 50.6 ($\underline{C}$Me$_3$), 124.4, 126.4, 128.3, 129.5, 130.3, 130.9, 134.7, 135.9, 136.3, 136.5, 141.0 (ipso-Mes), 149.9 (ipso-imido), 185.2 (N—C—N), 327.4 (Mo=CH, $J_{C-H}$=119.5 Hz); $^{19}$F NMR (375 MHz, CD$_2$Cl$_2$) δ=−75.07, −76.56.

Example 5 ((Preparation of Mo(N-2,6-Cl$_2$—C$_6$H$_3$) (CHCMe$_3$)-(OTf)$_2$(IMesH$_2$)) (5)

In a glovebox, Mo(N-2,6-Cl—C$_6$H$_3$)(CHCMe$_3$)(OTf)$_2$ (DME) (0.198 g, 0.277 mmol) was initially charged in a 25 mL Schlenk flask. The complex was dissolved in 15 mL of toluene and cooled at −40° C. for 30 min. 1,3-Dimesityl-imidazol-2-ylidene (0.085 g, 0.277 mmol, 1 equiv.) was dissolved in 3 mL of toluene and likewise cooled. While stirring, the cold NHC solution was added dropwise to the metal complex. The color changed gradually to dark orange. The reaction mixture was stirred at room temperature for 2 h. After a few minutes, cloudiness set in and a precipitate formed. Subsequently, the solvent was concentrated to about ⅓ and the suspension was frozen for 30 min. The precipitated solids were filtered off and washed with a little cold toluene. The crude product is obtained as a yellow solid and can be recrystallized from dichloromethane (0.185 g, 72%).

Example 6 (Preparation of Mo(N-2,6-Me$_2$-C$_6$H$_3$) (IMesH$_2$)—(CHCMe$_2$Ph)(OTf)$_2$) (6)

Mo(N-2,6-Me$_2$-C$_6$H$_3$)(CHCMe$_2$Ph)(OTf)$_2$(DME) (0.20 g, 0.2720 mmol) was initially charged in 8 mL of benzene: 1,3-bis(2,4,6-trimethylphenyl)-2-imidazolidin-2-ylidene (0.0830 g, 0.2720 mmol) was dissolved in 1 mL of benzene and added dropwise. In the course of this, a rapid color change from a yellow to dark red was observed with simultaneous formation of a precipitate.

After stirring for three hours, the benzene was then decanted off, and the residue was washed with benzene and dried under reduced pressure. The product was isolated as a yellow solid (0.15 g, 81%). Alternatively, the yellow solid can be dissolved in a minimal amount of dichloromethane and crystallized at −30° C. for 24 h, giving a crystalline yellow material with 69% yield. $^1$H NMR (CD$_2$Cl$_2$): δ=13.11 (s, 1H, CHCMe$_2$Ph, $J_{CH}$=114 Hz), 7.19-6.95 (m, 9H, ArH), 6.51 (s, 2H, ArH), 3.97 (s, 4H, CHNC), 2.69-1.71 (s, 27H, Me), 1.25 (s, 3H, CHCMe$_2$Ph) ppm; $^{19}$F NMR (CD$_2$Cl$_2$): δ=−74.59 (s, CF$_3$SO$_3$, trans to the NHC ligand), −76.53 (s, CF$_3$SO$_3$); $^{13}$C NMR (CD$_2$Cl$_2$): δ=317.4 (CHCMe$_3$), 208.7 (CN$_{carbene}$), 154.6 (C$_{ipso}$), 149.0, 140.4 (C$_{ortho}$), 137.0 (C$_{aryl}$), 136.4 (C$_{aryl}$), 135.6 (C$_{aryl}$), 130.9 (C$_{aryl}$), 130.5 (C$_{aryl}$), 130.2 (C$_{aryl}$), 128.4 (C$_{aryl}$), 128.2 (C$_{aryl}$), 126.9 (C$_{aryl}$), 125.9 (C$_{aryl}$), 121.6 (q, CF$_3$, J=319 Hz), 118.5 (q, CF3, J=320 Hz), 56.8 (CMe$_2$Ph), 53.1 (CH$_2$ imidazolylidene), 32.9 (CMe$_2$Ph), 29.6 (CMe$_2$Ph), 21.3 (CH$_3$), 19.0 (CH$_3$), 18.9 (CH$_3$); elemental analysis: C$_{41}$H$_{47}$F$_6$MoN$_3$O$_6$S$_2$; calculated: C, 51.68; H, 5.02; N, 4.41. found: C, 51.81; H, 4.88; N, 4.35.

Example 7 (Preparation of Mo(N-2,6-Me$_2$-C$_6$H$_3$) (IMes)-(CHCMe$_2$Ph)(OTf)$_2$) (7)

Mo(N-2,6-Me$_2$-C$_6$H$_3$)(CHCMe$_2$Ph)(OTf)$_2$(DME) (0.1500 g, 0.204 mmol) was dissolved in 6 mL of benzene, adding to the initially charged solution of 1,3-bis(2,4,6-trimethylphenyl)-2-imidazol-2-ylidene (0.0620 g, 0.2040 mmol) in a 1 mL of benzene. The color changed immediately from yellow to dark red with simultaneous formation of a precipitate. The reaction mixture was stirred for three hours and then the solvent was decanted. The residue was washed with benzene and dried under reduced pressure. A yellow solid was obtained (0.13 g, 85%). The yellow product can be recrystallized from a minimal amount of dichloromethane at −30° C. (65%). $^1$H NMR (CD$_2$Cl$_2$): δ=13.18 (s, 1H, CHCMe$_2$Ph, $J_{CH}$=118 Hz), 7.21-6.95 (m, 9H, ArH), 6.56 (s, 2H), 4.29 (s, 2H, CHNC), 2.60-1.97 (s, 27H, Me), 1.29 (s, 3H, CHCMe$_2$Ph) ppm; $^{19}$F NMR (CD$_2$Cl$_2$): δ=−74.92 (s, CF$_3$SO$_3$, trans to the NHC ligand), −76.53 (s, CF$_3$SO$_3$); $^{13}$C NMR (CD$_2$Cl$_2$): δ=317.0 (CHCMe$_3$), 184.3 (CN$_{carbene}$), 154.8 (C$_{ipso}$), 149.0, 141.3 (C$_{ortho}$), 136.4 (C$_{aryl}$), 135.9 (C$_{aryl}$), 135.5 (C$_{aryl}$), 130.6 (C$_{aryl}$), 130.1 (C$_{aryl}$), 130.0 (C$_{aryl}$), 128.6 (C$_{aryl}$), 128.2 (C$_{aryl}$), 126.9 (C$_{aryl}$), 126.4 (C$_{aryl}$), 125.9 (C$_{aryl}$), 121.6 (C$_{C=C}$), 121.4 (C$_{C=C}$), 118.4 (q, CF$_3$, J=318 Hz), 118.3 (q, CF$_3$, J=319 Hz), 56.8 (CMe$_2$Ph), 33.2 (CMe$_2$Ph), 29.8 (CMe$_2$Ph), 21.4 (CH$_3$), 20.6 (CH$_3$), 18.7 (CH$_3$); elemental analysis: C$_{41}$H$_{45}$F$_6$MoN$_3$O$_6$S$_2$; calculated: C, 51.79; H, 4.88; N, 4.42. found: C, 51.73; H, 4.80; N, 4.39.

The catalyst Mo(N-2,6-Me$_2$-C$_6$H$_3$)(IMeS)(CH-tBu) (OTf)$_2$) (8) was prepared analogously to example 2, except using a corresponding amount of 1,3-bis(2,4,6-trimethylphenyl)-imidazol-2-ylidene rather than 1,3-di-t-butylimidazol-2-ylidene.

Example 8 (Preparation of Mo(N-2,6-Me$_2$-C$_6$H$_3$) (IMesH$_2$)—(CHCMe$_2$Ph)(OTf)(OCH(CF$_3$)$_2$)) (9)

Mo(N-2,6-Me$_2$-C$_6$H$_3$)(CHCMe$_2$Ph)(OTf)$_2$(DME) (0.0400 g, 0.0420 mmol) was dissolved in a minimal amount (~2 mL) of C$_2$H$_4$Cl$_2$, the solution was cooled to −30° C. and then LiOCH(CF$_3$)$_2$ (0.0050 g, 0.0420 mmol) was added. The reaction mixture was stirred at room temperature for two hours and then filtered through Celite. After the solvent had been removed under reduced pressure, a yellow solid was obtained. The residue was dissolved in a minimal amount of dichloromethane and crystallized at −30° C. for several days, in order to obtain yellow crystals (63%). $^1$H NMR (CD$_2$Cl$_2$): δ=13.49 (s, 1H, CHCMe$_2$Ph, J$_{CH}$=114 Hz), 7.28-6.41 (m, 14H, ArH), 3.97-3.82 (m, 4H, CH$_2$NC), 2.32-1.79 (s, 30H, Me); $^{13}$C NMR (CD$_2$Cl$_2$): δ 323.8 (CHCMe$_3$), 210.0 (CN$_{carbene}$), 155.2 (C$_{ipso}$), 150.7, 139.5 (C$_{ortho}$) r, 136.9 (C$_{aryl}$), 135.8 (C$_{aryl}$), 135.2 (C$_{aryl}$), 130.1 (C$_{aryl}$), 129.9 (C$_{aryl}$), 129.1 (C$_{aryl}$), 128.6 (C$_{aryl}$), 127.8 (C$_{aryl}$), 126.6 (C$_{aryl}$), 125.8 (C$_{aryl}$), 121.6 (CF$_3$), 118.4 (q, CF$_3$), 76.07-75.11 (q, OCH(CF$_3$)$_2$), 56.1 (CMe$_2$Ph), 51.9 (CH$_{2\text{-}imidazolylidene}$), 37.2 (CMe$_2$Ph), 29.3 (CMe$_2$Ph), 21.5 (CH$_3$), 21.3 (CH$_3$), 19.0 (CH$_3$), 18.9 (CH$_3$); $^{19}$F NMR (CD$_2$Cl$_2$): δ=−73.07-73.14 (q, CF$_3$), −77.33-73.40 (q, CF$_3$), −78.07 (s, CF$_3$SO$_3$, trans to the NHC ligand). Elemental analysis: C$_{44}$H$_{50}$Cl$_2$F$_9$MoN$_3$O$_4$S; calculated: C, 50.05; H, 4.87; N, 3.98. found: C, 50.51; H, 4.85; N, 4.07.

Example 9 ((Preparation of [Mo(N-2,6-Me$_2$-C$_6$H$_3$)—(CHCMe$_2$Ph)(OTf)(IMesH$_2$)$^+$ B(3,5-(CF$_3$)$_2$—C$_6$H$_3$)$_4$$^−$]) (10)

[Ag$^+$ B(3,5-(CF$_3$)$_2$—C$_6$H$_3$)$_4$] (0.0874 g, 0.0879 mmol) was dissolved in 1 mL of C$_2$H$_4$Cl$_2$ and added at −30° C. to a solution of Mo(N-2,6-Me$_2$-C$_6$H$_3$)(CHCMe$_2$Ph)(OTf)(DME) (0.08370 g, 0.0879 mmol) in 2 mL of C$_2$H$_4$Cl$_2$. The reaction mixture was stirred overnight, then filtered through Celite, and the solvent was removed under reduced pressure. The yellow residue was taken up in a minimal amount of dichloromethane and stored at −30° C. for several days in order to isolate the product in the form of yellow crystals in a ~60% yield. $^1$H NMR (CD$_2$Cl$_2$): δ=12.90 (s, 1H, CHCMe$_2$Ph, J$_{CH}$=127 Hz), 7.72-6.97 (m, 20H, ArH), 4.06 (s, 4H, CH$_2$NC), 2.37-0.92 (s, 33H, Me); $^{13}$C NMR (CD$_2$Cl$_2$): δ=325.0 (CHCMe$_3$), 206.7 (CN$_{carbene}$), 163.1-162.59 (q, $^1$J$_{B—C}$=50 Hz), 154.0 (C$_{ipso}$), 144.3, 143.2, 142.4, 141.3 (C$_{ortho}$), 137.1 (C$_{aryl}$), 135.4 (C$_{aryl}$), 132.5 (C$_{aryl}$), 131.6 (C$_{ortho}$), 130.6 (C$_{aryl}$), 130.0 (C$_{aryl}$), 129.6 (C$_{aryl}$), 129.2 (C$_{aryl}$), 129.0 (C$_{aryl}$), 128.8 (C$_{aryl}$), 128.6 (C$_{aryl}$), 127.8 (C$_{aryl}$), 126.7 (C$_{aryl}$), 126.3 (C$_{aryl}$), 123.8, 121.1, 118.1, 57.5 (CMe$_2$Ph), 52.8 (CH$_{2\text{-}imidazolylidene}$), 28.8 (CMe$_2$Ph), 21.4 (CH$_3$), 21.3 (CH$_3$), 20.7 (CH$_3$), 19.8 (CH$_3$), 18.7 (CH$_3$), 18.0 (CH$_3$). $^{19}$F NMR (CD$_2$Cl$_2$): δ=−62.89 (s, 3F), −75.66 (s, CF$_3$SO$_3$, trans to the imido ligand).

Example 10 (Preparation of Mo(N-2,6-Me$_2$-C$_6$H$_3$) (3-mesityl-1-(1-phenylethyl)imidazolin-2-ylidene) (CHCMe$_2$Ph)(OTf$_2$)) (11)

3-Mesityl-1-(1-phenylethyl)-4,5-dihydrol-H-imidazol-3-ium tetrafluoroborate (0.0820 g, 0.2160 mmol) was suspended in 2 mL of benzene. KHMDS (0.0430 g, 0.2160 mmol) was added to the suspension while stirring. After a reaction time of one hour, the clear benzene solution was filtered through Celite. Mo(N-2,6-Me$_2$-C$_6$H$_3$)—(CHCMe$_2$Ph)(OTf$_2$)•(DME) (0.1580 g, 0.2160 mmol; J. Organomet. Chem. 1993, 459, 185) was dissolved in 8 mL of benzene and the solution was stirred for 15 minutes. The previously filtered benzene solution of the free NHC was then added thereto, with observation of an immediate color change from yellow to dark red. After stirring for three hours, the benzene was removed, and the yellow residue was washed with n-pentane and dried under reduced pressure (0.0110 g, 85%). The residue was dissolved in a minimal amount of dichloromethane and stored at −30° C. for several days in order to obtain yellow crystals (60%). $^1$H NMR (CD$_2$Cl$_2$): δ=14.73 (s, 1H, CHCMe$_2$Ph), 7.36-6.99 (m, 14H, ArH), 6.29 (s, 1H, Ar-Mes), 4.08-3.80 (m, 4H, CH$_2$NC), 2.46-1.39 (s, 24H, Me); $^{19}$F NMR (CD$_2$Cl$_2$): δ=−77.06 (s, CF$_3$SO$_3$), −77.77 (s, CF$_3$SO$_3$, trans to the NHC ligand); elemental analysis calculated for C$_{41}$H$_{47}$Cl$_2$F$_6$MoN$_3$O$_6$S$_2$; C, 48.14; H, 4.73; N, 4.10. found: C, 48.17; H, 4.68; N, 4.06.

Example 11 (Preparation of Mo(N-2,6-Me$_2$-C$_6$H$_3$) (IMesH$_2$)—(CHCMe$_3$)(OTf)(OCH(CH$_3$)$_2$)) (13)

Mo(N-2,6-Me$_2$-C$_6$H$_3$)(IMesH$_2$)(CHCMe$_3$)(OTf)$_2$ (0.080 g, 0.0900 mmol) was dissolved in a minimal amount (~2 mL) of C$_2$H$_4$Cl$_2$, the solution was cooled to −30° C. and then LiOCH(CH$_3$)$_2$ (0.0050 g, 0.0900 mmol) was added. The reaction mixture was stirred at room temperature for two hours, then filtered through Celite, and the solvent was removed under reduced pressure. The yellow residue was taken up in a minimal amount of dichloromethane and stored at −30° C. for several days in order to isolate the product in the form of yellow crystals in ~63% yield.

The catalyst Mo(N-2,6-Me$_2$-C$_6$H$_3$)(IMesH$_2$)(CHCMe$_3$)(OTf)-(OOCCF$_3$) (14) was prepared analogously to example 11, except using a corresponding amount of lithium trifluoroacetate instead of LiOCH(CH$_3$)$_2$.

Example 12 (Preparation of Mo(N-2,6-Me$_2$-C$_6$H$_3$) (IMesH$_2$)—(CHCMe$_3$)(OTf)(OC$_6$H$_5$)) (15)

Mo(N-2,6-Me$_2$-C$_6$H$_3$)(IMesH$_2$)(CHCMe$_3$)(OTf)$_2$ (0.0300 g, 0.0315 mmol) was dissolved in a minimal amount (~2 mL) of C$_2$H$_4$Cl$_2$, the solution was cooled to −30° C. and then LiOC$_6$F$_5$ (0.0050 g, 0.0315 mmol) was added. The reaction mixture was stirred at room temperature for two hours and then filtered through Celite. After the solvent had been removed under reduced pressure, a yellow solid was obtained. The residue was dissolved in a minimal amount of dichloromethane and stored at −30° C. for several days in order to obtain yellow crystals.

Example 13 (Preparation of Mo(N-2-tBu-C$_6$H$_4$) (IMesH$_2$)—(CHCMe$_2$Ph)(OTf)$_2$) (12)

Mo(N-2-$^t$Bu-C$_6$H$_4$)(CHCMe$_2$Ph)(OTf)$_2$(DME) (0.0320 g, 0.0430 mmol) was first dissolved in 2 mL of toluene. 1,3-Bis(2,4,6-trimethylphenyl)-2-imidazolidin-2-ylidene (0.0130 g, 0.0430 mmol) was dissolved 1 mL of toluene. A color change from yellow to light orange was observed here. After stirring for three hours, the toluene was then removed and the residue was dried under reduced pressure. The product was isolated as a yellow solid.

Example 14 (Preparation of Mo(NtBu)(Cl)$_2$(1,3-iPr$_2$-4,5-Cl$_2$-imidazol-2-ylidene)(pyridine) (CHCMe$_3$)) (16)

Mo(NtBu)(Cl)$_2$(pyridine)$_2$(CHCMe$_3$) (0.036 g, 0.078 mmol) was dissolved in 5 mL of dichloromethane. 1,3-Me$_2$-4,5-Cl$_2$-imidazol-2-ylidene-AgI (0.036 g, 0.36 mmol, 1.0 equiv.) was added in solid form. The suspension was stirred at room temperature for 1 hour. Subsequently, the suspension was filtered through Celite and the solvent was removed. The pale yellow solids were taken up in 4 mL of dichloromethane and filtered once more. The solvent was removed and the solids were washed with n-pentane. The product was obtained as a pale orange solid. Yield: 0.039 g (82%). $^1$H NMR (400 MHz, CD$_2$Cl$_2$): δ=1.55 (s, br, 9H, tBu), 1.67 (s, br, 9H, tBu), 1.71 (d, br, 12H, iPr-Me), 4.98 (m, br, 2H, iPr-CH), 7.56 (m, br, 2H, pyr), 8.02 (m, br, 1H, pyr), 9.21 (m, br, 1H, pyr), 9.86 (m, br, 1H, pyr), 14.38 (s, br, 1H, Mo=CH).

Example 15 (Synthesis of Cat. 17)

31.1 mg (0.076 mmol of 1-(2,6-diisopropylphenyl)-3-(2-hydroxyphenyl)-4,5-dihydroimidazolium tetrafluoroborate and 25.4 mg (0.152 mmol) of LiHMDS were suspended in benzene. After the mixture had been stirred at room temperature for 1 h, the solids were filtered off and the filtrate was added dropwise to a solution of 60 mg (0.076 mmol) of $Mo(N-2,6-C_6H_3{}^iPr_2)(CH_2CMe_2Ph)(OSO_2CF_3)_2(DME)$. The yellow solution darkened somewhat and became slightly cloudy. The mixture was stirred at room temperature for 3 h and then filtered through Celite. The solvent was removed under reduced pressure and the yellow solids obtained were dissolved in a little dichloromethane. Yellow crystals were obtained at −35° C. $^1H$ NMR ($CD_2Cl_2$, 400 MHz) δ=13.64 (s, 1H, CHCMe$_2$Ph, $J_{CH}$=119 Hz); 7.50-7.41 (m, 2H, CH); 7.28-7.18 (m, 5H, CH); 7.17-7.01 (m, 7H, CH); 6.95 (dd, J=7.79, 1.32 Hz; 1H, CH); 4.60-4.47 (m, 1H, CH); 4.38-4.26 (m, 1H, CH); 4.07-3.94 (m, 1H, CH); 3.93-3.80 (m, 1H, CH); 3.72-3.56 (m, 2H, CH); 2.68 (hept, J=6.88 Hz; 1H, CH); 2.51 (hept, J=6.51 Hz; 1H, CH); 1.14 (d, J=6.81 Hz; 6H, CH$_3$); 1.03 (s, 3H, CH$_3$); 0.98 (d, J=6.84 Hz; 3H, CH$_3$); 0.5 (d, J=6.81 Hz; 3H, CH$_3$); 0.84 (d, J=6.86 Hz; 6H, CH$_3$); 0.3 (d, J=6.74 Hz; 3H, CH$_3$); 0.6 (d, J=6.80 Hz; 3H, CH$_3$); 9F NMR ($CD_2Cl_2$) δ=−77.94 ($SO_3CF_3$); $^{13}C$ NMR ($CD_2Cl_2$, 100 MHz) δ=316.9 (CH-Me$_2$Ph), 205.9 ($CN_{carbene}$), 152.2 ($C_{ar.}$), 151.9 ($C_{ar.}$), 149.3 ($C_{ar.}$), 147.4 ($C_{ar.}$), 146.5 ($C_{ar.}$), 145.7 ($C_{ar.}$), 137.2 ($C_{ar.}$), 130.3 ($C_{ar.}$), 129.7 ($C_{ar.}$), 128.5 ($C_{ar.}$), 128.4 ($C_{ar.}$), 126.9 ($C_{ar.}$), 126.7 ($C_{ar.}$), 126.6 ($C_{ar.}$), 126.4 ($C_{ar.}$), 125.3 ($C_{ar.}$), 123.2 ($C_{ar.}$), 120.9 ($C_{ar.}$), 120.6 ($C_{ar.}$), 119.9 (q, CF$_3$, J=319 Hz), 117.5 ($C_{ar.}$), 55.6 ($CH_{2-imidazolylidene}$), 54.9 ($CH_{2-imidazolylidene}$), 49.4 (CMe$_2$Ph), 34.8, 29.7, 28.7, 28.5, 26.6, 26.1, 25.9, 24.3, 23.4, 22.7, 21.5.

Example 16 (Synthesis of Cat. 18)

30.03 mg (0.086 mmol) of 1-(mesityl)-3-(2-hydroxyphenyl)-4,5-dihydroimidazolium tetrafluoroborate and 27.30 mg (0.163 mmol) of LiHMDS were suspended in benzene and stirred at room temperature for 2 h. The LiBF$_4$ formed was filtered off and the filtrate was slowly added dropwise to a solution of 60 mg (0.086 mmol) of $Mo(N-2,6-C_6H_3Me_2)(CH_2CMe_2Ph)(OSO_2CF_3)_2$-(DME) in benzene. The reaction mixture was stirred at room temperature for 3 h and then filtered through Celite. The solvent was removed under reduced pressure and the residue was dissolved in a little dichloromethane. A couple of drops of n-pentane were added and the product was obtained at −35° C. as dark yellow crystals. $^1H$ NMR ($CD_2Cl_2$, 400 MHz) δ=(anti/syn 2:3) 14.46; 12.81 (s, 1H, CHCMe$_2$Ph, $J_{CH}$=147 Hz (anti), 116 Hz (syn)); 7.31-7.13 (m, 7H, CH); 7.11-7.02 (m, 2H, CH); 7.01-6.76 (m, 3H, CH); 6.70; 6.63 (s, br, 1H, CH); 6.14; 6.02 (s, br, 1H, CH); 4.44-4.15 (m, 2H, CH$_2$); 2.30 (s, CH$_3$); 2.22 (s, 3H, CH$_3$); 2.07 (s, 3H, CH$_3$); 2.05 (s, 3H, CH$_3$); 1.98 (s, CH$_3$); 1.84 (s, CH$_3$); 1.70 (s, CH$_3$); 1.69 (s, CH$_3$); 1.57 (s, CH$_3$); 1.44 (s, CH$_3$); 1.38 (s, CH$_3$); 1.30 (s, CH$_3$); $^{19}F$ NMR ($CD_2Cl_2$) δ=−78.13 ($SO_3CF_3$); −78.21 ($SO_3CF_3$); $^{13}C$ NMR ($CD_2Cl_2$, 100 MHz) δ=330.2 (CH-Me$_2$Ph), 309.3 (CH-Me$_2$Ph), 210.7 ($CN_{carbene}$), 208.1 ($CN_{carbene}$), 154.8 ($C_{ar.}$), 154.6 ($C_{ar.}$), 153.6 ($C_{ar.}$), 151.8 ($C_{ar.}$), 147.8 ($C_{ar.}$), 147.7 ($C_{ar.}$), 140.3 ($C_{ar.}$), 138.9 ($C_{ar.}$), 136.4 ($C_{ar.}$), 136.1 ($C_{ar.}$), 136.0 ($C_{ar.}$), 135.6 ($C_{ar.}$), 135.5 ($C_{ar.}$), 135.3 ($C_{ar.}$), 134.6 ($C_{ar.}$), 130.1 ($C_{ar.}$), 130.1 ($C_{ar.}$), 130.0 ($C_{ar.}$), 129.7 ($C_{ar.}$), 129.4 ($C_{ar.}$), 129.3 ($C_{ar.}$), 128.2 ($C_{ar.}$), 127.8 ($C_{ar.}$), 127.7 ($C_{ar.}$), 127.3 ($C_{ar.}$), 126.7 ($C_{ar.}$), 126.7 ($C_{ar.}$), 126.6 ($C_{ar.}$), 126.5 ($C_{ar.}$), 126.1 ($C_{ar.}$), 126.0 ($C_{ar.}$), 121.0 ($C_{ar.}$), 120.7 ($C_{ar.}$), 120.4 ($C_{ar.}$), 120.1 ($C_{ar.}$), 120.0 (q, CF$_3$, J=319 Hz), 120.0 (q, CF$_3$, J=320 Hz), 117.8 ($C_{ar.}$), 117.3 ($C_{ar.}$), 54.7 ($CH_{2-imidazolylidene}$), 54.2 ($CH_{2-imidazolylidene}$), 51.7 ($CH_{2-imidazolylidene}$), 51.3 ($CH_{2-imidazolylidene}$), 49.7 (CMe$_2$Ph), 49.5 (CMe$_2$Ph), 32.4 (CH$_3$), 29.2 (CH$_3$), 29.2 (CH$_3$), 27.3 (CH$_3$), 21.1 (CH$_3$), 21.0 (CH$_3$), 20.5 (CH$_3$), 19.0 (CH$_3$), 18.5 (CH$_3$), 18.0 (CH$_3$), 17.8 (CH$_3$), 17.3 (CH$_3$).

Example 17 (ROMP of 5,6-bis((pentyloxy)methyl) bicyclo-[2.2.1]hept-2-ene)

To an initially charged solution of the monomer (0.05 g, 0.167 mmol) in 2 mL of dichloromethane was added at room temperature, all at once, a catalyst solution of $Mo(N-2,6-Me_2-C_6H_3)(IMesH_2)$—(CHCMe$_2$Ph)(OTf)$_2$ (6) (0.0032 g, 0.0033 mmol) in 0.5 mL of dichloromethane. The mixture was stirred for four hours and then the polymer was precipitated in n-pentane. The wash phase was concentrated and precipitated again. The colorless polymer was washed with n-pentane and dried (0.045 g, 90%). $^1H$ NMR (400 MHz, CDCl$_3$): δ=5.27-5.15 (m, 2H), 3.34 (brs, 10H), 2.70 (brs, 1H), 2.31 (brs, 1H), 1.93 (brs, 2H), 1.54 (brs, 4H), 1.32 (brs, 8H), 0.89 (brs, 6H). $^{13}C$ NMR (101 MHz, CDCl$_3$): δ=134, 133.7, 71.25-70.25 (m), 50.9-39.91 (m), 29.7, 29.6, 28.7, 22.7, 14.2; FT-IR (ATR, cm$^{-1}$): 2928 (s), 2854 (s), 1460 (m), 1369 (m), 1104 (s), 967 (w), 734 (w); $M_n$=4000 g/mol, PDI=1.03, $σ_{trans}$=88%.

With $Mo(N-2,6-Me_2-C_6H_3)(IMes)(CHCMe_2Ph)(OTf)_2$ (7) (0.0032 g, 0.0033 mmol) in dichloromethane (0.5 mL) and the monomer (0.05 g, 0.167 mmol) in dichloromethane (2 mL), the polymer was isolated with a yield of 84% (0.042 g). $^1H$ NMR (400 MHz, CDCl$_3$): δ=5.27-5.17 (m, 2H), 3.34 (brs, 10H), 2.70 (brs, 1H), 2.31 (brs, 1H), 1.93 (brs, 2H), 1.54 (brs, 4H), 1.32 (brs, 8H), 0.89 (brs, 6H). $^{13}C$ NMR (101 MHz, CDCl$_3$): δ=134, 133.7, 71.12-70.63 (m), 47.60-39.92 (m), 29.7, 28.7, 22.7, 14.2; FT-IR (ATR, cm$^{-1}$): 2928 (s), 2854 (s), 1460 (m), 1369 (m), 1104 (s), 967 (w), 733 (w); $M_n$=8200 g/mol, PDI=1.06, $σ_{trans}$=93%.

With $Mo(N-2,6-Me_2-C_6H_3)(IMesH_2)(CHCMe_2Ph)(OTf)(OCH(CF_3)_2)$ (9) (0.0026 g, 0.00271 mmol) in dichloromethane (0.5 mL) and the monomer (0.04 g, 0.1358 mmol) in dichloromethane (2 mL), the polymer was prepared with a yield of 28% (0.012 g). $^1H$ NMR (400 MHz, CDCl$_3$): δ=5.27-5.17 (m, 2H), 3.34 (brs, 10H), 2.70 (brs, 1H), 2.31 (brs, 1H), 1.93 (brs, 2H), 1.54 (brs, 4H), 1.32 (brs, 8H), 0.89 (brs, 6H). $^{13}C$ NMR (101 MHz, CDCl$_3$): δ=134, 133.6, 71.11-70.11 (m), 47.60-39.78 (m), 29.6, 29.5, 28.5, 22.6, 22.5, 14.2; FT-IR (ATR, cm$^{-1}$): 2928 (s), 2854 (s), 1460 (m), 1369 (m), 1104 (s), 966 (w), 737 (w); $M_n$=11 400 g/mol, PDI=1.22, $σ_{trans}$=64%.

Example 18

The polymerization of the same monomer with $Mo(N-2,6-Me_2-C_6H_3)(I-tBu)(CH-tBu)(OTf)_2$ (2) (0.050 g of monomer, 2.6 mg of catalyst) affords the polymer in 60% isolated yield ($M_n$=8500 g/mol, PDI=1.1, $σ_{trans}$=50%).

Example 19 (ROMP of 7-oxabicyclo[2.2.1]hept-5-ene-2,3-diylbis(methylene) diacetate)

A cooled solution (−35° C.) of $Mo(N-2,6-Me_2-C_6H_3)(I-tBu)-(CH-tBu)(OTf)_2$ (2) (0.0045 g, 0.0050 mmol) in CH$_2$Cl$_2$ (0.5 mL) was added to a solution of the monomer (0.0600 g, 0.2520 mmol) in CH$_2$Cl$_2$ (2 mL) at −30° C. After 24 hours, the polymer was precipitated by adding pentane, washed with pentane and dried. Yield: 0.058 g (97%). FT-IR (ATR, cm$^{-1}$): 2902 (m), 1732 (s), 1431 (w), 1366 (s), 1220 (s), 1104 (w), 1029 (s), 968 (s), 728 (m). $^1$H NMR (400 MHz, CDCl$_3$): δ 5.72-5.58 (m, 2H), 4.49 (brs, 1H), 4.18 (m, 5H), 2.40 (brs, 2H), 2.03 (brs, 6H); $^{13}$C NMR (101 MHz, CDCl$_3$): δ 170.8, 133.1, 81.4, 61.9, 45.8, 20.9. M$_n$=13 000 g/mol, PDI=1.7, σ$_{trans}$=85%.

Example 20

The polymerization of 0.050 g of the same monomer with 0.0032 g of Mo(N-2,6-Me$_2$-C$_6$H$_3$)(I-tBu)-(CH-tBu)(OTf)$_2$ (2) affords the polymer in 35% yield (M$_n$=1800 g/mol, PDI=1.2, σ$_{trans}$=33%).

Example 21 (ROMP of
2-(N-cyclohexylmethyl)norborn-5-ene)

To a cooled solution (−30° C.) of 2-(N-cyclohexylmethyl)-norborn-5-ene (57.7 mg) in CH$_2$Cl$_2$ (2 mL) was added a solution of Mo(N-2,6-Me$_2$-C$_6$H$_3$)(IMesH$_2$)(CH-tBu)(OTf)$_2$ (1) (40 mg) in CH$_2$Cl$_2$ (0.5 mL). The reaction mixture was stirred at 80° C. for 24 h; then the polymer was precipitated by adding pentane, filtered off and dried (44.5 mg, 90%). FT-IR (ATR, cm$^{-1}$): 3270 (m), 2935 (s), 2860 (m), 2450 (m), 2075 (s), 1681 (m), 1454 (s), 1225 (m), 1159 (s), 1030 (s), 807 (s), 636 (s); $^1$H NMR (400 MHz, D$_2$O, hydrochloride salt): δ=6.40-5.86 (m), NH$_2^+$ part of the D$_2$O signal at 4.7, 3.17 (b), 3.03-2.96 (m), 2.60-2.0 (b, m), 1.93 (b), 1.74 (b), 1.40 (b), 1.28 (b); M$_n$=13 100 g/mol, PDI=1.10.

With Mo(N-2,6-Me$_2$-C$_6$H$_3$)(IMesH$_2$)—(CHCMe$_2$Ph)(OTf)$_2$ (6) (0.0074 g, 0.0078 mmol) and monomer (0.0400 g, 0.1951 mmol) in CH$_2$Cl$_2$ (3 mL), the polymer was obtained in 70% yield (0.028 g). FT-IR (ATR, cm$^{-1}$): 3421 (m), 2935 (s), 2858 (m), 2424 (m), 1630 (m), 1454 (s), 1222 (s), 1155 (s), 1030 (s), 724 (s), 637 (s); $^1$H NMR (400 MHz, CDCl$_3$): δ=8.69, 8.02, 7.04, 6.92, 6.19, 5.79, 5.77, 5.36, 5.28, 4.52, 3.83, 3.10, 2.96, 2.80, 2.36, 2.14, 2.00, 1.25, 0.86; $^{13}$C NMR (101 MHz, CDCl$_3$): δ=141.2, 138.8, 134.9, 132.0, 130.3, 129.3, 58.1, 49.8, 48.6, 44.5, 42.3, 35.7, 34.3, 24.8, 22.2, 17.8, 14.12.

With Mo(N-2,6-Me$_2$-C$_6$H$_3$)(IMes)(CHCMe$_2$Ph)(OTf)$_2$ (7) (0.0075 g, 0.0078 mmol) in dichloromethane (0.5 mL) and the monomer (0.04 g, 0.1951 mmol) in chloroform (2 mL), the polymer was obtained with ~65% yield (0.026 g). FT-IR (ATR, cm$^{-1}$): 3425 (m), 2920 (s), 2858 (m), 2424 (m), 1630 (m), 1454 (s), 1222 (s), 1155 (s), 1030 (s), 724 (s), 637 (s); $^1$H NMR (400 MHz, CDCl$_3$): δ=8.64, 7.06, 6.22, 6.21, 5.69, 5.34, 3.09, 2.85, 2.34, 2.17, 1.84, 1.82, 1.24, 0.88; $^{13}$C NMR (101 MHz, CDCl$_3$): δ=142.0, 138.8, 134.0, 131.7, 129.8, 50.10, 42.68, 34.4, 24.1, 22.8, 14.

With Mo(N-2,6-Me$_2$-C$_6$H$_3$)(IMesH$_2$)(CHCMe$_2$Ph)(OTf)(OCH(CF$_3$)$_2$) (9) (0.0082 g, 0.0078 mmol) in dichloromethane (0.5 mL) and the monomer (0.04 g, 0.1951 mmol) in dichloromethane (2 mL), the polymer was isolated with a yield of 54% (0.022 g). $^1$H NMR (400 MHz, CDCl$_3$): δ=6.97, 6.17, 6.07, 5.79, 5.77, 5.35, 5.33, 4.54, 3.45, 3.18, 2.96, 2.82, 2.64, 2.36, 2.31, 1.81, 1.60, 1.24; $^{13}$C NMR (101 MHz, CDCl$_3$): δ=140.7, 138.5, 137.1, 136.6, 135.2, 132.3, 130.3, 58.2, 48.7, 45.0, 42.8, 42.6, 36.2, 31.5, 29.0, 24.8, 21.0, 17.5, 14.4; FT-IR (ATR, cm$^{-1}$): 3421 (m), 2935 (s), 2858 (m), 2424 (m), 1630 (m), 1454 (s), 1222 (m), 1155 (s), 1030 (s), 724 (s), 637 (s).

Example 22 (ROMP of
2-(N,N-dimethylaminomethyl)-norborn-5-ene)

To a cooled solution (−30° C.) of 2-(N,N-dimethylaminomethyl)norborn-5-ene (79.7 mg) in CH$_2$Cl$_2$ (2 mL) was added a solution of Mo(N-2,6-Me$_2$-C$_6$H$_3$)—(IMesH$_2$)(CH-tBu)(OTf)$_2$ (1) (10.5 mg) in CH$_2$Cl$_2$ (0.5 mL). After stirring for 24 hours, the polymer was precipitated by adding pentane and filtered off and dried. Yield: 27 mg (34%). FT-IR (ATR, cm$^{-1}$): 2955 (s), 1629 (s), 1464 (s), 1259 (s), 1151 (s), 1029 (s), 636 (s); $^1$H NMR (400 MHz, DMSO-d$^6$): δ=6.98, 5.42, 3.14, 2.66, 2.32, 2.20, 2.17, 2.05, 0.85; M$_n$=10 500 g/mol, PDI=1.21.

Example 23 (ROMP of
norborn-5-ene-2,3-dimethanol)

A solution of Mo(N-2,6-Me$_2$-C$_6$H$_3$)(IMesH$_2$)(CH-tBu)(OTf)$_2$ (1) (0.0173 g, 0.0194 mmol) in CHCl$_3$ (1.5 mL) was added to a solution of the monomer (0.0300 g, 0.1940 mmol) in CHCl$_3$ (2 mL) at room temperature. The reaction mixture was then stirred at 55° C. for 5 hours. Subsequently, the polymer is precipitated from pentane, washed with pentane and dried. Yield 80% (0.024 g). FT-IR (ATR, cm$^{-1}$): 3373 (s), 2930 (s), 2884 (s), 1477 (m), 1261 (s), 1109 (s), 1023 (s), 921 (w), 632 (s); $^1$H NMR (400 MHz, DMSO-d$^6$): δ 5.48-5.40 (m, 2H), 3.86 (brs, 2H), 3.44 (brs, 4H), 2.45 (brs, 1H), 2.10 (brs, 1H), 1.83 (brs, 1H), 1.57 (brs, 1H), 1.33 (brs, 1H). $^{13}$C NMR (101 MHz, CDCl$_3$): δ=134.8, 129.5, 69.4, 59.3, 47.8, 47.0, 43.8, 43.4, 37.5 (b), 32.3; M$_n$=2800 g/mol, PDI=1.12.

Example 24 (ROMP of
bicyclo[2.2.1]hept-5-ene-2-carbaldehyde)

A solution of Mo(N-2,6-Me$_2$-C$_6$H$_3$)(IMesH$_2$)(CH-tBu)(OTf)$_2$ (1) (0.006 g, 0.0068 mmol) in CH$_2$Cl$_2$ (1.0 mL) was added to a solution of the monomer (0.0400 g, 0.3438 mmol) in CH$_2$Cl$_2$ (1.0 mL) at room temperature. The reaction mixture was then stirred at room temperature for 20 hours. Subsequently, the reaction was quenched with MeOH:HCl (90:10 vol./vol.). The polymer thus precipitated was washed with pentane and dried. Yield: 55% (0.022 g). FT-IR (ATR, cm$^{-1}$): 2942 (s), 2830 (m), 1720 (s), 1630 (s), 1470 (s), 1255 (s), 1158 (s), 1026 (s), 719 (s), 636 (s); $^1$H NMR (400 MHz, THF-d8): δ=9.53 (CHO), 6.13 (b), 5.95 (b), 4.62 (b), 2.75 (b); $^{13}$C NMR (101 MHz, THF-ds): δ=204.6 (CHO), 141.2, 136.9, 131.9, 130.7, 128.7, 43.2, 30.4, 21.2, 19.0, 17.9; M$_n$=5000 g/mol, PDI=2.1 (M$_{n, theor.}$=6100 g/mol).

Example 25 (General Method for the
Cyclopolymerization of Diynes)

The catalyst was dissolved in the solvent specified and this solution was added rapidly to one of the monomer in the same solvent. After 2 hours, the polyreactions were terminated by addition of wet methanol. After a further 10 min, the polymer was precipitated by adding methanol or pentane and dried.

Example 26 (Preparation of poly(4,4,5,5-tetrakis-
(ethoxycarbonyl)-1,7-octadiyne))

The polymer was obtained according to example 25 using Mo(N-2,6-Me$_2$-C$_6$H$_3$)(IMesH$_2$)(CH-tBu)(OTf)$_2$ (1) (3.6 mg, 0.004 mmol) and the monomer (80 mg, 0.203 mmol) in 81% isolated yield (64 mg). IR (cm$^{-1}$): 2901 (m), 1730 (s), 1461 (m), 1444 (m), 1387 (m), 1363 (m), 1265 (s), 1198 (m), 1122 (w), 1095 (m), 1052 (m), 1027 (s), 941 (m), 856 (m), 781 (w), 703 (w); $^1$H NMR (400 MHz, CDCl$_3$): δ=6.71 (s, 2H, CH), 4.41-4.25 (bs, 8H, CH$_2$), 3.25-3.18 (bs, 4H, CH$_2$), 1.38-1.23 (bs, 12H, CH$_3$); $^{13}$C NMR (101 MHz, CDCl$_3$): δ=169.7, 130.8, 124.7, 61.7, 56.9, 32.5, 13.7; UV/Vis (CHCl$_3$): λ$_{max}$=484 nm. M$_n$=13 200 g/mol, PDI=1.9 (M$_{n,\ theor.}$=19 700 g/mol).

It was possible to isolate the polymer through the use of Mo(N-2,6-Me$_2$-C$_6$H$_3$)(IMesH$_2$)(CHCMe$_2$Ph)(OTf)$_2$ (6) (0.0036 g, 0.004 mmol) and the monomer (0.0800 g, 0.203 mmol) with 81% yield (64 mg). The polymerization was initiated at –30° C., and stirring was continued at 80° C. for one hour. $^1$H NMR (CDCl$_3$): δ=7.01 (br, m, 2H), 4.21 (br, m, 8H), 3.18 (br, m, 4H), 1.28 (br, m, 12H); $^{13}$C NMR (CDCl$_3$): δ=169.9, 131.0, 125.0, 61.9, 57.1, 32.7, 14.0; FT-IR (ATR, cm$^{-1}$): 2981 (m), 1729 (s), 1444 (w), 1368 (s), 1262 (s), 1199 (w), 1092 (s), 1027 (w), 945 (s), 862 (w), 700 (w), 636 (w), 579 (w). UV/Vis (CHCl$_3$): λ$_{max}$=483 nm, M$_n$=15 000 g/mol, PDI=2.2, α insertion: ≥96%.

With the monomer (0.0400 g, 0.1014 mmol) and Mo(N-2,6-Me$_2$-C$_6$H$_3$)(IMes)(CHCMe$_2$Ph)(OTf)$_2$ (7) (0.0019 g, 0.0020 mmol), the polymer was prepared with a yield of 75% (0.03 g). $^1$H NMR (CDCl$_3$): δ=7.02 (br, m, 2H), 4.21 (br, m, 8H), 3.18 (br, m, 4H), 1.27 (br, m, 12H); $^{13}$C NMR (CDCl$_3$): δ=169.9, 131.0, 125.0, 61.9, 57.1, 32.7, 14.0; FT-IR (ATR, cm$^{-1}$): 2981 (m), 1729 (s), 1444 (w), 1368 (s), 1262 (s), 1199 (w), 1092 (s), 1027 (w), 945 (s), 862 (w), 700 (w), 636 (w), 579 (w). UV/Vis (CHCl$_3$): λ$_{max}$=481 nm, M$_n$=14 000 g/mol, PDI=1.8, α insertion: ≥96%.

With Mo(N-2,6-Me$_2$-C$_6$H$_3$)(IMesH$_2$)(CHCMe$_2$Ph)(OTf)(OCH(CF$_3$)$_2$) (9) (0.0022 g, 0.0020 mmol) and the monomer (0.0400 g, 0.1014 mmol), the polymer was likewise isolated with a yield of 75% (0.03 g). $^1$H NMR (CDCl$_3$): δ=7.02 (br, m, 2H), 4.22 (br, m, 8H), 3.19 (br, m, 4H), 1.27 (br, m, 12H); $^{13}$C NMR (CDCl$_3$): δ=169.9, 131.0, 125.0, 61.9, 57.1, 32.7, 14.0; FT-IR (ATR, cm$^{-1}$): 2981 (m), 1729 (s), 1444 (w), 1368 (s), 1262 (s), 1199 (w), 1092 (s), 1027 (w), 945 (s), 862 (w), 700 (w), 636 (w), 579 (w). UV/Vis (CHCl$_3$): λ$_{max}$=482 nm, M$_n$=22 000 g/mol, PDI=2.1, α insertion: ≥96%.

Example 27 (Preparation of poly(2-(prop-2-yn-1-yl)-pent-4-ynoic Acid))

The polymer was prepared from Mo(N-2,6-Me$_2$-C$_6$H$_3$)—(IMesH$_2$)(CHCMe$_2$Ph)(OTf)$_2$ (6) (0.0055 g, 0.0059 mmol) and the monomer (0.004 g, 0.294 mmol) with a yield of 65% (0.0260 g). The polymerization was initiated at –30° C. and stirring was continued at 80° C. for one hour. $^1$H NMR (400 MHz, d$_6$-DMSO): δ=12.25, 7.07-6.84, 3.23, 2.34; $^{13}$C NMR (400 MHz, d$_6$-DMSO): δ=177.0, 135.4, 129.5, 71.1, 58.1; FT-IR (ATR, cm$^{-1}$): 2981 (m), 1729 (s), 1444 (w), 1368 (s), 1262 (s), 1199 (w), 1092 (s), 1027 (w), 945 (s), 862 (w), 700 (w), 636 (w), 579 (w). UV/Vis (CHCl$_3$): λ$_{max}$=587, 547 nm.

With Mo(N-2,6-Me$_2$-C$_6$H$_3$)(IMes)(CHCMe$_2$Ph)(OTf)$_2$ (7) (0.0055 g, 0.0059 mmol) and the monomer (0.0400 g, 0.294 mmol), the polymer was isolated with 55% yield (0.022 g). $^1$H NMR (400 MHz, d$_6$-DMSO): δ=12.27, 6.68-6.76, 3.23, 2.34; $^{13}$C NMR (400 MHz, d$_6$-DMSO): δ=177.0, 135.4, 129.5, 71.1, 58.1; FT-IR (ATR, cm$^{-1}$: 2981 (m), 1729 (s), 1444 (w), 1368 (s), 1262 (s), 1199 (w), 1092 (s), 1027 (w), 945 (s), 862 (w), 700 (w), 636 (w), 579 (w). UV/Vis (CHCl$_3$): λ$_{max}$=587, 547 nm.

With the monomer (0.0400 g, 0.294 mmol) and Mo(N-2,6-Me$_2$-C$_6$H$_3$)(IMesH$_2$)(CHCMe$_2$Ph)(OTf)(OCH(CF$_3$)$_2$) (9) (0.0062 g, 0.0059 mmol), it was likewise possible to obtain the polymer with the yield of 55% (0.022 g). $^1$H NMR (400 MHz, d$_6$-DMSO): δ=12.27, 6.68-6.76, 3.23, 2.34; $^{13}$C NMR (400 MHz, d$_6$-DMSO): δ=177.0, 135.4, 129.5, 71.1, 58.1; FT-IR (ATR, cm$^{-1}$): 2981 (m), 1729 (s), 1444 (w), 1368 (s), 1262 (s), 1199 (w), 1092 (s), 1027 (w), 945 (s), 862 (w), 700 (w), 636 (w), 579 (w). UV/Vis (CHCl$_3$): λ$_{max}$=587, 547 nm.

Example 28 (Preparation of poly(2,2-di(prop-2-yn-1-yl)propane-1,3-diol))

The polymer was obtained using Mo(N-2,6-Me$_2$-C$_6$H$_3$)—(IMesH$_2$)(CH-tBu)(OTf)$_2$ (1) in 80% isolated yield (0.030 g). $^1$H NMR (400 MHz, d$_6$-DMSO): δ=7.09-6.66 (m, 2H), 4.60 (brs, 2H), 3.17 (s, 2H), 2.08 (s, 2H). UV-vis: λ$_{max}$=593, 554 nm (DMSO).

With Mo(N-2,6-Me$_2$-C$_6$H$_3$)(IMesH$_2$)(CHCMe$_2$Ph)(OTf)$_2$ (6) (0.010 g, 0.0105 mmol) and the monomer (0.04 g, 0.2628 mmol), the polymer was prepared with a yield of 70% (0.027 g). The polymerization was initiated at –30° C., and stirring was continued at room temperature for one hour. $^1$H NMR (400 MHz, d$_6$-DMSO): δ=7.27-6.66, 4.42, 2.34, 2.29, 1.9; $^{13}$C NMR (101 MHz, d$_6$-DMSO): δ=139.7, 135.4, 130.9, 129.4, 50.9, 20.5, 17.6, 17.2; IR (ATR mode, cm$^{-1}$): 3400 (w), 2977 (w), 1444 (w), 1367 (w), 1247 (m), 1159 (m), 1065 (m), 946 (w), 856 (w), 629 (w). UV-vis: λ$_{max}$=593, 554 nm (DMSO); M$_n$=5000 g/mol, PDI=2.1.

In the case of use of Mo(N-2,6-Me$_2$-C$_6$H$_3$)—(IMes)(CHCMe$_2$Ph)(OTf)$_2$ (7) (0.010 g, 0.0105 mmol) and the monomer (0.0400 g, 0.2628 mmol), it was possible to prepare the polymer with a yield of 65% (0.026 g). $^1$H NMR (400 MHz, d$_6$-DMSO): δ=7.19-6.72, 2.86, 2.34, 2.26, 2.1, 1.82; $^{13}$C NMR (101 MHz, d$_6$-DMSO); δ=139.7, 135.4, 130.9, 129.4, 50.9, 20.5, 17.6, 17.2; IR (ATR mode, cm$^{-1}$): 3420 (w), 2963 (w), 1465 (w), 1353 (w), 1233 (m), 1122 (m), 1072 (m), 920 (w), 863 (w), 640 (w). UV-vis: λ$_{max}$=595, 554 nm (DMSO); M$_n$=3900 g/mol, PDI=1.8.

In the case of use of Mo(N-2,6-Me$_2$-C$_6$H$_3$)(IMesH$_2$)(CHCMe$_2$Ph)(OTf)(OCH(CF$_3$)$_2$) (9) (0.0011 g, 0.0052 mmol) and the monomer (0.0400 g, 0.212 mmol), the polymer was isolated with 54% yield (0.022 g). IR (ATR mode, cm$^{-1}$): 3400 (w), 2977 (w), 1444 (w), 1367 (w), 1247 (m), 1159 (m), 1065 (m), 946 (w), 856 (w), 629 (w). UV-vis: λ$_{max}$=593, 554 nm (DMSO); M$_n$=3000 g/mol, PDI=1.3.

Example 29 (poly(dipropargylmalonitrile))

A solution of Mo(N-2,6-Me$_2$-C$_6$H$_3$)(IMesH$_2$)(CH-tBu)(OTf)$_2$ (1) (0.016 g, 0.0211 mmol) in CH$_2$Cl$_2$ (0.5 mL) was added to a solution of the monomer (0.0300 g, 0.211 mmol) in CH$_2$Cl$_2$ (2 mL) at –30° C. The mixture was stirred at room temperature for 90 min, then quenched with MeOH—HCl (90:10, vol./vol.). The precipitated polymer was washed with pentane and dried. Yield: 60% (0.018 g). IR (cm$^{-1}$): 2960 (m), 2252 (w), 1588 (w), 1484 (m), 1267 (s), 1232 (s), 1027 (s), 810 (w), 636 (s); $^1$H NMR (DMSO-d$_6$): δ=7.5-6.5 (b), 53.8 (b); $^{13}$C NMR (DMSO-d$_6$): δ=160.2, 139.6, 135.4, 130.8, 129.4, 50.9, 30.2, 20.6, 17.6; UV/Vis (DMSO): λ$_{max}$=530 nm. M$_n$=1100 g/mol, PDI=1.15 (M$_{n,\ theor.}$=1420 g/mol).

Example 30 (poly(1,7-octadiyne-4,5-dicarboxylic Acid)

A solution of Mo(N-2,6-Me$_2$-C$_6$H$_3$)(IMesH$_2$)(CH-tBu)(OTf)$_2$ (1) (0.0137 g, 0.0154 mmol) in CH$_2$Cl$_2$ (1.0 mL) was added to a solution of the monomer (0.0300 g, 0.1956 mmol) in THF (2 mL) at –30° C. The reaction mixture was stirred at room temperature for 1 hour, then the polymer was precipitated with pentane, washed with pentane and dried. Yield: 90% (0.034 g). IR (cm$^{-1}$): 3288 (m), 2918 (m), 1702 (s), 1431 (m), 1213 (s), 1168 (s), 1026 (s), 946 (m), 634 (s); $^{13}$C NMR (CDCl$_3$): δ=174.8, 128-140 (b), 40.4, 30.1; $^{13}$C NMR (LiOD/D$_2$O): δ=184.5, 132-128, 44.4, 30.5; UV/Vis (THF): λ$_{max}$=432 nm. M$_n$=2600 g/mol, PDI=1.3 (M$_{n, theor.}$=2500 g/mol).

Example 31
(poly(4,4-bis(ethoxycarbonyl)-1,6-heptadiyne; poly(DEDPM))

The polymer was prepared using Mo(N-2,6-Me$_2$-C$_6$H$_3$)—(IMesH$_2$)(CH-tBu)(OTf)$_2$ (1) (4.5 mg, 0.0051 mmol) and the monomer (60 mg, 0.2540 mmol) in 89% yield (53 mg). The polymerization was initiated at −30° C. and then conducted at room temperature for a further hour. $^1$H NMR (CDCl$_3$): δ=6.95-6.83 (s, 1H, CH), 6.45 (s, 1H, CH), 4.10-3.37 (bm, 6H, CH$_2$), 2.82 (s, 1H, CH), 2.05-1.80 (m, 2H, CH$_2$), 1.17 (s, 3H); $^{13}$C NMR (CDCl$_3$): δ=170.9, 170.8, 169.0, 137.0, 123.2, 61.9, 58.2, 58.0, 57.3, 57.1, 54.3, 54.1, 41.5, 29.7, 14.1; IR (ATR, cm$^{-1}$): 3367 (m), 2969 (s), 2929 (s), 2864 (s), 1673 (s), 1519 (m), 1453 (m), 1366 (s), 1337 (w), 1258 (w), 1190 (w), 1125 (s), 1077 (s), 947 (m), 770 (s), 690 (w); UV/Vis (CHCl$_3$): λ$_{max}$=548, 584 nm, α insertion: 81%, k$_p$/k$_i$=7.

With Mo(N-2,6-Me$_2$-C$_6$H$_3$)(IMesH$_2$)(CHCMe$_2$Ph)(OTf)$_2$ (6) (0.004 g, 0.0042 mmol) and monomer (0.05 g, 0.213 mmol), the polymer was obtained in 84% yield. $^1$H NMR (400 MHz, CDCl$_3$): δ=6.68 (br m, 2H), 4.27 (br m, 4H), 3.43 (br m, 4H), 1.30 (br m, 6H) ppm; $^{13}$C NMR (101 MHz, CDCl$_3$): δ=172.1, 137.1, 128.4, 126.3, 123.3, 62.1, 57.4, 41.6, 14.2 ppm; IR (ATR mode, cm$^{-1}$): 2977 (w), 1720 (s), 1444 (w), 1367 (w), 1247 (m), 1159 (m), 1065 (m), 946 (w), 856 (w), 629 (w). UV/Vis (CHCl$_3$): λ$_{max}$25=586, 546 nm. M$_n$=8500 g/mol, PDI=2.1, α insertion: ≥95%.

In the case of use of Mo(N-2,6-Me$_2$-C$_6$H$_3$)—(IMes)(CHCMe$_2$Ph)(OTf)$_2$ (7) (0.0040 g, 0.0042 mmol) and the monomer (0.0500 g, 0.212 mmol), it was possible to isolate poly(DEDPM) with a yield of 86% (0.043 g). $^1$H NMR (CDCl$_3$): δ=6.68 (br m, 2H), 4.27 (br m, 4H), 3.43 (br m, 4H), 1.31 (br m, 6H); $^{13}$C NMR (CDCl$_3$): δ=172.1, 138.7, 128.0, 125.8, 122.9, 62.1, 57.4, 41.5, 14.2; FT-IR (ATR, cm$^{-1}$): 2979 (m), 1722 (s), 1446 (w), 1367 (s), 1248 (s), 1158 (w), 1067 (s), 947 (s), 631 (m). UV/Vis (CHCl$_3$): λ$_{max}$=587, 546 nm. M$_n$=84 000 g/mol, PDI=2.8, α insertion: ≥99%.

In the case of use of Mo(N-2,6-Me$_2$-C$_6$H$_3$)—(IMesH$_2$)(CHCMe$_2$Ph)(OTf)(OCH(CF$_3$)$_2$) (9) (0.0040 g, 0.0042 mmol) with the monomer (0.0500 g, 0.212 mmol), it was possible to isolate poly(DEDPM) with a yield of 54% (0.043 g). $^1$H NMR (CDCl$_3$): δ=6.68 (br m, 2H), 4.27 (br m, 4H), 3.43 (br m, 4H), 1.31 (br m, 6H); $^{13}$C NMR (CDCl$_3$): δ=172.1, 137.1, 128.2, 126.4, 123.3, 62.1, 57.4, 41.6, 14.2; FT-IR (ATR, cm$^{-1}$): 2977 (m), 1721 (s), 1444 (w), 1367 (s), 1248 (s), 1158 (w), 1067 (s), 947 (s), 631 (m). UV/Vis (CHCl$_3$): λ$_{max}$=581, 546 nm, M$_n$=67 400 g/mol, PDI=2.7, α insertion: ≥96%.

Example 32 (poly(4,4-bis[(3,5-diethoxybenzoyloxy)-methyl]-1,6-heptadiyne))

The polymer was prepared using Mo(N-2,6-Me$_2$-C$_6$H$_3$)—(IMesH$_2$)(CH-tBu)(OTf)$_2$ (1) (1.9 mg, 0.0022 mmol) and the monomer (60 mg, 0.1120 mmol) in 94% yield (57 mg). The polymerization was initiated at −30° C. and then conducted at room temperature for a further hour. $^1$H NMR (CDCl$_3$): δ=7.04-6.92 (m, 4H), 6.71-6.60 (m, 2H), 6.45-6.31 (m, 2H), 4.44-4.31 (m, 4H), 3.90-3.81 (m, 8H), 2.89-2.82 (m, 4H), 1.40-1.25 (m, 12H); $^{13}$C NMR (CDCl$_3$): δ=168.3, 159.3, 138.2, 131.2, 107.7, 107.6, 106.3, 63.6, 40.7, 27.1, 14.7; IR (ATR, cm$^{-1}$): 3367 (m), 2969 (s), 2929 (s), 2864 (s), 1673 (s), 1519 (m), 1453 (m), 1366 (s), 1337 (w), 1258 (w), 1190 (w), 1125 (s), 1077 (s), 947 (m), 770 (s), 690 (w); UV/Vis (CHCl$_3$): λ$_{max}$=550, 590 nm, α insertion: >91%; k$_p$/k$_i$=33.

It was possible to isolate the polymer through the use of Mo(N-2,6-Me$_2$-C$_6$H$_3$)(IMesH$_2$)(CHCMe$_2$Ph)(OTf)$_2$ (6) (0.0014 g, 0.0015 mmol) and the monomer (0.04 g, 0.0745 mmol) in quantitative yield (0.0392 g). The polymerization was initiated at −30° C. and stirring was continued at 80° C. for one hour. $^1$H NMR (CDCl$_3$): δ=6.90 (br, m, 4H), 6.36 (br, m, 4H), 4.30 (brs, 4H), 3.85 (brs, 8H), 2.81 (brs, 4H), 1.29 (brs, 12H); $^{13}$C NMR (CDCl$_3$): δ=168.5, 159.9, 138.3, 131.1, 123.4, 107.7, 106.4, 69.6, 63.7, 43.4, 40.8, 14.8; FT-IR (ATR, cm$^{-1}$): 2978 (w), 1788 (w), 1716 (s), 1592 (s), 1446 (m), 1385 (w), 1296 (m), 1216 (s), 1166 (s), 1101 (m), 1051 (m), 990 (w), 817 (w), 757 (m), 675 (w), 619 (m); UV/Vis (CHCl$_3$): λ$_{max}$=591, 550 nm, α insertion: ≥93%.

With the monomer (0.0400 g, 0.754 mmol) and Mo(N-2,6-Me$_2$-C$_6$H$_3$)(IMes)(CHCMe$_2$Ph)(OTf)$_2$ (7) (0.0014 g, 0.0015 mmol), the polymer was prepared with a yield of 60% (0.0255 g). $^1$H NMR (CDCl$_3$): δ=6.90 (br, m, 4H), 6.36 (br, m, 4H), 4.30 (br, s, 4H), 3.84 (br, S, 8H), 2.81 (br, s, 4H), 1.28 (br, s, 12H); $^{13}$C NMR (CDCl$_3$): δ=166.5, 159.9, 138.5, 131.2, 123.4, 107.6, 106.4, 69.6, 63.8, 43.4, 40.8, 14.5; FT-IR (ATR, cm$^{-1}$): 2978 (w), 1787 (w), 1716 (s), 1591 (s), 1446 (m), 1385 (w), 1297 (m), 1216 (s), 1166 (s), 1101 (m), 1051 (m), 990 (w), 817 (w), 757 (m), 674 (w), 618 (m), UV/Vis (CHCl$_3$): λ$_{max}$=590, 550 nm, α insertion: ≥93%.

The polymer was prepared with Mo(N-2,6-Me$_2$-C$_6$H$_3$)—(IMesH$_2$)(CHCMe$_2$Ph)(OTf)(OCH(CF$_3$)$_2$) (9) (0.0015 g, 0.0015 mmol) and the monomer (0.0400 g, 0.0745 mmol) with a yield of only 50% (0.020 g). $^1$H NMR (CDCl$_3$): 5=6.90 (br, m, 4H), 6.36 (br, m, 4H), 4.30 (br, s, 4H), 3.84 (br, s, 8H), 2.81 (br, s, 4H), 1.28 (br, s, 12H); $^{13}$C NMR (CDCl$_3$): δ=166.4, 159.9, 138.3, 131.2, 123.4, 107.6, 106.4, 69.5, 63.6, 43.4, 40.8, 14.8; FT-IR (ATR, cm$^{-1}$): 2978 (w), 1787 (w), 1716 (s), 1591 (s), 1446 (m), 1385 (w), 1297 (m), 1216 (s), 1166 (s), 1101 (m), 1051 (m), 990 (w), 817 (w), 757 (m), 674 (w), 618 (m), UV/Vis (CHCl$_3$): λ$_{max}$=591, 550 nm, α insertion: ≥95%.

Example 33 (General Procedure for the Reactions with the Catalysts 1-18)

Homo-Metathesis and Ring-Closing Metathesis (RCM):
The reactions are conducted in 1,2-dichloroethane (5 mL) and the appropriate substrates (see table 1). T=80° C.; catalyst:substrate (unless stated otherwise)=1:1000. The conversion was determined by GC-MS after a reaction time of four hours. Internal standard: dodecane. The results of these studies are shown in table 1 below.
Ring-Opening Metathesis Polymerization (ROMP):
All reactions were conducted at 80° C. in 1,2-dichloroethane over a period of 4 hours. Monomer/catalyst=50:1. The results of these studies are shown in table 2 below.
Cyclopolymerization of α,ω-diynes:
All reactions were conducted at −30° C. to room temperature in dichloromethane at a monomer/catalyst ratio of 50:1 and, unless stated otherwise, over a period of 1 hour. The results of these studies are shown in tables 3 to 7 below.

The monomers used within the context of the ROMP and cyclopolymerizations are shown below:
I
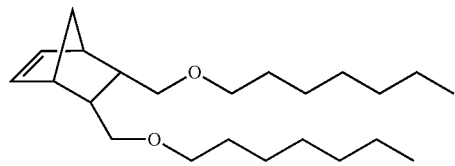
II
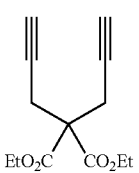
III
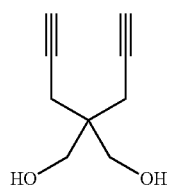
IV
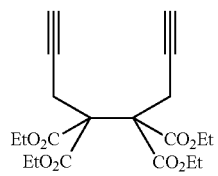
V
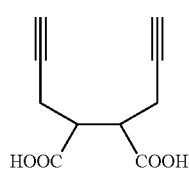
VI
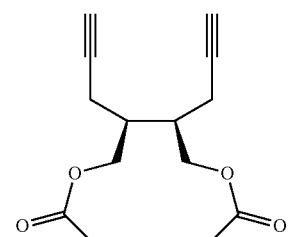
VII
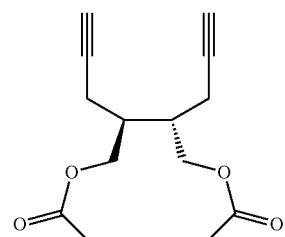
VIII
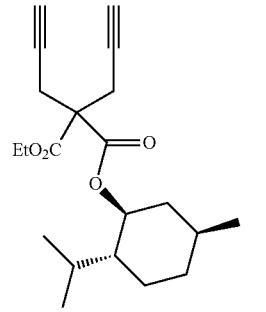
TABLE 1
Turnover numbers of catalysts 9-14 in various olefin metathesis reactions.
| | 9 | 10 | 11 | 12 | 13 | 14 |
|---|---|---|---|---|---|---|
| Substrate | | | | | | |
| Homo-metathesis (HM), (values in brackets indicate the E fraction in %) | | | | | | |
| Allyltrimethyl-silane | 520 (60) | 435 (55) | — | — | 460 (60) | 350 (60) |
| 1-Hexene | 340 (100) | 490 (100) | 790 (100) | 85 000[c] (100) 140 000[d] (100) | 660 (100) | 540 (100) |
| Styrene | 60 (100) | 80 (100) | 200 (100) | 45 000[d] (100) | 30 | — |
| 1-Octene | 680 (85) | 560 (85) | | 210 000[d] 150 000 (86) | 400 (100) | 480 (100) |

TABLE 1-continued

Turnover numbers of catalysts 9-14 in various olefin metathesis reactions.

| | 9 | 10 | 11 | 12 | 13 | 14 |
|---|---|---|---|---|---|---|
| Ring-closing metathesis (RCM) | | | | | | |
| Diethyl diallyl malonate | 175 | 90 | 3200[b] | | 150 | 350 |
| Diallyldiphenylsilane | 620 | 490 | 390 | | 660 | 520 |
| 1,7-Octadiene | 140 | 920 | 4100[b] | 80 000[c] 100 000[d] | 830 | 650 |
| N,N-Diallyl-t-butylcarbamide | 390 | 50 | | | 270 | 0 |
| N,N-Diallyl-p-tosylamide | 180 | 160 | 420 | | 250 | 350 |
| N,N-Diallyltrifluoroacetamide | 62 | — | — | | 15 | 0 |
| Diallylmalonitrile | 190 | 70 | 360 | | 100 | 150 |
| Diallyl ether | 220 | 245 | 690 | | 0 | 0 |

[a]ClCH$_2$CH$_2$Cl, 80° C., 4 h, cat:substrate = 1:1000,
[b]ClCH$_2$CH$_2$Cl, 80° C., 4 h, cat:substrate = 1:5000,
[c]ClCH$_2$CH$_2$Cl, RT, overnight, cat:substrate = 1:100 000,
[d]ClCH$_2$CH$_2$Cl, RT, 1 h, cat:substrate = 1:500 000.

TABLE 2

Summary of the polymerization results with catalysts 9-11. Monomer:catalyst = 50:1. All reactions were conducted in CH$_2$Cl$_2$ at room temperature.

| Monomer | Catalyst | Yield (%) | Selectivity (cis/trans) | $M_n$ (g/mol) | PDI |
|---|---|---|---|---|---|
| I | 9 | 84 | ≥95% | 4000 | 1.03 |
| I | 10 | 86 | ≥99% | 8200 | 1.06 |
| I | 11 | 28 | ≥64% | 11 400 | 1.22 |

TABLE 3

Reactivity of catalysts 8, 9 and 11 in the cyclopolymerization of α,ω-diynes. Monomer:catalyst = 50:1

| Monomer | Cat. | Solv./T (° C.)/t | Yield (%) | α Selectivity | $M_n$ (g/mol) | PDI |
|---|---|---|---|---|---|---|
| II | 9 | CH$_2$Cl$_2$, −30° C.-RT, 1 h | 84 | ≥95% | 8500 | 2.1 |
| II | 10 | CH$_2$Cl$_2$, −30° C.-RT, 1 h | 86 | ≥99% | 84 000 | 2.3 |
| II | 11 | CH$_2$Cl$_2$, −30° C.-RT, 1 h | 54 | ≥96% | 67 000 | 2.7 |
| III | 9 | CH$_2$Cl$_2$, −30° C.-RT, 1 h | 70 | — | 5000 | 2.1 |
| III | 10 | CH$_2$Cl$_2$, −30° C.-RT, 1 h | 56 | — | 3900 | 1.8 |
| III | 11 | CH$_2$Cl$_2$, −30° C.-RT, 1 h | 54 | — | 3000 | 1.3 |
| IV | 9 | CHCl$_3$, −30° C.-80° C., 1 h | 81 | 96 | 15 000 | 2.2 |
| IV | 10 | CHCl$_3$, −30° C.-80° C., 1 h | 75 | 96 | 14 000 | 1.8 |
| IV | 11 | CHCl$_3$, −30° C.-80° C., 1 h | 75 | 96 | 2200 | 2.1 |
| V | 9 | CHCl$_3$, −30° C.-80° C., 1 h | 65 | — | 3300 | 1.9 |
| V | 10 | CHCl$_3$, −30° C.-80° C., 1 h | 55 | — | 2900 | 1.4 |
| V | 11 | CHCl$_3$, −30° C.-80° C., 1 h | 55 | — | 6000 | 1.5 |

TABLE 4

Cyclopolymerization of VI with initiator 6.

| Initiator (I) | M:I ratio | $M_{n,exp}$[a] [g/mol] | Yield [%][b] | PDI | α Selectivity [%] | trans [%] | st [%] |
|---|---|---|---|---|---|---|---|
| 6 | 50:1 | 19 800 | 47 | 1.3 | 96 | 100 | 72 |

CH$_2$Cl$_2$, −30° C. to 20° C., 3 h.
$\lambda_{max}$ = 469 nm, poly-VI: $M_{n,theo}$ = 27 900 g/mol.
[a]GPC in CHCl$_3$, UV-vis detector, calibration against poly(styrene) standards;
[b]isolated, gravimetrically determined yields.
st = syndiotactic.

TABLE 5

Cyclopolymerization of VII with initiator 6.

| Initiator (I) | M:I ratio | $M_{n,exp}$[a] [g/mol] | Yield [%][b] | PDI | α Selectivity [%] | trans [%] | it [%] |
|---|---|---|---|---|---|---|---|
| 6 | 50:1 | 24 800 | 24 | 1.5 | 95 | — | 34 |

CH$_2$Cl$_2$, −30° C. to 20° C., 2 h.
$\lambda_{max}$ = 463 nm, poly-VII: $M_{n,theo}$ = 27 900 g/mol.
[a]GPC in CHCl$_3$, UV-vis detector, calibration against poly(styrene) standards;
[b]isolated, gravimetrically determined yields.
it = isotactic.

TABLE 6

Cyclopolymerization of monomer III with initiator 6.

| Initiator (I) | M:I ratio | $M_{n,\,exp}$[a] [g/mol] | Yield [%][b] | PDI |
|---|---|---|---|---|
| 6 | 50:1 | 9000 | 90 | 1.1 |

CH$_2$Cl$_2$, −30° C. to 20° C., 2 h. Poly-III: $M_{n,\,theo}$ = 8300 g/mol.
[a]GPC in DMSO, UV-vis detector, calibration against poly(styrene) standards;
[b]isolated, gravimetrically determined yields.

TABLE 7

| Cyclopolymerization of monomer VIII with initiators 1 and 4. | | | | | | | |
|---|---|---|---|---|---|---|---|
| Initiator (I) | M:I ratio | $M_{n,exp}$[a] [g/mol] | $\lambda_{max}$ [nm] | Yield [%][b] | PDI | α Selectivity [%] | trans [%] | st [%] |
| 1 | 50:1 | 32 300 | 550; 591 | 83 | 2.1 | >90 | 100 | 100 |
| 4 | 50:1 | 27 500 | 547; 585 | 77 | 1.8 | >71 | 100 | 74 |

CH$_2$Cl$_2$, −30° C. to 20° C., 2 h.
Poly-VIII: $M_{n,theo}$ = 17 300 g/mol.
[a]GPC in CHCl$_3$, UV-vis detector, calibration against poly(styrene) standards;
[b]isolated, gravimetrically determined yields.

Example 34 (Immobilization of 4-(hydroxymethyl)-1,3-dimesityl-4,5-dihydro-1H-imidazol-3-ium chloride (I1))

G60 silica gel (350 mg) were suspended in 10 mL of chloroform. A few drops of concentrated sulfuric acid were added thereto. 4-(Hydroxymethyl)-1,3-dimesityl-4,5-dihydro-1H-imidazol-3-ium chloride (500 mg, 1.34 mmol) was dissolved in 10 mL of chloroform and added to the reaction mixture. The reaction mixture was stirred at 60° C. overnight in order then to be cooled to room temperature and filtered. The solids obtained were washed repeatedly with CH$_2$Cl$_2$ and demineralized water. In order to remove residues of water, the solids were suspended in dry THF and stirred for one hour. The solids were filtered off and washed with diethyl ether. All volatile constituents were removed under reduced pressure. The solids were suspended in 20 mL of CH$_2$Cl$_2$, 1 mL of trimethylsilyl chloride (8.14 mmol) was added to this solution, and the mixture was stirred at room temperature overnight. All volatile constituents were removed under reduced pressure, and the product was obtained as a white solid.

Deprotonation of I1 to I2: I1 was suspended in 20 mL of THF. To this was added lithium hexamethyldisilazide (LiH-MDS, 0.22 g, 1.34 mmol), and the mixture was stirred at room temperature for two hours. The reaction mixture was filtered and the resulting solids were suspended in DMSO and stirred for 30 min. The solids were filtered off and washed repeatedly with diethyl ether. All volatile constituents were removed under reduced pressure and the product was obtained as a pale yellow solid. $^1$H MAS NMR (400.13 MHz): δ=6.59 (H$_{arom}$); 3.28 (CH$_2$, CH); 1.67, 0.87, 0.03 (CH$_3$).

Example 35 (Immobilization of [Mo(N-2,6-Me$_2$C$_6$H$_3$)—(CHC(CH$_3$)$_2$Ph)(OTf)$_2$(DME)] on I2 (IMo-1))

Mo(N-2,6-Me$_2$C$_6$H$_3$)(CHC(CH$_3$)$_2$Ph)(OTf)$_2$(DME) (100 mg, 0.14 mmol) was dissolved in 3 mL of benzene. I2 was added to this solution and stirred at room temperature for three hours. The solvent was decanted off and the solids were washed repeatedly with benzene, diethyl ether and CH$_2$Cl$_2$ until the solvents were no longer colored. All volatile components were removed under reduced pressure and the product was obtained as an orange solid. $^1$H MAS NMR (400.13 MHz): δ=12.60 (CHCMe$_2$Ph); 6.88 (H$_{arom}$); 2.54 (CH$_3$, CH$_2$, CH); 0.13 (CH$_3$).

Example 36 (Immobilization of [Mo(N-2,6-Cl$_2$C$_6$H$_3$)—(CHC(CH$_3$)$_3$)(OTf)$_2$(DME)] on I2 (IMo2))

Mo(N-2,6-Cl$_2$C$_6$H$_3$)(CHC(CH$_3$)$_3$)(OTf)$_2$(DME) (200 mg, 0.26 mmol) was dissolved in 3 mL of benzene. I2 was added to this solution and stirred at room temperature for three hours. The solvent was decanted off and the solids were washed repeatedly with benzene, diethyl ether and CH$_2$Cl$_2$ until the solvents were no longer colored. All volatile components were removed under reduced pressure and the product was obtained as an orange solid. $^1$H MAS NMR (400.13 MHz): δ=13.77 (CHCMe$_2$Ph); 6.96 (H$_{arom}$); 2.69 (CH$_3$, CH$_2$, CH); 0.11 (CH$_3$).

Example 37 (General Procedure for Metathesis Reactions with IMo1 and IMo2)

The metathesis substrate was dissolved in CH$_2$Cl$_2$ (or ClH$_2$C—CH$_2$Cl) which had been filtered through Al$_2$O$_3$, and 50 μL of dodecane were added as internal standard for GC-MS determination of conversion. The immobilized catalyst was suspended in CH$_2$Cl$_2$ (or ClH$_2$C—CH$_2$Cl) which had been filtered through Al$_2$O$_3$ and added rapidly to the solution prepared beforehand. The reaction mixture was stirred at 40° C. (or 80° C.) for 4 h. After cooling to room temperature, the reaction mixture was filtered through a glass fiber filter paper. For the GC-MS analysis, a sample was taken directly from this solution. If the conversion was determined by means of NMR, no internal standard was added and the solvent was removed completely for the analysis.

| Substrate | Initiator | Ratio (cat:substrate) | Yield [%] | Turnover number |
|---|---|---|---|---|
| 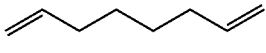 | IMo1 | 1:563 | 38 | 210 |
| | IMo2 | 1:590 | 90 | 532 |
| 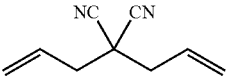 | IMo1 | 1:1000 | 3 | 30 |
| | IMo2 | 1:1000 | 12 | 120 |

-continued

| Substrate | Initiator | Ratio (cat:substrate) | Yield [%] | Turnover number |
|---|---|---|---|---|
| Ph₂Si(allyl)₂ | IMo1 | 1:440 | 41 | 184 |
|  | IMo2 | 1:305 | 30 | 90 |
| TsN(allyl)₂ | IMo1 | 1:1000 | 10 | 100 |
|  | IMo2 | 1:1000 | 10 | 100 |
| BocN(allyl)₂ | IMo1 | 1:448 | 24 | 106 |
|  | IMo2 | 1:478 | 48 | 217 |

| Substrate | Initiator | Ratio (cat:substrate) | Yield [%] | Turnover number | trans:cis |
|---|---|---|---|---|---|
| 1-hexene | IMo1 | 1:481 | 68 | 327 | 1:0 |
|  | IMo2 | 1:836 | 4.3 | 37 | 1:0 |
| allyl-SiMe₃ | IMo1 | 1:571 | 100 | 571 | 1:1.3 |
|  | IMo2 | 1:548 | 100 | 548 | 1:1.1 |
| 1-hexene + allyl-SiMe₃ | IMo1 | 1:123 | 100 | 123 | 1:0.6 |
|  | IMo2 | 1:76 | 100 | 76 | 1:0.7 |
| styrene + allyl-SiMe₃ | IMo1 | 1:251 | 100 | 251 | 1:9.4 |
|  | IMo2 | 1:59 | 100 | 59 | 1:21.8 |

| Substrate | Initiator | Ratio (cat:substrate) | Yield [%] | Turnover number |
|---|---|---|---|---|
| norbornene-diol + allyl-SiMe₃ | IMo1 | 1:59 | 42 | 25 |

Structures of Tungsten-Oxo-Alkylidene-NHC Complexes Prepared

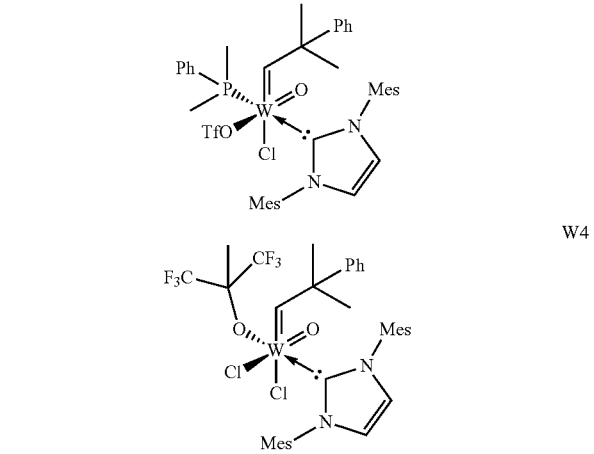

W5 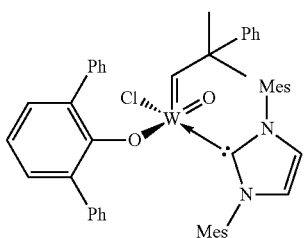
W6 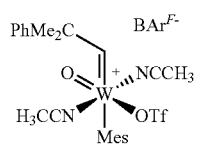
W7 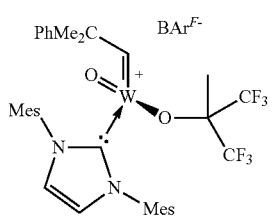
W8 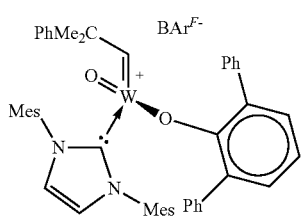
W9 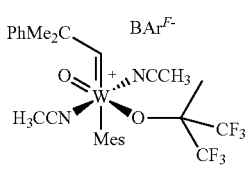
W10 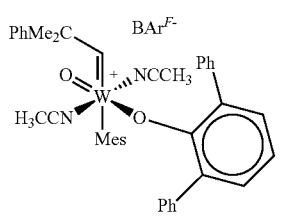
W11 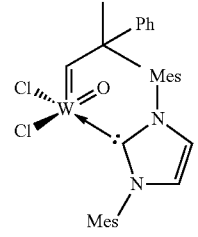
W12 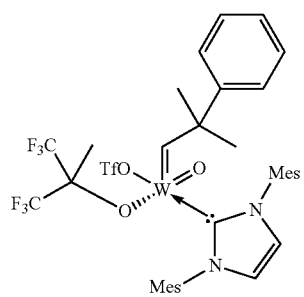
W13 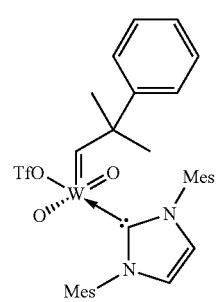
W14 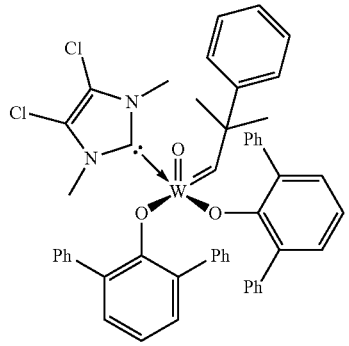
W15 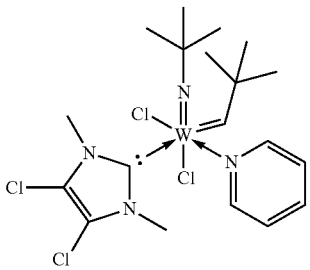
W16 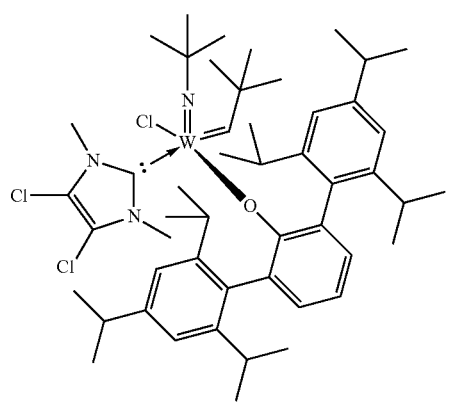

-continued

W17

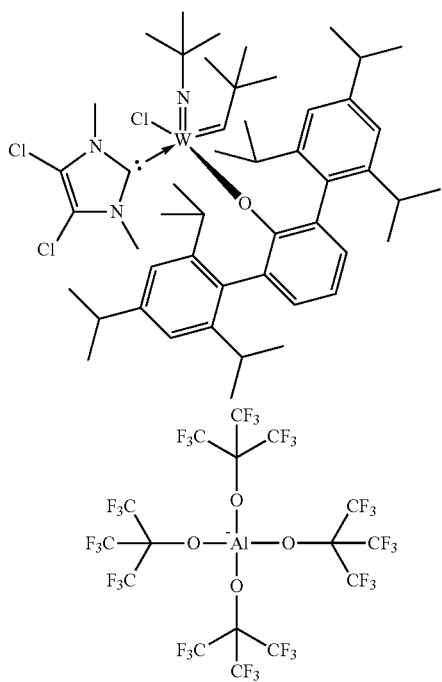

Mes=mesityl, OTf⁻=CF$_3$SO$_3$⁻, BAr$^F$=tetrakis(3,5-bis(trifluoromethyl)phenyl)borate, Me=methyl.

Example 38 (Preparation of W(O)Cl$_2$(PPhMe$_2$) (IMes)-(CHCMe$_2$Ph)) (W2)

W(O)Cl$_2$(PPhMe$_2$)(CHCMe$_2$Ph) (2.42 g, 3.56 mmol) was dissolved in 50 mL of toluene. A solution of 1,3-bis(2,4,6-trimethylphenyl)imidazol-2-ylidene (1.08 g, 3.56 mmol, 1 equiv.) in 10 mL of toluene was prepared. Both solutions were cooled at −40° C. for 30 min. The cold NHC solution was added gradually to the stirred solution of W(O)Cl$_2$(PPhMe$_2$)$_2$(CHCMe$_2$Ph). The reaction mixture was stirred at room temperature for 2 h. The slightly cloudy solution was filtered through Celite and the solvent was removed under reduced pressure. An orange oil was obtained. The oil was taken up in 50 mL of dimethyl ether and filtered rapidly once again. A yellow solid now begins to precipitate out. The solution was stored in the refrigerator at −40° C. overnight. Yield: 2.63 g (87%) of a pale yellow solid. $^1$H NMR (400 MHz, C$_6$D$_6$): δ=1.28 (d, 3H, PMe$_2$, J$_{P-H}$=10.1 Hz), 1.32 (s, 3H, CMe$_2$Ph), 1.59 (s, 3H, CMe$_2$Ph), 1.66 (d, 3H, PMe$_2$, J$_{P-H}$=10.3 Hz), 2.11 (s, 6H, Mes-Me), 2.24 (s, br, 6H, Mes-Me), 2.38 (s, br, 6H, Mes-Me), 6.16 (s, br, 2H, N—CH=CH—N), 6.80 (s, br, 2H, Mes-Ar), 6.83 (s, br, 2H, Mes-Ar), 6.87 (m, 3H, CMe$_2$Ph), 6.99-7.09 (m, 5H, Ar), 7.25 (m, 2H, Ar), 7.46 (m, 2H, PMe$_2$Ph), 11.9 (d, 1H, J$_{P-H}$=3.6 Hz); $^{13}$C NMR (100 MHz, C$_6$D$_6$): δ=14.0 (d, PMe$_2$, J$_{C-P}$=34.8), 15.3 (d, PMe$_2$, J$_{C-P}$=31.2), 19.5 (o-Mes-Me), 19.7 (o-Mes-Me), 21.2 (p-Mes-Me), 31.1 (CMe$_2$Ph), 32.9 (CMe$_2$Ph), 51.7 (CMe$_2$Ph), 124.4 (br, N—C=C—N), 126.0 (p-CMe$_2$Ph), 126.8 (o-CMe$_2$Ph), 128.2 (m-CMe$_2$Ph), 128.5 (p-PPh), 129.3 (d, m-PPh, J$_{C-P}$=2.0 Hz), 129.5 (d, o-PPh, J$_{C-P}$=2.7 Hz), 131.4 (d, ipso-PPh, J$_{C-P}$=8.6 Hz), 135.9 (br), 137.6 (m-Mes), 138.7 (o-Mes), 152.3 (ipso-CMe$_2$Ph), 193.1 (d, N—C—N, J$_{C-P}$=71.1 Hz) 309.5 (W=C, J$_{C-P}$=125.3 Hz); $^{31}$P NMR (160 MHz, C$_6$D$_6$): δ=8.28 (P—W), −33.2 (PMe$_2$Ph). CHN anal. calc. for C$_{39}$H$_{47}$Cl$_2$N$_2$OPW: C, 55.40; H, 5.60; N, 3.31. Found: C, 55.58; H, 5.74; N, 3.32.

Example 39 (Preparation of W(O)(OTf)Cl(PPhMe$_2$) (IMes)-(CHCMe$_2$Ph)) (W3)

W(O)Cl$_2$(PPhMe$_2$)(IMes)(CHCMe$_2$Ph) (0.067 g, 0.08 mmol) was dissolved in 2 mL of dichloromethane and cooled at −40° C. The cold solution was added to solid silver triflate (0.020 g, 1 equiv.) and stirred vigorously. A white precipitate formed. The suspension was stirred with exclusion of light for 30 minutes and filtered through Celite. After the solvent had been removed, the yellow oil was taken up once again in 1 mL of dichloromethane and filtered once more. In order to remove residues of silver chloride, the step has to be repeated a few times. Yield: 0.061 g (81%) of a pale yellow solid. $^1$H NMR (400 MHz, CD$_2$Cl$_2$): δ=0.97 (s, 3H, CMe$_2$Ph), 1.15 (d, 3H, PMe$_2$, J$_{P-H}$=10.52 Hz), 1.36 (d, 3H, PMe$_2$, J$_{P-H}$=10.53 Hz), 1.81 (s, 3H, CMe$_2$Ph), 1.97 (s, 6H, Mes-Me), 2.16 (s, 6H, Mes-Me), 2.39 (s, 6H, Mes-Me), 6.92 (s, br, 2H, Mes-Ar), 6.93-7.10 (m, 2H, Ar), 7.11 (s, br, 2H, Mes-Ar), 7.11-7.16 (m, 2H, Ar), 7.21-7.38 (m, 6H, Ar), 7.40 (s, 2H, N—CH=CH—N), 7.4-7.5 (m, 1H, Ar), 10.08 (d, 1H, W=CH, J$_{P-H}$=2.2 Hz); $^{13}$C NMR (100 MHz, CD$_2$Cl$_2$): δ=11.60 (d, PMe$_2$, J$_{C-P}$=35.4), 13.9 (d, PMe$_2$, J$_{C-P}$=31.2), 18.7 (p-Mes-Me), 21.5 (o-Mes-Me), 28.7 (CMe$_2$Ph), 32.7 (CMe$_2$Ph), 52.0 (CMe$_2$Ph), 126.1, 126.3 (br, N—C=C—N), 128.0, 128.7, 129.5, 129.5, 129.6, 129.6, 130.5 (d, PPh, J$_{C-P}$=26.3 Hz), 131.4 (d, PPh, J$_{C-P}$=9.3 Hz), 131.7 (d, PPh, J$_{C-P}$=2.8 Hz), 134.5 (p-Mes), 135.4 (m-Mes), 136.5 (o-Mes), 141.4, 147.9 (ipso-CMe$_2$Ph), 191.1 (d, N—C—N, J$_{C-P}$=55.1 Hz), 302.4 (d, W=C, J$_{C-H}$=116.9 Hz, J$_{C-P}$=9.5 Hz); 19F NMR (375 MHz, CD$_2$Cl$_2$) δ=−78.82 (OSO$_2$CF$_3$); $^{31}$P NMR (160 MHz, CD$_2$Cl$_2$): δ=17.34. CHN anal. calc. for C$_{40}$H$_{48}$ClF$_3$N$_2$O$_4$PSW: C, 50.04; H, 5.04; N, 2.92. Found: C, 49.34; H, 4.80; N, 2.89.

Example 40 (Preparation of W(O)(OCCH$_3$(CF$_3$)$_2$) Cl(IMes)-(CHCMe$_2$Ph)) (W4))

In the glovebox, W(O)Cl$_2$(PPhMe$_2$)(IMes)(CHCMe$_2$Ph) (0.568 g, 0.67 mmol) was initially charged in a 25 mL Schlenk flask. The compound was dissolved in 10 mL of toluene and at −40° C. for 30 min. Subsequently, LiOCMe (CF$_3$)$_2$ (0.170 g, 0.67 mmol, 1 equiv.) was added in solid form. The suspension turned dark orange. After it had been stirred at room temperature for 3 h, the suspension was filtered and the solvent was removed. A dark orange oil was obtained. This was washed with 5 mL of n-pentane and taken up in a minimal amount of diethyl ether. The solution was stored at −40° C. overnight. In the course of this, a pale yellow solid precipitated out. The solids were filtered off and the mother liquor was concentrated further in order to precipitate a second fraction of the product. The combined fractions can be recrystallized once more from diethyl ether. The product is obtained as a pale yellow solid or as yellow crystals (0.470 g, 82%). $^1$H NMR (400 MHz, C$_6$D$_6$): δ=1.49 (m, 3H, CMe(CF$_3$)$_2$), 1.54 (s, 3H, CMe$_2$Ph), 1.60 (s, 3H, CMe$_2$Ph), 1.91 (s, 6H, Mes-Me), 2.05 (s, 6H, Mes-Me), 2.14 (s, 6H, Mes-Me), 5.97 (s, 2H, N—CH=CH—N), 6.39 (s, br, 2H, Mes-Ar), 6.69 (s, br, 2H, Mes-Ar), 7.00 (m, 5H, Ar), 9.76 (s, 1H, W=CH); $^{13}$C NMR (100 MHz, CD$_2$Cl$_2$): δ=17.3 (OCMe(CF$_3$)$_2$), 19.1 (o-Mes-Me), 19.1 (o-Mes-Me), 21.3 (p-Mes-Me), 28.8 (CMe$_2$Ph), 33.4 (CMe$_2$Ph), 50.3 (CMe$_2$Ph), 78.4 (m, CMe(CF$_3$)$_2$, 3H), 124.7 (N—C=C—N), 126.3 (p-CMe$_2$Ph), 126.6 (o-CMe$_2$Ph), 128.5

(m-C$\underline{Me_2}$Ph), 129.9, 135.6 (p-Mes), 135.9 (m-Mes), 137.2 (o-Mes), 140.5 (ipso-Mes), 151.0 ($\underline{C}$Me$_2$Ph), 192.1 (N—C—N), 282.1 (W=C, $J_{C-H}$=121.3 Hz); $^{19}$F NMR (375 MHz, C$_6$D$_6$): δ=−76.70-78.00 (dq). CHN anal. calc. for C$_{35}$H$_{39}$ClF$_6$N$_2$O$_2$W: C, 49.28; H, 4.61; N, 3.28. Found: C, 49.24; H, 4.73; N, 3.28.

Example 41 (Preparation of W(O)(2,6-diphenylphenoxide)-Cl(IMes)(CHCMe$_2$Ph)) (W5)

W(O)Cl$_2$(PPhMe$_2$)(IMes)(CHCMe$_2$Ph) (0.850 g, 1 mmol) was dissolved in 30 mL of toluene. Lithium 2,6-diphenylphenoxide (0.266 g, 1.06 mmol, 1.05 equiv.) was added in solid form at room temperature. The solution turned cloudy. The reaction mixture was stirred at room temperature for 12 h. The toluene was reduced to half the volume and the colorless precipitate was filtered off using Celite. The filtrate was concentrated further until precipitate formed again. The solution was stored in a refrigerator at −40° C. overnight. A yellow-orange solid was filtered off (0.830 g, 90%). $^1$H NMR (400 MHz, CD$_2$Cl$_2$): δ=1.33 (s, 3H, C$\underline{Me_2}$Ph), 1.40 (s, 6H, Mes-Me), 1.55 (s, 3H, C$\underline{Me_2}$Ph), 1.80 (s, 6H, Mes-Me), 2.33 (s, 6H, Mes-Me), 6.66 (m, 2H, Ar), 6.81 (s, 2H, N—$\underline{CH=CH}$—N), 6.83 (s, br, 2H, Mes-Ar), 6.86 (m, 1H, Ar), 6.89 (br, 2H, Mes-Ar), 6.97 (m, 4H, Ar), 7.09 (m, 1H, Ar), 7.17 (m, 2H, Ar), 7.22-7.36 (m, 5H, Ar), 7.40 (m, 2H, Ar), 7.81 (m, 2H, Ar), 9.90 (s, 1H, W=CH); $^{13}$C NMR (100 MHz, CD$_2$Cl$_2$): δ=18.6 (o-Mes-$\underline{Me}$), 19.2 (o-Mes-$\underline{Me}$), 21.4 (p-Mes-$\underline{Me}$), 29.6 (C$\underline{Me_2}$Ph), 32.3 ($\underline{C}$Me$_2$Ph), 50.3 ($\underline{C}$Me$_2$Ph), 120.5, 125.5, 126.4, 126.5, 127.1, 128.4, 129.2, 129.3, 129.5, 130.5, 130.8, 131, 131.8, 133.2, 134.8, 135.4, 135.4, 136.6, 139.8, 141.1, 142, 150.8 (ipso-C$\underline{Me_2}$Ph), 159.6 (ipso-O—Ar), 191.6 (N—C—N), 288 (W=C, $J_{CH}$=123.1 Hz), 298.2 ($J_{C-H}$=123.3 Hz). CHN anal. calc. for C$_{49}$H$_{49}$ClN$_2$O$_2$W: C, 64.16; H, 5.38; N, 3.05. Found: C, 64.16; H, 5.41; N, 3.13.

Example 42 (Preparation of [W(O)(CHCMe$_2$Ph)(IMes)(OTf)-(MeCN)$_2$ B(3,5-(CF$_3$)$_2$—C$_6$H$_3$)$_4$]) (W6)

The compound was prepared in situ, immediately prior to the catalyses conducted. W(O)(OTf)Cl(PPhMe$_2$)(IMes)-(CHCMe$_2$Ph) was dissolved in 5 mL of dichloromethane and cooled at −40° C. for 30 min. Subsequently, Ag(MeCN)$_2$B(Ar$^F$)$_4$ (2.05 equiv.) was added in solid form. A colorless precipitate formed immediately. The suspension was stirred with exclusion of light at room temperature for 30 min. Thereafter, the precipitate was filtered off using Celite. The intense yellow solution was used as catalyst stock solution. $^1$H NMR (400 MHz, CD$_2$Cl$_2$): δ=1.49 (s, 3H, C$\underline{Me_2}$Ph), 1.92 (s, 3H, C$\underline{Me_2}$Ph), 2.03 (s, 6H, $\underline{Me}$CN), 2.12 (s, 6H, Mes-Me), 2.18 (s, 6H, Mes-Me), 2.37 (s, 6H, Mes-Me), 6.96 (s, br, 2H, Mes-Ar), 7.10 (s, br, 2H, Mes-Ar), 7.20-7.38 (m, 5H, Ar), 7.42 (s, 2H, N—$\underline{CH=CH}$—N), 7.63 (s, br, 4H, BAr$^F$), 7.80 (s, br, 8H, BAr$^F$), 11.47 (s, 1H, W=CH); $^{13}$C NMR (100 MHz, CD$_2$Cl$_2$): δ=2.9 ($\underline{Me}$CN), 18.5 (o-Mes-$\underline{Me}$), 19.0 (o-Mes-$\underline{Me}$), 21.4 (p-Mes-$\underline{Me}$), 29.2 (C$\underline{Me_2}$Ph), 31.0 ($\underline{C}$Me$_2$Ph), 53.5 ($\underline{C}$Me$_2$Ph), 118.2 (sept, $J_{C-F}$=3.8 Hz, p-CH (BAr$^F$)), 125.3 (q, $J_{C-F}$=272.4 Hz, 4×2CF$_3$ (BAr$^F$)), 126.9, 127.2, 127.4, 129.2, 129.7 (qq, $J_{C-F}$=31.6 Hz, $J_{C-B}$=2.7 Hz, 4×C—CF3 (BAr$^F$)), 129.8, 130.1, 130.9, 132.4, 134.6, 135.5 (s, br, 4×2C, o-CH (BAr$^F$)), 136.9, 141.7 (ipso-Mes), 148.8 (ipso-C$\underline{Me_2}$Ph), 162.4 (q, $J_{C-H}$=49.8 Hz, 4×BC(BAr$^F$)), 187.0 (N—C—N), 324.3 (W=C, $J_{C-H}$=125.3 Hz); $^{19}$F NMR (375 MHz, CD$_2$Cl$_2$): δ=−62.77 (BAr$^F$), −77.82 (O—SO$_2$CF$_3$).

Example 43 (Preparation of [W(O)(CHCMe$_2$Ph)(IMes)-OCCH$_3$(CF$_3$)$_2$) B(3,5-(CF$_3$)$_2$—C$_6$H$_3$)$_4$]) (W7)

W(O)(OCCH$_3$(CF$_3$)$_2$)Cl(IMes)(CHCMe$_2$Ph) (0.032 g, 0.0375 mmol) was dissolved in 5 mL of dichloromethane and cooled at −40° C. for 30 min. The solution was added to solid NaB(Ar$^F$)$_4$ (0.0333 g, 1 equiv.). The suspension was stirred at room temperature for 30 min. A colorless precipitate formed. The solution was stored at −40° C. for 30 min and filtered cold through a glass fiber filter. The filtrate was concentrated under reduced pressure to one third of the volume and filtered once again. After the solvent had been removed, an orange oil was obtained. The latter was stirred with n-pentane until an orange solid formed. The pentane phase was decanted and the solids were dried under reduced pressure. Yield: 0.055 g (87%). $^1$H NMR (400 MHz, CD$_2$Cl$_2$): δ=1.29 (s, 3H, C$\underline{Me_2}$Ph), 1.32 (sept, 3H, C$\underline{CH_3}$(CF$_3$)$_2$), 1.64 (s, 3H, C$\underline{Me_2}$Ph), 1.94 (s, 6H, Mes-Me), 2.05 (s, 6H, Mes-Me), 2.37 (s, 6H, Mes-Me), 7.02 (s, br, 2H, Mes-Ar), 7.16 (s, br, 2H, Mes-Ar), 7.18-7.31 (m, 5H, Ar), 7.57 (s, br, 4H, BAr$^F$), 7.68 (s, 2H, N—$\underline{CH=CH}$—N), 7.74 (s, br, 8H, BAr$^F$), 10.52 (s, 1H, W=CH); $^{13}$C NMR (100 MHz, CD$_2$Cl$_2$): δ=17.8 (o-Mes-$\underline{Me}$), 17.9 (o-Mes-$\underline{Me}$), 19.3 (OC$\underline{Me}$(CF$_3$)$_2$), 21.5 (p-Mes-Me), 29.4 (C$\underline{Me_2}$Ph), 31.9 ($\underline{C}$Me$_2$Ph), 52.7 ($\underline{C}$Me$_2$Ph), 86.3 (m, O$\underline{C}$Me(CF$_3$)$_2$), 118.1 (sept, $J_{C-F}$=3.8 Hz, p-CH (BAr$^F$)), 123.8 (q, $J_{C-F}$=273.4 Hz, 4×2CF$_3$ (BAr$^F$)), 126.3 (N—C=C—N), 127.9 (o-Ar), 128.6 (p-Ar), 129.4 (m-Ar), 129.5 (qq, $J_{C-F}$=31.6 Hz, $J_{C-B}$=2.7 Hz, 4×C—CF3 (BAr$^F$)), 131.1 (m-Mes), 131.2 (m-Mes), 133.0 (o-Mes), 134.3 (o-Mes), 135.3 (p-Mes), 135.4 (s, br, 4×2C, o-CH (BAr$^F$)), 143.6 (ipso-Mes), 147.6 (ipso-C$\underline{Me_2}$Ph), 162.4 (q, $J_{C-B}$=49.8 Hz, 4×BC(BAr$^F$)), 181.8 (N—C—N), 297.3 (W=C, $J_{C-H}$=123.3 Hz); $^{19}$F NMR (375 MHz, CD$_2$Cl$_2$): δ=−62.86 (BAr$^F$), −78.61 (dq). CHN anal. calc. for C$_{67}$H$_{51}$BF$_{30}$N$_2$O$_2$W: C, 47.88; H, 3.06; N, 1.67. Found: C, 47.96; H, 3.279; N, 1.84.

Example 44 (Preparation of [W(O)(CHCMe$_2$Ph)(IMes)(2,6-diphenylphenoxide) B(3,5-(CF$_3$)$_2$—C$_6$H$_3$)$_4$)]) (W8)

W(O)(2,6-diphenylphenoxide)Cl(IMes)(CHCMe$_2$Ph) (0.0171 g, 0.0186 mmol) was dissolved in 5 mL of dichloromethane and cooled at −40° C. for 30 min. The solution was added to solid NaB(Ar$^F$)$_4$ (0.0165 g, 1 equiv.). The suspension was stirred for 30 minutes. A colorless precipitate formed. The reaction mixture was cooled at −40° C. for 30 min and filtered. The filtrate was concentrated down to one third and filtered once again. After the solvent had been removed, a yellow foam was obtained. This was stirred with n-pentane until a yellow precipitate formed. The pentane phase was decanted and the solids were dried under reduced pressure. Yield 0.029 g (89%). $^1$H NMR (400 MHz, CD$_2$Cl$_2$): δ=0.72 (s, 3H, C$\underline{Me_2}$Ph), 1.58 (s, 3H, C$\underline{Me_2}$Ph), 1.67 (s, 6H, Mes-Me), 1.71 (s, 6H, Mes-Me), 2.34 (s, 6H, Mes-Me), 6.83 (s, br, 2H, Mes-Ar), 6.99 (s, br, 2H, Mes-Ar), 7.01-7.09 (m, 4H), 7.17-7.27 (m, 12H), 7.30-7.40 (m, 4H), 7.45-7.52 (m, 1H), 7.56 (s, br, p-CH (BAr$^F$)), 7.73 (s, 8H, o-CH (BAr$^F$)), 11.82 (s, 1H, W=CH); $^{13}$C NMR (100 MHz, CD$_2$Cl$_2$, MeCN adduct): δ=2.5 ($\underline{Me}$CN), 18.6 (o-Mes-$\underline{Me}$), 18.9 (o-Mes-$\underline{Me}$), 21.4 (p-Mes-$\underline{Me}$), 30.1 (C$\underline{Me_2}$Ph), 30.5 ($\underline{C}$Me$_2$Ph), 52.1 ($\underline{C}$Me$_2$Ph), 118.1 (sept, $J_{C-F}$=3.8 Hz, p-CH (BAr$^F$)), 123.5 (Me$\underline{C}$N), 123.8 (q, $J_{C-F}$=273.4 Hz, 4×2CF$_3$ (BAr$^F$)), 126.7 (br, N—C≡C—N), 126.8, 127.2, 128.8, 129.5 (qq, J$_{C-F}$=31.6 Hz, J$_{C-B}$=2.7 Hz, 4×C—CF3 (BAr$^F$)), 129.9, 130.0, 135.4, 135.4 (s, br, 4×2C, o-CH (BAr$^F$)), 135.5, 135.6, 141.4 (ipso-Mes), 147.3 (ipso-CMe$_2$Ph), 157.5 (ipso-O—Ar), 162.4 (q, J$_{C-B}$=49.8 Hz, 4×BC (BAr$^F$)), 188.6 (N—C—N), 309.9 (W≡C, J$_{C-H}$=121.2 Hz); $^{19}$F NMR (375 MHz, CD$_2$Cl$_2$): δ=−62.87 (BAr$^F$). CHN anal. calc. for C$_{81}$H$_{61}$BF$_{24}$N$_2$O$_2$W: C, 55.75; H, 3.52; N, 1.61. Found: C, 55.69; H, 3.913; N, 1.72.

Example 45 (Preparation of [W(O)(CHCMe$_2$Ph)(IMes)-(OCCH$_3$(CF$_3$)$_2$)(MeCN)$_2$ B(3,5-(CF$_3$)$_2$—(C$_6$H$_3$)$_4$]) (W9)

The compound was prepared in situ, immediately before the catalyses conducted. W(O)(OCCH$_3$(CF$_3$)$_2$)Cl(IMes)-(CHCMe$_2$Ph) was dissolved in 5 mL of dichloromethane and cooled at −40° C. for 30 minutes. Subsequently, Ag(MeCN)$_2$B(Ar$^F$)$_4$ (1.0 equiv.) was added in solid form. A colorless precipitate formed immediately. The suspension was stirred with exclusion of light at room temperature for 30 min. Thereafter, the precipitate was filtered off using Celite. The intense yellow solution was utilized as catalyst stock solution.

Example 46 (Preparation of [W(O)(CHCMe$_2$Ph)(IMes)(2,6-diphenylphenoxide)(MeCN)$_2$ B(3,5-(CF$_3$)$_2$—(C$_6$H$_3$)$_4$]) (W10)

The compound was prepared in situ, immediately before the catalyses conducted. W(O)(2,6-diphenylphenoxide)-Cl(IMes)(CHCMe$_2$Ph) was dissolved in 5 mL of dichloromethane and cooled at −40° C. for 30 minutes. Subsequently, Ag(MeCN)$_2$B(Ar$^F$)$_4$ (1.0 equiv.) was added in solid form. A colorless precipitate formed immediately. The suspension was stirred with exclusion of light at room temperature for 30 min. Thereafter, the precipitate was filtered off using Celite. The intense yellow solution was utilized as catalyst stock solution.

Example 47 (Preparation of [W(O)Cl$_2$(IMes)(CHCMe$_2$Ph)) (W11)

W(O)(2,6-diphenylphenoxide)Cl(IMes)(CHCMe$_2$Ph) (0.023 g, 0.249 mmol) was dissolved in 2 mL of acetonitrile and cooled at −40° C. for 30 minutes. Subsequently, a cold solution of AlCl$_3$ (0.0033 g, 0.249 mmol, 1 equiv.) in 1 mL of acetonitrile was added. The solution turned intense yellow and was stirred at room temperature for 3 h. Thereafter, the solvent was removed and the oily residue was taken up in 1 mL of dichloromethane. The solution was filtered and concentrated to 0.3 mL. After a few days, yellow crystals of the product formed. Yield: 0.013 g (74%).

Example 48 (Preparation of W(O)(OTf)(OCCH$_3$(CF$_3$)$_2$)(IMes)-(CHCMe$_2$Ph)) (W12)

W(O)(OCCH$_3$(CF$_3$)$_2$)Cl(IMes)(CHCMe$_2$Ph) (0.0495 g, 0.058 mmol) was dissolved in 2 mL of dichloromethane and cooled at −40° C. for 30 min. Silver triflate (0.015 g, 0.058 mmol, 1 equiv.) was added to the cold solution. A colorless precipitate was immediately observed. The suspension was stirred with exclusion of light for 1 h and filtered through Celite. The solvent was removed. A yellow oil remained, which was taken up in 1 mL of dichloromethane and filtered once again. This step was repeated a few times in order to remove residues of silver chloride. The product is obtained as a yellow solid. Yield: 0.041 g (74%). $^1$H NMR (400 MHz, CD$_2$Cl$_2$): δ=0.74 (s, 3H, CMe$_2$Ph), 0.81 (s, 3H, CMe(CF$_3$)$_2$), 1.45 (s, 3H, CMe$_2$Ph), 2.13 (s, 6H, Mes-Me), 2.18 (s, 6H, Mes-Me), 2.31 (s, 6H, Mes-Me), 6.96 (s, br, 2H, Mes-Ar), 7.03 (s, br, 2H, Mes-Ar), 7.05-7.11 (m, 1H, Ar), 7.14-7.25 (m, 4H, Ar), 7.26 (s, 2H, N-CH═CH—N), 10.69 (s, 1H, W═CH); $^{13}$C NMR (100 MHz, CD$_2$Cl$_2$) δ=17.6 (OCMe(CF$_3$)$_2$), 18.4 (o-Mes-Me), 18.5 (o-Mes-Me), 21.3 (p-Mes-Me), 29.0 (CMe$_2$Ph), 29.9 (CMe$_2$Ph, 50.8 (CMe$_2$Ph), 82.3 (m, CMe(CF$_3$)$_2$), 125.8, 126.1, 126.5, 128.6, 130.4, 130.4, 136.4 (p-Mes), 137.1 (m-Mes), 141.7 (ipso-Mes), 150.9 (CMe$_2$Ph), 186.0 (N—C—N), 278.2 (W═C, J$_{C-H}$=127.1 Hz); $^{19}$F NMR (375 MHz, C$_6$D$_6$): δ=−77.71 (s, br, OSO$_2$CF$_3$), −77.76 (m, br, OCCH$_3$(CF$_3$)$_2$).

Example 49 (Preparation of W(O)(OTf)$_2$(IMes)(CHCMe$_2$Ph)) (W13)

W(O)Cl$_2$(PPhMe$_2$)(IMes)(CHCMe$_2$Ph) (0.26 g, 0.83 mmol) was dissolved in 8 mL of dichloromethane. The solution was cooled at −40° C. for 30 min. While stirring, Silver triflate (0.200 g, 0.766 mmol, 2.01 equiv.) was added in solid form. A colorless solid immediately precipitated out. The suspension was stirred with exclusion of light at room temperature for 1 h. In the course of this, the color changed to yellow. The solution was filtered through Celite. The solvent was removed. A pale yellow foam was obtained. The latter was dissolved in a small amount of dichloromethane and filtered once again. This step was repeated a few times in order to remove silver chloride residues. The crude product can be recrystallized from dichloromethane/diethyl ether. The product is obtained as a yellow crystalline solid. Yield: 0.303 g (85%).

Example 50 (Preparation of W(O)(2,6-diphenylphenoxide)$_2$ (1,3-Me$_2$-4,5-Cl$_2$-imidazol-2-ylidene)(CHCMe$_2$Ph)) (W14)

W(O)(2,6-diphenylphenoxide)$_2$(PMePh$_2$)(CHCMe$_2$Ph) (0.12 g, 0.117 mmol) was dissolved in 8 mL of toluene. 1,3-Me$_2$-4,5-Cl$_2$-imidazol-2-ylidene-AgI (0.048 g, 0.12 mmol, 1.01 equiv.) was added in solid form. The suspension was kept in an ultrasound bath at 70° C. for 1 hour. Subsequently, the suspension was filtered through Celite and the solvent was removed. The pale yellow solid was taken up in 4 mL of dichloromethane and filtered once more. The solvent was removed and the oily solid was washed with n-pentane. The product was obtained as a pale orange solid. Yield: 0.1 g (86%). $^1$H NMR (400 MHz, C$_6$D$_6$): δ=1.08 (s, 3H, CMe$_2$Ph), 1.44 (s, 3H, CMe$_2$Ph), 6.73-6.82 (m, 6H, Ar), 6.96-7.03 (m, 8H, Ar), 7.05-7.12 (m, 6H, Ar), 7.17-7.28 (m, 12H, Ar), 7.47 (d, 2H, p-Ar, J=7.56 Hz), 7.47 (m, 4H, p-Ar), 10.25 (s, 1H, W═CH); $^{13}$C NMR (100 MHz, C$_6$D$_6$): δ=29.4 (CMe$_2$Ph), 31.5 (CMe$_2$Ph), 36.3 (Me-NHC), 48.5 (CMe$_2$Ph), 117.1 (NC═CN), 125.6, 125.8, 126.4, 126.8, 128.9, 129.8, 130.4, 131.1, 132.1, 133.2, 133.4, 133.9, 140.6 (ipso-Ar), 142.0 (ipso-Ar), 151.5 (ipso-CMe$_2$Ph), 157.8 (ipso-O—Ar), 163.4 (ipso-O—Ar), 191.3 (N—C—N), 279.5 (W═C, J$_{C-H}$=124.0 Hz).

Example 51 (Preparation of W(NtBu)(Cl)$_2$(1,3-Me$_2$-4,5-Cl$_2$-imidazol-2-ylidene)(pyridine)(CHCMe$_3$)) (W15)

W(NtBu)(Cl)$_2$ (pyridine)$_2$(CHCMe$_3$) (0.2 g, 0.36 mmol) was dissolved in 8 mL of dichloroethane. 1,3-Me$_2$-4,5-Cl$_2$-imidazol-2-ylidene-AgI (0.145 g, 0.36 mmol, 1.0 equiv.)

was added in solid form. The suspension was kept in an ultrasound bath at 70° C. for 1 hour. Subsequently, the suspension was filtered through Celite and the solvent was removed. The pale yellow solid was taken up in 4 mL of dichloromethane and filtered once more. The solvent was removed and the solids were washed with n-pentane. The product was obtained as a pale orange solid. Two isomers form in equal proportions. Yield: 0.19 g (82%). $^1$H NMR (400 MHz, CD$_2$Cl$_2$): δ=1.21 (s, 9H, tBu), 1.28 (s, 9H, tBu), 1.38 (s, 9H, tBu), 1.41 (s, 9H, tBu), 3.76 (s, 6H, Me$_2$-NHC), 4.21 (s, 6H, Me$_2$-NHC), 7.28 (m, 2H, pyr), 7.41 (m, 2H, pyr), 7.68 (m, 1H, pyr), 7.86 (m, 1H, pyr), 8.60 (m, br, 2H, pyr), 9.40 (m, 2H, pyr), 10.58 (s, 1H, W=CH), 12.0 (s, 1H, W=CH); $^{13}$C NMR (100 MHz, CD$_2$Cl$_2$): δ=15.7, 31.0, 31.4, 31.4, 32.6, 34.3, 34.8, 39.2, 40.4, 44.8, 45.4, 66.2 (CMe$_3$), 69.6 (CMe$_3$), 118.9, 119.0, 124.2, 124.8, 124.9, 136.3, 139.1, 139.4, 150.5, 156.8, 157.1, 191.0 (N—C—N), 191.2 (N—C—N), 279.9 (W=CH), 301.0 (W=CH).

Example 52 (Preparation of W(NtBu)(Cl)(1,3-Me$_2$-4,5-Cl$_2$-imidazol-2-ylidene)(OHIPT)(CHCMe$_3$)) (W16)

W(NtBu)(Cl)$_2$(1,3-Me$_2$-4,5-Cl$_2$-imidazol-2-ylidene)-(pyridine)(CHCMe$_3$) (0.15 g, 0.234 mmol) was dissolved in 8 mL of benzene. Lithium 2,6-di(2,4,6-triisopropylphenyl) phenoxide (0.118 g, 0.234 mmol, 1.0 equiv.) was added in solid form. The solution was stirred at room temperature overnight. A colorless precipitate formed. Subsequently, the suspension was filtered through Celite and the solvent was removed. The dark orange foam was taken up in 4 mL of toluene and filtered once more. The solvent was removed and the solids were recrystallized from n-pentane. The product was obtained as an orange solid. Yield: 0.13 g (87%). $^1$H NMR (400 MHz, C$_6$D$_6$): δ=0.72 (d, 3H, iPr), 1.00 (m, 6H, iPr), 1.14 (d, 3H, iPr), 1.20 (s, 9H, tBu), 1.24 (s, 9H, tBu), 1.26 (m, 6H, iPr), 1.30 (m, 9H, tBu), 1.36 (m, 6H, iPr), 1.66 (m, 6H, iPr), 2.70-3.30 (m, 10H, Me$_2$-NHC, CH-iPr), 3.93 (m, 2H, CH-iPr), 6.9 (m, 1H, Ar), 7.02 (m, 1H, Ar), 7.13 (m, 1H, Ar), 7.16 (m, 1H, Ar), 7.26 (m, 2H, Ar), 7.40 (m, 1H, Ar), 10.37 (s, 1H, W=CH); $^{13}$C NMR (100 MHz, C$_6$D$_6$): δ=14.3, 22.3, 22.7, 22.9, 24.2, 24.5, 24.7, 24.8, 25.2, 25.5, 27.1, 27.6, 30.4, 31.0, 31.5, 34.2, 34.5, 34.6, 34.8, 43.8, 68.1 (CMe$_3$), 118.2, 119.7, 120.1, 121.9, 122.7, 131.5, 132.0, 132.4, 138.1, 138.4, 147.2, 147.3, 147.4, 148.1, 149.5, 149.9, 162.0, 192.0 (N—C—N), 281.9 (W=CH).

Example 53 (Preparation of [W(NtBu)(1,3-Me$_2$-4,5-Cl$_2$-imidazol-2-ylidene)(OHIPT)(CHCMe$_3$) AlpftBu]) (W17)

W(NtBu)(Cl)(1,3-Me$_2$-4,5-Cl$_2$-imidazol-2-ylidene) (OHIPT)-(CHCMe$_3$) (0.0331 g, 0.0323 mmol) was dissolved in 3 mL of dichloromethane. Lithium tetrakis(nonafluoro-t-butoxy)aluminate (LiAlpftBu, 0.0315 g, 0.0323 mmol, 1.0 equiv.) was added in solid form. The solution was stirred at room temperature for 1 h. A colorless precipitate formed. At the same time, the solution turned intense yellow. Subsequently, the suspension was filtered through Celite and the solvent was removed. The yellow foam was taken up in 4 mL of toluene and filtered once more. The solvent was removed and the yellow oil was stirred with n-pentane. A yellow solid formed. The product was filtered off and dried under reduced pressure. Yield: 0.055 g (87%). $^1$H NMR (400 MHz, CD$_2$Cl$_2$): δ=0.81 (d, 6H, iPr), 0.95 (d, 6H, iPr), 0.99 (d, 6H, iPr), 1.01 (s, 9H, tBu), 1.02 (d, 6H, iPr), 1.09 (s, 9H, tBu), 1.23 (d, 12H, iPr), 2.49 (sept, 2H, CH-iPr), 2.58 (sept, 2H, CH-iPr), 2.89 (sept, 2H, CH-iPr), 3.29 (s, 6H, Me$_2$-NHC), 7.0 (m, 2H, Ar), 7.03 (m, 1H, Ar), 7.05 (s, 1H, Ar), 7.08 (m, 2H, Ar), 7.15 (m, 1H, Ar), 10.74 (s, 1H, W=CH); $^{13}$C NMR (100 MHz, CD$_2$Cl$_2$): δ=24.2, 24.4, 24.5, 24.6, 24.8, 31.6, 32.7, 33.6, 34.7, 40.2, 47.2, 74.4, 120.4, 122.0, 122.3, 122.8, 123.3, 124.9, 131.8, 132.6, 133.2, 147.5, 147.8, 149.9, 158.6, 178.0, 289.0 (W=CH); $^{19}$F NMR (375 MHz, CD$_2$Cl$_2$): δ=−75.72 (s, CF$_3$).

Example 54 (General Method for In Situ Catalyst Syntheses)

The tungsten oxo precursors W3-W5 (about 0.05 mmol) were dissolved in 2 mL of 1,2-dichloroethane. An equimolar amount of Ag(MeCN)$_2$B(Ar$^F$)$_4$ (W4, W5) or 2 equiv. (W3) and/or excess AlCl$_3$ was added. The solution was stirred for 30 min and filtered. The filtrate was used as catalyst stock solution.

Example 55 (General Method for Ring-Closing, Homo- and Self-Metatheses)

About 20 mg of the substrate were weighed into a 10 mL screwtop bottle. The appropriate amount of solvent was added (0.1 M solution). Thereafter, 0.5 equiv. of dodecane (internal standard) was added. An aliquot with 1 mg of substrate was taken for the t$_0$ sample. A 0.0005 M catalyst stock solution was prepared. The appropriate amount of stock solution was added to the substrate solution. The solution was stirred at the given temperature for the given period of time. The reactions were stopped by means of air atmosphere and a sample was taken for the GC-MS analysis. The exact monomer/catalyst compositions and the turnover numbers (TONs) determined for these can be found in table 8.

Example 56 (General Method for Cross-Metatheses (CM) with Allyltrimethylsilane)

The same general method was followed as for the ring-closing metatheses (example 53). An additional 10 equivalents of allyltrimethylsilane were merely added to the substrate. The exact monomer/catalyst compositions and the turnover numbers (TONs) determined for these can likewise be found in table 8.

Example 57 (Z-Selective Metathesis)

In a protective gas box, 1-octene (about 22 mg) is weighed into a 4 mL screwtop bottle and dissolved in 1 mL of benzene. While stirring, a solution of W17 (3.6 mg) in benzene (0.2 mL) is added. The mixture is stirred at room temperature for one hour. To monitor the course of the reaction and the selectivity, an aliquot is taken and diluted with undried CDCl$_3$ in order to stop the reaction. The reaction mixture was analyzed by $^1$H NMR (100% conversion >99.9% Z-configured product).

TABLE 8

TONs with AlCl$_3$-activated 3-5 and with cationic complexes W6-W8. Reaction conditions, unless stated otherwise: T = 25° C. in 1,2-dichloroethane for 4 h, ubstrate:catalyst 1:2000

| Substrate | W6 | W7 | W8 | W3[a] | W4[a] | W5[a] |
|---|---|---|---|---|---|---|
| Ring-closing metathesis (RCM) | | | | | | |
| Diallyldiphenylsilane | 4800[c] | 3400[c] | 7600[c] | 0[c] | 0[c] | 0[c] |
| N,N-Diallyl-p-toluenesulfonamide | 1700[c] | 1350 | 1700[b] | 0[c] | 0[c] | 0[c] |
| Octa-1,7-diene | 970[c] | 710 | 1500[b] | 980[c] | 4300[c] | 4700[c] |
| Diallylmalonitrile | 130[c] | 660 | 1400[c] | 0[c] | 0[c] | 0[c] |
| Diallyl ether | 0 | 0 | 5700[c] | 0[c] | 0[c] | 0[c] |
| Diallyl thioether | 4800[c] | 0 | 4900[c] | 4800[c] | 1200 | 1400 |
| 4,4-Dicyanoocta-1,7-diene | 470[c] | 430 | 2600[c] | 0[c] | 0[c] | 0[c] |
| Diethyldiallyl malonate | 1600[c] | 660 | 3200[c] | 0[c] | 0[c] | 0[c] |
| Homometathesis (HM), in brackets = E content (%) | | | | | | |
| Allylbenzene | 200 (55)[c] | 480 (60) | 635 (85)[e] | 640 (55) | 430 (55) | 410 (80) |
| 1-Hexene | 2000 (60)[c] | 1640 (65) | 5400 (85)[e] | 4900 (60)[c] | 5000 (65)[c] | 9800 (80)[e] |
| 1-Octene | 3300 (60)[c] | 1320 (65) | 6100 (85)[e] | 4830 (55)[c] | 5000 (60)[c] | 2000 (80)[c] |
| Allylphenyl sulfide | 0 | 0 | 300 (>95)[d] | 0 | 0 | 280 (>95)[d] |
| Trimethylallylsilane | 4100 (55)[c] | 1710 (55) | 1500 (60) | 0 | 0 | 0 |
| Cross-metathesis (CM)[d] with allyltrimethylsilane, in brackets = E content (%) | | | | | | |
| Hex-5-en-1-yl acetate | 480 (55) | 450 (60) | 500 (80) | 0 | 0 | 0 |
| 4-Octene | 500 (50) | 490 (65) | 500 (80) | 0 | 0 | 0 |
| N-Phenyl-(1-phenyl-but-3-en-1-yl)amine | 200 (60) | 0 | 0 | 0 | 0 | 0 |
| Self-metathesis (SM), in brackets = E content (%) | | | | | | |
| Methyl oleate | 1500 (60) | 0[c] | 10 000 (70)[f] | 0[c] | 0[c] | 0[c] |

[a]activated with excess AlCl$_3$, CH$_2$Cl$_2$, room temperature, catalyst:substrate = 1:5000.
[b]catalyst:substrate = 1:2000, 70° C.
[c]catalyst:substrate = 1:5000, 70° C.
[d]catalyst:substrate = 1:500, 25° C.
[e]catalyst:substrate = 1:10 000, 25° C.
[f]catalyst: substrate = 1:20 000, 70° C.

The invention claimed is:

1. An N-heterocyclic carbene complex of one of the general formulae I-IV

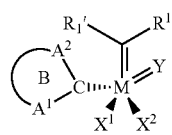

I

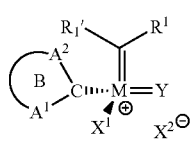

II

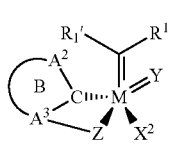

III

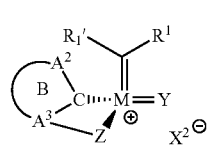

IV wherein:

$A^1$ is $NR^2$ or $PR^2$, $A^2$ is $CR^2R^{2'}$, $NR^2$, $PR^2$, O or S, $A^3$ is N or P, C is a carbene carbon atom, the ring B is an unsubstituted or a mono- or polysubstituted 5- to 7-membered ring which, as well as $A^1$, $A^2$ and/or $A^3$, may contain further heteroatoms in the form of nitrogen, phosphorus, oxygen or sulfur and wherein the substituents may have the definition described for $R^2$, the substituents $R^2$ and $R^{2'}$ are independently H, a linear, partly cyclic or branched $C_1$-$C_{18}$-alkyl, a linear, partly cyclic or branched $C_2$-$C_{18}$-alkenyl, a $C_3$-$C_{12}$-cycloalkyl, a linear, partly cyclic or branched $C_6$-$C_{100}$-polyoxaalkyl, a $C_5$-$C_{14}$-aryl or -heteroaryl radical, a $C_5$-$C_{14}$-aryloxy, a linear, partly cyclic or branched $C_1$-$C_{18}$-perfluoroalkyl, a linear, partly cyclic or branched $C_1$-$C_{18}$-perchloroalkyl, a linear, partly cyclic or branched part-fluorinated $C_1$-$C_{18}$-alkyl, a linear, partly cyclic or branched part-chlorinated $C_1$-$C_{18}$-alkyl, a per- or part-fluorinated $C_6$-$C_{14}$-aryl, a per- or part-chlorinated $C_5$-$C_{14}$-aryl radical, and, when $A^1$ and $A^2$ are each $NR^2$ or $PR^2$, $R^2$ may be the same or different, or $R^2$ and $R^{2'}$ together are a linear or branched $C_1$-$C_{18}$-alkylene, M in the formulae I, II, III and IV is Cr, Mo or W, $X^1$ and $X^2$ in formulae I to IV are the same or different and are selected from the group consisting of halogen, $C_1$-$C_{18}$ carboxylates, $C_1$-$C_{18}$-alkoxides, fluorinated $C_1$-$C_{18}$ alkoxides, $C_1$-$C_{18}$ mono- or polyhalogenated carboxylates, unsubstituted or mono- or polysubstituted $C_6$-$C_{18}$ mono-, bi- or terphenoxides, trifluoromethanesulfonate, and non-coordinating anions, where the substituents on the mono-, bi- or terphenoxides, can be halogen or may have the same definition as $R^2$, Y is oxygen, sulfur, an N-adamantyl, an N-tert-butyl, a $C_6$-$C_{14}$—N-aryl radical, where the aryl radical may be mono- or polysubstituted by halogen, a linear or branched $C_1$-$C_{18}$ alkyl, a linear or branched $C_1$-$C_{18}$ alkyloxy or an unsubstituted or substituted phenyl radical wherein the substituents have the same definition as $R^2$, Z is a linear, partly cyclic or branched $C_1$-$C_{10}$-alkyleneoxy, a linear, partly cyclic or branched $C_1$-$C_{10}$-alkylenethio, a linear, partly cyclic or branched $C_1$-$C_{10}$-alkylene-$NR^2$, a $C_6$-$C_{10}$-aryleneoxy, a per- or part-fluorinated $C_6$-$C_{14}$-aryleneoxy, a per- or part-chlorinated $C_6$-$C_{14}$-aryleneoxy, a per- or part-brominated $C_6$-$C_{14}$-aryleneoxy, a $C_6$-$C_{14}$-arylenethio, a per- or part-fluorinated $C_6$-$C_{14}$-arylenethio, a per- or part-chlorinated $C_6$-$C_{14}$-arylenethio, a per- or part-brominated $C_6$-$C_{14}$-arylenethio, $C_6$-$C_{14}$-arylene-$NR^2$, a per- or part-fluorinated $C_6$-$C_{14}$-arylene-$NR^2$, a per- or part-chlorinated $C_6$-$C_{14}$-arylene-$NR^2$, a per- or part-brominated $C_6$-$C_{14}$-arylene-$NR^2$, a $C_6$-$C_{14}$-arylene-$PR^2$, a per- or part-fluorinated $C_6$-$C_{14}$-arylene-$PR^2$, a per- or part-chlorinated $C_6$-$C_{14}$-arylene-$PR^2$, a per- or part-brominated $C_6$-$C_{14}$-arylene-$PR^2$, a carboxyl, a thiocarboxyl or a dithiocarboxyl group, and $R^1$ and $R^{1'}$ in the formulae I to IV are independently H, aliphatic, aromatic radical, linear or branched $C_1$-$C_{18}$ alkyl group, tert-butyl, $CMe_2Ph$ group, unsubstituted or mono- or polysubstituted $C_6$-$C_{14}$-aryl group, where the substituents have the definitions given for $R^2$, 2-(2-propoxy)phen-1-yl; 2-methoxyphen-1-yl; 2,4,5-trimethoxyphenyl; or ferrocenyl.

2. An N-heterocyclic carbene complex as claimed in claim 1, wherein the ring B is a heterocycle selected from the group comprising 1,3-disubstituted imidazol-2-ylidenes, 1,3-disubstituted imidazolin-2-ylidenes, 1,3-disubstituted tetrahydro-pyrimidin-2-ylidenes, 1,3-disubstituted diazepin-2-ylidenes, 1,3-disubstituted dihydrodiazepin-2-ylidenes, 1,3-disubstituted tetrahydrodiazepin-2-ylidenes, N-substituted thiazol-2-ylidenes, N-substituted thiazolin-2-ylidenes, N-substituted triazol-2-ylidenes, mono- or polysubstituted dihydrotriazol-2-ylidenes, mono- or polysubstituted triazolin-2-ylidenes, N-substituted thiadiazol-2-ylidenes, mono- or polysubstituted thiadiazolin-2-ylidenes and mono- or polysubstituted tetrahydrotriazol-2-ylidenes.

3. An N-heterocyclic carbene complex as claimed in claim 1, wherein the ring B is bonded covalently via a spacer group to a solid support.

4. An N-heterocyclic carbene complex as claimed in claim 3, wherein the solid support is a polymeric support, and the spacer group is a $C_1$-$C_{20}$-α,ω-dioxaalkylene or a $C_1$-$C_{20}$-alkyleneoxy group.

5. An N-heterocyclic carbene complex as claimed in claim 3, wherein the solid support is an inorganic support, and the spacer group is an alkyl-$Si(O)_3$ or an alkyl-$SiR(O)_2$ group in which R has the same definition as $R^2$.

6. An N-heterocyclic carbene complex as claimed in claim 1, wherein $R^1$ in formulae I, II, III or IV is t-butyl, an unsubstituted or substituted phenyl, ferrocenyl or $CMe_2Ph$, $R^{1'}$ in addition to H may have all the definitions mentioned for $R^1$ and substituents on the phenyl may have the same definition as $R^2$.

7. An N-heterocyclic carbene complex as claimed in claim 1, wherein the non-coordinating anions as $X^1$ and $X^2$ are selected from tetrakis(3,5-bis-(trifluoromethyl)phenyl)borate, tetrakis(penta-fluorophenyl)borate, tetrakis(nonafluoro-t-butoxy)-aluminate, tetrafluoroborate, hexafluorophosphate or hexafluoroantimonate.

8. A method of conducting an olefin metathesis reaction, the method including:
    contacting a substrate for the olefin methathesis reaction with a catalyst, wherein the catalyst is an N-heterocyclic carbene complex according to claim 1.

9. The method as claimed in claim 8, wherein the olefin metathesis reaction is an asymmetric or desymmetrizing ring-closing metathesis, a cross-metathesis, a ring-opening cross-metathesis, a (cross-)ene-yne metathesis, a ring-closing ene-yne metathesis, a cross-ene-diyne metathesis, a tandem ring-opening-ring-closing metathesis, a ring-opening metathesis polymerization (ROMP), a 1-alkyne polymerization, an acyclic diene metathesis polymerization (ADMET) or a cyclopolymerization of α,ω-diynes.

10. The method as claimed in claim 8, wherein the olefin metathesis reaction is an olefinolysis of fatty acid esters.

11. The method as claimed in claim 10, wherein the olefinolysis of fatty acid esters comprises the olefinolysis of vegetable oils and fats.

12. The method as claimed in claim 11, wherein the vegetable oils are selected from the group consisting of castor oil, palm oil, and coconut oil.

13. The method as claimed in claim 12, wherein the vegetable oils are combined with at least one of ethylene and butene.

14. The method as claimed in claim 8, wherein the catalyst is a compound of formula II or IV and the method further comprises:
    dissolving the compound of formula II or IV in an organic solvent (I) or in an ionic liquid to form a solution,
    applying the solution in the form of a thin film to a support material,
    introducing the support material including the thin film into a reaction vessel, and introducing a substrate into the reaction vessel, wherein the substrate is dissolved in a solvent (II) that is immiscible with the organic solvent (I) or the ionic liquid.

15. The method as claimed in claim 14, wherein the ionic liquid used is 1,3-dimethyl-imidazolium salt, 1,2,3-trimethylimidazolium salt, 1-butyl-3-methylimidazolium salt, 1-butyl-2,3-dimethylimidazolium salt, and the solvent (II) immiscible with the ionic liquid employed is toluene, pentane, hexane, heptane, octane, or a combination thereof.

16. The method as claimed in claim 14, wherein the substrate is charged continuously into the reaction vessel and resulting reaction products are discharged continuously therefrom.

17. The method as claimed in claim 14, wherein the support material is an inorganic support material or a polymer-organic support material.

18. The method as claimed in claim 17, wherein the inorganic support material comprises silicon dioxide.

19. The method as claimed in claim 17, wherein the polymer-organic support material is a polymer-organic monolithic support material.

\* \* \* \* \*